US012600743B2

(12) United States Patent
Asada

(10) Patent No.: US 12,600,743 B2
(45) Date of Patent: Apr. 14, 2026

(54) METHOD FOR PRODUCING OLIGONUCLEIC ACID COMPOUND

(71) Applicant: NIPPON SHINYAKU CO., LTD., Kyoto (JP)

(72) Inventor: Junshi Asada, Kyoto (JP)

(73) Assignee: NIPPON SHINYAKU CO., LTD., Kyoto (JP)

( * ) Notice: Subject to any disclaimer, the term of this patent is extended or adjusted under 35 U.S.C. 154(b) by 890 days.

(21) Appl. No.: 17/776,343

(22) PCT Filed: Nov. 13, 2020

(86) PCT No.: PCT/JP2020/042505
§ 371 (c)(1),
(2) Date: May 12, 2022

(87) PCT Pub. No.: WO2021/095874
PCT Pub. Date: May 20, 2021

(65) Prior Publication Data

US 2023/0018780 A1 Jan. 19, 2023

(30) Foreign Application Priority Data

Nov. 13, 2019 (JP) ................................ 2019-205625

(51) Int. Cl.
*C07H 21/00* (2006.01)
*C07H 1/00* (2006.01)

(52) U.S. Cl.
CPC ............... *C07H 21/00* (2013.01); *C07H 1/00* (2013.01)

(58) Field of Classification Search
CPC ................................ C07H 21/00; Y02P 20/55
See application file for complete search history.

(56) References Cited

U.S. PATENT DOCUMENTS

| | | | | |
|---|---|---|---|---|
| 6,040,439 | A | 3/2000 | Hayakawa et al. | |
| 6,642,373 | B2 * | 11/2003 | Manoharan ............ | C07H 21/00 536/25.4 |
| 8,969,551 | B2 | 3/2015 | Ueda | |
| 9,278,987 | B2 | 3/2016 | Hanson et al. | |
| 10,415,036 | B2 | 9/2019 | Torii et al. | |
| 11,560,401 | B2 * | 1/2023 | Kotobuki ............... | C07H 21/00 |
| 2003/0191304 | A1 | 10/2003 | Manoharan et al. | |
| 2010/0234281 | A1 | 9/2010 | Weller et al. | |
| 2013/0303745 | A1 | 11/2013 | Lange et al. | |
| 2017/0218361 | A1 | 8/2017 | Takahashi et al. | |
| 2021/0261596 | A1 | 8/2021 | Kotobuki et al. | |

FOREIGN PATENT DOCUMENTS

| | | | |
|---|---|---|---|
| EP | 2 623 507 | 8/2013 | |
| EP | 2 816 053 | 12/2014 | |
| EP | 2 921 499 | 9/2015 | |
| EP | 3 015 467 | 5/2016 | |
| EP | 3 208 277 | 8/2017 | |
| EP | 3 792 269 | 3/2021 | |
| JP | H10109994 A * | 4/1998 | |
| JP | 11-80185 | 3/1999 | |
| JP | 2002-517404 | 6/2002 | |
| JP | 2010-527945 | 8/2010 | |
| JP | 5548852 | 5/2014 | |
| WO | 91/09033 | 6/1991 | |
| WO | 99/62922 | 12/1999 | |
| WO | 03/006475 | 1/2003 | |
| WO | 2008/141682 | 11/2008 | |
| WO | 2012/043730 | 4/2012 | |
| WO | 2013/074834 | 5/2013 | |
| WO | 2013/122236 | 8/2013 | |
| WO | 2014/077292 | 5/2014 | |
| WO | 2014/189142 | 11/2014 | |
| WO | 2016/060135 | 4/2016 | |
| WO | WO-2019060862 A1 * | 3/2019 | .......... C07F 9/65583 |
| WO | 2019/216433 | 11/2019 | |

OTHER PUBLICATIONS

Torii, T., et al. WO2014/189142A1. English Translation. (Year: 2014).*
Shirakawa, S., et al. Angew. Chem. Int. Ed. 2015, 54, 15767-15770. (Year: 2015).*
"Nucleoside." Merriam-Webster.com Dictionary, Merriam-Webster, https://www.merriam-webster.com/dictionary/nucleoside. Accessed Mar. 26, 2025. (Year: 2025).*
Taguma K., JP-H10109994-A. 1998, English Translation (Year: 1998).*
Ravikumar, V. T., et al. Gene. 149, (1994), 157-161. (Year: 1994).*
Office Action dated Jan. 29, 2024 in counterpart Singapore Patent Application No. 11202204985P, 10 pages.
Database Registry, Chemical Abstracts Services, CAS Registry No. 1112-67-0 (Entered STN: Nov. 16, 1984); 479500-35-1 (Entered STN: Jan. 20, 2003); 64697-40-1 (Entered STN: Nov. 16, 1984), 1 page.
International Search Report issued Dec. 28, 2020 in International (PCT) Application No. PCT/JP2020/042505.
International Preliminary Report on Patentability dated May 27, 2022 in International (PCT) Application No. PCT/JP2020/042505.
Caruthers, Marvin H. et al., "Chemical Synthesis of DNA and DNA Analogues", Acc. Chem. Res., 1991, vol. 24, pp. 278-284.

(Continued)

*Primary Examiner* — Andrea Olson
*Assistant Examiner* — Samuel L Galster
(74) *Attorney, Agent, or Firm* — Wenderoth, Lind & Ponack, L.L.P.

(57) ABSTRACT

The present invention relates to a method for producing a compound [C] of the general formula [C] by subjecting a compound [A] having a hydroxyl group or a primary or secondary amino group and a compound [B] having a phosphorous atom-containing substituent group of the general formula [1] to a condensation reaction, characterized in that the method is carried out in the presence of at least one reaction accelerator selected from the group consisting of a quaternary ammonium salt, a quaternary imidazolium salt, a quaternary morpholinium salt, a quaternary phosphonium salt, a quaternary piperidinium salt, a quaternary pyridinium salt, a quaternary pyrrolidinium salt and a quaternary sulfonium salt.

10 Claims, 1 Drawing Sheet

(56) References Cited

OTHER PUBLICATIONS

Extended European Search Report issued Mar. 13, 2024 in corresponding European Patent Application No. 20886751.5, 13 pages.
Harakawa et al., "Development of an efficient method for phosphorodiamidate bond formation by using inorganic salts", Bioorganic & Medicinal Chemistry Letters, 2012, vol. 22, No. 3, pp. 1445-1447, 3 pages.
Office Action issued Nov. 12, 2024 in Japanese Patent Application No. 2021-556191, with English-language Translation.
Canadian Office Action issued Jan. 16, 2025 in corresponding Canadian Patent Application No. 3,161,586.
Invitation to Respond to Written Opinion issued Dec. 12, 2025 in corresponding Singapore Patent Application No. 11202204985P.
Office Action dated Jan. 14, 2026 in corresponding Korean Patent Application No. 10-2022-7019550, with English translation.
Xia Wei, "Coupling activators for the oligonucleotide synthesis via phosphoramidite approach", Tetrahedron, 2013, vol. 69, No. 18, pp. 3615-3637.

* cited by examiner

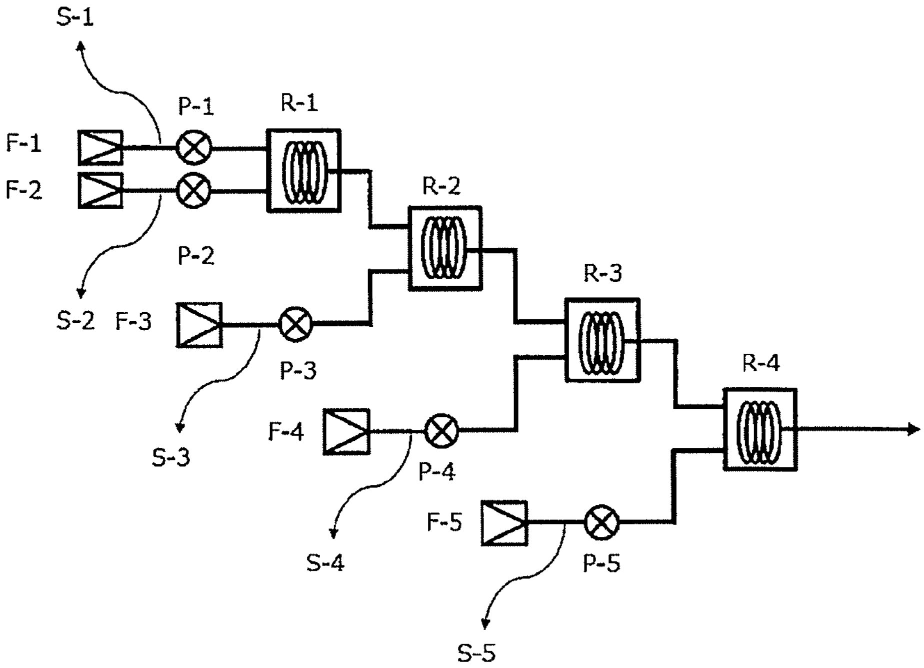
S-1
P-1
R-1
F-1
F-2
R-2
P-2
R-3
S-2
F-3
P-3
R-4
F-4
S-3
P-4
F-5
S-4
P-5
S-5

METHOD FOR PRODUCING OLIGONUCLEIC ACID COMPOUND

TECHNICAL FIELD

The present invention relates to a novel method for producing an oligonucleic acid compound.

BACKGROUND ART

A solid-phase method and a liquid-phase method are known as methods for preparing an oligonucleic acid compound. The solid-phase method is a heterogeneous reaction method in which a nucleic acid is extended while a substrate supported on a solid-phase carrier is brought into contact with a solution containing a reaction reagent. In the solid-phase method, a so-called batch method is used in which a reaction vessel with a filter is used and a reaction is carried out in the vessel (see, for example, Non-Patent Document 1 and Patent Document 1). In addition, a pseudo-flow synthesis method is also known in which, as in an automatic nucleic acid synthesizer (for example, DNA, RNA synthesizer), a solid-phase carrier is placed in a column and a solution containing a reaction reagent is passed through the column to cause a reaction.

On the other hand, the liquid-phase method is a homogeneous reaction method in which a nucleic acid is extended by causing a reaction in a solution containing both a substrate and a reaction reagent. In the liquid-phase method as well, a batch method in which a reaction is carried out in a vessel is used (see, for example, Patent Document 2 and Patent Document 3).

In any of the cases of the solid-phase method, the liquid-phase method, the batch method, and the pseudo-flow synthesis method, in a chemical synthesis method for an oligonucleic acid compound, a nucleic acid is extended by repeating many times a "deprotection" reaction for removing a protective group for an oxygen atom or amino group on a nucleic acid compound, and a "condensation" reaction for forming a bond between a phosphorus atom and an oxygen atom or nitrogen atom deprotected to be enabled to react.

Among them, controlling the reaction efficiency or the reaction rate in the "condensation" reaction for forming a bond between a phosphorus atom and an oxygen atom or nitrogen atom is very important in the preparation of an oligonucleic acid compound, and the conditions of this condensation reaction are factors that have a great impact on the preparation period of the oligonucleic acid compound.

Since the solid-phase method is a heterogeneous reaction between a solid-phase carrier and a solution, it is known that the reactivity of the condensation reaction decreases due to steric hindrance caused by the solid-phase carrier. Polystyrene resin is generally used as the solid-phase carrier. During the reaction, the polystyrene resin swells due to the reaction solvent used, and its volume becomes larger than that in a dry state. The degree of swelling depends on the reaction solvent.

Therefore, the reaction efficiency and the reaction rate of the condensation reaction in the solid-phase method depend on the reaction solvent used. In particular, with a polar solvent such as acetonitrile, which is generally used for the synthesis of oligonucleic acid compounds, the degree of swelling of the polystyrene resin is not so high, so that the use of a polar solvent in the solid-phase method is not preferable from the viewpoint of improving the reaction efficiency and the reaction rate of the condensation reaction.

On the other hand, as a homogeneous reaction method, a liquid-phase method and a synthetic method using a hydrophobic group-binding nucleoside, a pseudo-solid phase-protected nucleoside, or the like are known.

The liquid-phase method is a homogeneous reaction method in which a reaction is carried out in a solution containing both a substrate and a reaction reagent, and the reaction efficiency is higher than that of the solid-phase method, and the reaction rate is faster than that of the solid-phase method. However, column purification, etc., are required to remove the reaction reagent and a reaction solvent that are to be impurities.

Similar to the liquid-phase method, in the synthetic method using a hydrophobic group-binding nucleoside, a pseudo-solid phase-protected nucleoside, or the like, a reaction can be carried out in a homogeneous system, and thus the reaction efficiency is higher than that of the solid-phase method, and the reaction rate is faster than that of the solid-phase method. Furthermore, after the reaction, unnecessary reaction reagent and reaction solvent can be removed by precipitating the target compound from the reaction mixture (see, for example, Patent Document 4).

In these homogeneous reaction methods, a non-polar solvent such as chloroform is used in a condensation reaction. However, for example, as reported in the synthesis of a morpholino nucleic acid (see, for example, Patent Document 5), the condensation reaction in the non-polar solvent requires a very long time, so that the use of a non-polar solvent in the homogeneous reaction is not preferable from the viewpoint of improving the reaction efficiency and the reaction rate of the condensation reaction.

PRIOR ART DOCUMENT

Patent Document

[Patent Document 1] WO991/09033A1

[Patent Document 2] WO2014/077292A1

[Patent Document 3] WO2013/122236A1

[Patent Document 4] Japanese Patent No. 5548852

[Patent Document 5] WO2016/060135A1

Non-Patent Document

[Non-Patent Document 1] Acc. Chem. Res., Vol. 24, 278-284, 1991

SUMMARY OF THE INVENTION

Problems to be Solved by the Invention

An object of the present invention is to provide a novel preparation method that can shorten the preparation period of an oligonucleic acid compound.

Solution to the Problems

The present inventors have found that a phosphate bond can be efficiently formed by using a reaction accelerator in a condensation reaction of an oligonucleic acid compound, and have achieved the present invention.

An example of the present invention is a method for producing a compound [C] by subjecting a compound [A] having a hydroxyl group or a primary or secondary amino group to a condensation reaction with a compound [B]

having a substituent group containing phosphorous atom of the general formula [1] (hereinafter, referred to as "substituent [1]"):

[1]

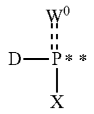

wherein

** represents a binding position with the residue of the compound [B],

D represents a halogen, 5- to 6-membered saturated cyclic amino, or di($C_{1-6}$ alkyl)amino, $W^0$ represents a lone pair of electrons, an oxygen atom, or a sulfur atom, and X represents a hydroxyl group substituted with a removable group under a neutral condition, 1,1,3,3-tetra($C_{1-6}$alkyl)guanidyl, $C_{1-6}$ alkoxy, di($C_{1-6}$ alkyl)amino, mono(amino-$C_{1-6}$ alkyl substituted with a removable group under a basic condition)amino, di(amino-$C_{1-6}$ alkyl substituted with a removable group under a basic condition)amino, or a substituent represented by general formula [2] (hereinafter, referred to as "substituent [2]"):

[2]

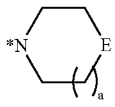

wherein

* represents a binding position with a phosphorus atom, a represents an integer from 0 to 2, E represents $CH_2$, CH-$A^1$, or N-$A^2$, $A^1$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, amino substituted with a removable group under a basic condition, mono($C_{1-6}$ alkyl)amino substituted with a removable group under a basic condition, di($C_{1-6}$ alkyl)amino, tri($C_{1-6}$ alkyl) ammonio, amino substituted with amidino substituted with a removable group under a basic condition, or a substituent represented by the following general formula [3] (hereinafter, referred to as "substituent [3]"):

[3]

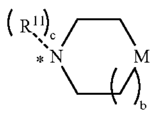

wherein

* represents a binding position with E, b represents an integer from 0 to 2, c represents 0 or 1, $R^{11}$ represents $C_{1-6}$ alkyl, and M represents $CH_2$, an oxygen atom, a sulfur atom, or N– (a removable group under a basic condition), and $A^2$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, a removable group under a basic condition, aryl, or heteroaryl, in the presence of at least one reaction accelerator selected from the group consisting of a quaternary ammonium salt, a quaternary imidazolium salt, a quaternary morpholinium salt, a quaternary phosphonium salt, a quaternary piperidinium salt, a quaternary pyridinium salt, a quaternary pyrrolidinium salt and a quaternary sulfonium salt to obtain the compound the general formula [C] (hereinafter, referred to as "compound [C]"):

[C]

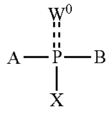

wherein $W^0$ and X are as defined above,

A represents a residue obtained by removing one hydrogen atom of the hydroxyl group or the primary or secondary amino group of the compound [A] from the compound [A], and B represents a residue obtained by removing the substituent [1] from the compound [B].

Effects of the Invention

An oligonucleic acid compound is a compound having a structure in which two or more nucleoside units are connected via phosphate bonds. In order to prepare an oligonucleic acid compound, it is necessary to carry out a condensation reaction many times to form a phosphate bond between adjacent nucleoside units.

According to the present invention, since a phosphate bond can be efficiently formed, it can be expected that the preparation time of the oligonucleic acid compound is shortened as a result.

BRIEF DESCRIPTION OF THE DRAWINGS

FIG. 1 illustrates a schematic diagram of a reactor used for a continuous reaction.

F-1 to F-5 denote solution vessels, P-1 to P-5 denote pumps, R-1 to R-4 denote flow reactors, and S-1 to S-5 denote flow channels.

EMBODIMENTS FOR CARRYING OUT THE INVENTION

The present invention is a method for producing a compound [C] by subjecting a compound [A] having a hydroxyl group or a primary or secondary amino group and a compound [B] having a substituent [1] to a condensation reaction in the presence of at least one reaction accelerator selected from the group consisting of a quaternary ammonium salt, a quaternary imidazolium salt, a quaternary morpholinium salt, a quaternary phosphonium salt, a quaternary piperidinium salt, a quaternary pyridinium salt, a quaternary pyrrolidinium salt and a quaternary sulfonium salt.

(A) Compound [A]

An example of the compound [A] that can be used in this preparation method is a compound having a hydroxyl group or a primary or secondary amino group.

One specific embodiment of the compound [A] is a compound containing one or more nucleoside units in a molecule thereof. Specifically, a compound containing 1 to 50 nucleoside units is suitable, a compound containing 1 to 30 nucleoside units is preferable, and a compound containing 1 to 25 nucleoside units is more preferable.

Examples of the nucleoside units contained in the compound [A] include nucleoside units represented by the following general formulae [4a] to [4d] (hereinafter, referred to as "nucleoside unit [4a]", "nucleoside unit [4b]", "nucleoside unit [4c]", and "nucleoside unit [4d]", respectively):

[4a]

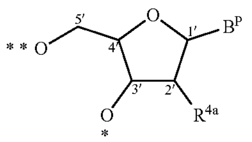

[4b]

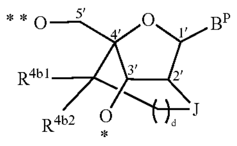

[4c]

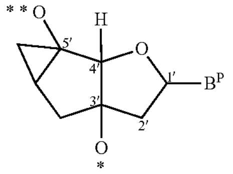

[4d]

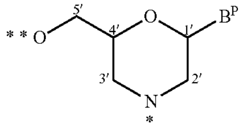

wherein

* represents (1) a binding position with a phosphate bond to an oxygen atom at the 5'-position of an adjacent nucleoside unit, (2) a binding position with a hydrogen atom, or (3) a binding position with a substituent represented by the following general formula [6] (hereinafter, referred to as "substituent [6]"):

G-T* [6]

wherein

* represents a binding position with the residue of the compound [A],

G represents (1) a silyl substituent, (2) long-chain alkyl-carbonyl, (3) benzoyl substituted with 1 to 5 long-chain alkyloxy and/or long-chain alkenyloxy, or (4) a substituent represented by the following general formula [7] (hereinafter, referred to as "substituent [7]"):

Z-L* [7]

wherein

* represents a binding position with T,

Z represents (1) (soluble polymer soluble in an organic solvent)-oxy, (2) (soluble polymer soluble in an organic solvent)-amino, (3) long-chain alkyloxy, (4) a solid phase carrier, or (5) a substituent represented by one of the following general formulae [8A] to [8N](hereinafter, referred to as "substituent [8A]", "substituent [8B]", "substituent [8C]", "substituent [8D]", "substituent [8E]", "substituent [8F]", "substituent [8G]", "substituent [8H]", "substituent [8I]", "substituent [8J]", "substituent [8K]", "substituent [8L]", "substituent [8M]", and "substituent [8N]", respectively):

[8A]

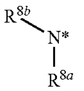

[8B]

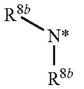

[8C]

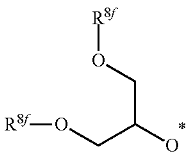

[8D]

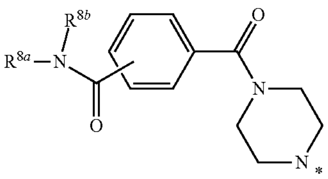

[8E]

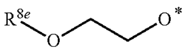

[8F]

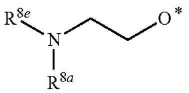

[8G]

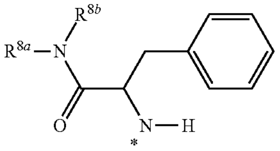

[8H]

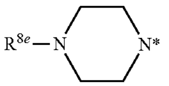

-continued

[8I]

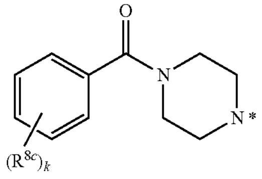

[8J]

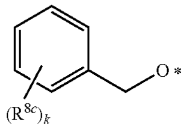

[8K]

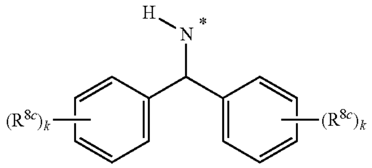

[8L]

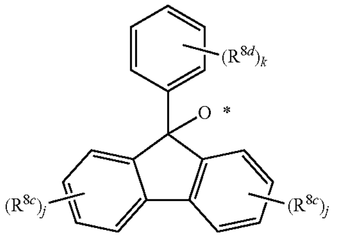

[8M]

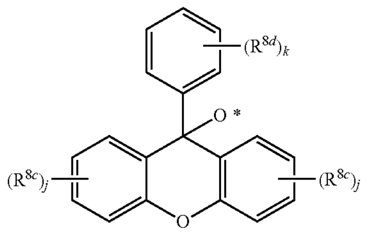

[8N]

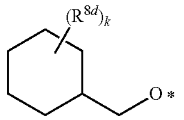

wherein

* represents a binding position with L, j represents an integer from 0 to 4, k represents an integer from 0 to 5, $R^{8a}$ represents a hydrogen atom or $C_{1-6}$ alkyl, $R^{8b}$ is the same or different and each represent long-chain alkyl, $R^{8c}$ is the same or different and each represent a substituent represented by one of the following general formulae [9A] to [9E](hereinafter, referred to as "substituent [9A]", "substituent [9B]", "substituent [9C]", "substituent [9D]", and "substituent [9E]", respectively):

[9A]

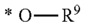

[9B]

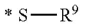

[9C]

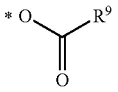

[9D]

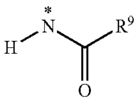

[9E]

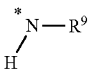

wherein

* represents a binding position, and $R^9$ represents long-chain alkyl and/or long-chain alkenyl, $R^{8d}$ is the same or different and each represent a hydrogen atom, a halogen, long-chain alkyl optionally substituted with 1 to 13 halogens, or long-chain alkyloxy optionally substituted with 1 to 13 halogens, $R^{8e}$ represents (1) long-chain alkyl, (2) long-chain alkyl-carbonyl, or (3) benzoyl substituted with 1 to 5 long-chain alkyloxy and/or long-chain alkenyloxy, and $R^{8f}$ represents (1) long-chain alkyl, (2) long-chain alkyl-carbonyl, or (3) long-chain alkenyl-carbonyl, and L represents a substituent represented by general formula [10] (hereinafter, referred to as "substituent [10]"):

[10]

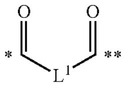

wherein

* represents a binding position with Z,

** represents a binding position with oxygen atom, and $L^1$ represents an optionally substituted $C_{2-10}$ alkylene or an optionally substituted $C_{6-10}$ arylene, and T represents a single bond or a substituent represented by general formula [11] (hereinafter, referred to as "substituent [11]"):

[11]

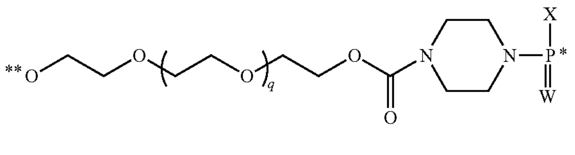

wherein

X is as defined above,

W represents a lone pair of electrons, an oxygen atom, or a sulfur atom,

* represents a binding position with oxygen atom,

** represents a binding position with G, and q represents an integer from 0 to 10, provided that T is a single bond when G is a silyl substituent,

** represents (1) a binding position with a phosphate bond to an oxygen atom at the 3'-position of or a nitrogen atom at the 3'-position of an adjacent nucleoside unit, (2) a binding position with a hydrogen atom, or (3) a binding position with the substituent [6], d represents 0 or 1, $B^P$ represents an optionally protected nucleic acid base, $R^{4a}$ represents a hydrogen atom, a hydroxyl group substituted with a removable group under a neutral condition, $C_{1-6}$ alkyl, $C_{1-6}$ alkoxy, $C_{1-6}$ alkoxy-$C_{1-6}$ alkyl, a halogen, nitro, or cyano, $R^{4b1}$ and $R^{4b2}$ are each the same or different and each represent a hydrogen atom or $C_{1-6}$ alkyl, or $R^{4b1}$ and $R^{4b2}$ are taken together with an adjacent carbon atom to form carbonyl, and J represents an oxygen atom or N—$R^{4b3}$ wherein $R^{4b3}$ represents $C_{1-6}$ alkyl.

Preferred embodiments of the nucleoside unit [4a] to [4d] are, for example, nucleoside units represented by the following general formulae [4a1] to [4d1] (hereinafter, referred to as "nucleoside unit [4a1]", "nucleoside unit [4b1]", "nucleoside unit [4c1]", and "nucleoside unit [4d1]", respectively):

[4a1]

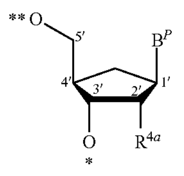

[4b1]

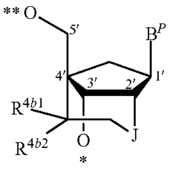

[4c1]

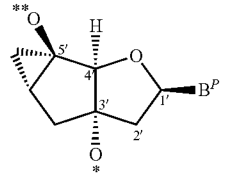

[4d1]

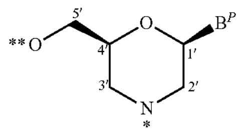

wherein d, $B^P$, J, $R^{4a}$, $R^{4b1}$, and $R^{4b2}$ are as defined above,

* represents (1) a binding position with a phosphate bond to an oxygen atom at the 5'-position of an adjacent nucleoside unit, (2) a binding position with a hydrogen atom, or (3) a binding position with the substituent [6], and

** represents (1) a binding position with a phosphate bond to an oxygen atom at the 3'-position of or a nitrogen atom at the 3'-position of an adjacent nucleoside unit, (2) a binding position with a hydrogen atom, or (3) a binding position with the substituent [6].

In the case where the compound [A] contains a plurality of nucleoside units in a molecule thereof, adjacent nucleoside units in the compound are preferably bound to each other via a phosphate bond.

The phosphate bonds between the nucleoside units of the compound [A] are each the same or different and are each, for example, a bond represented by the following general formula [5] (hereinafter, referred to as "phosphate bond [5]")

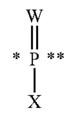

[5]

wherein

X is as defined above, one of * and ** represents a binding position with an oxygen atom at the 3'-position of or a nitrogen atom at the 3'-position of a nucleoside unit, and the other of * and ** represents a binding position with an oxygen atom at the 5'-position of a nucleoside unit different from said nucleoside unit, and W represents a lone pair of electrons, an oxygen atom or a sulfur atom.

W is preferably an oxygen atom or a sulfur atom, and more preferably an oxygen atom.

Hereinafter, typical examples of the compound [A] is described.

(A-1) Compound [A] Comprising One or More Nucleoside Units [4d]

In the nucleoside unit represented by the above general formula [4d],

* is (1) a binding position with a phosphate bond to an oxygen atom at the 5'-position of an adjacent nucleoside unit, or (2) a binding position with a hydrogen atom, and

** is (1) a binding position with a phosphate bond to a nitrogen atom at the 3'-position of an adjacent nucleoside unit, or (2) a binding position with the substituent [6].

One embodiment of the compound [A] is, for example, a compound in which the oxygen atom at the 5'-position of the 5'-terminal nucleoside unit is substituted with, for example, the substituent [6].

In this case, the phosphate bonds between the nucleoside units of the compound [A] are, for example, the same or different and are each the phosphate bond [5]. It should be noted that, in the phosphate bond represented by the above general formula [5], one of * and ** represents a binding position with a nitrogen atom at the 3'-position of a nucleoside unit, and the other of * and ** represents a binding position with an oxygen atom at the 5'-position of a nucleoside unit different from said nucleoside unit.

A more specific embodiment of the compound [A] is, for example, a compound represented by the following general formula [A-1] (hereinafter, referred to as "compound [A-1]"):

[A-1]

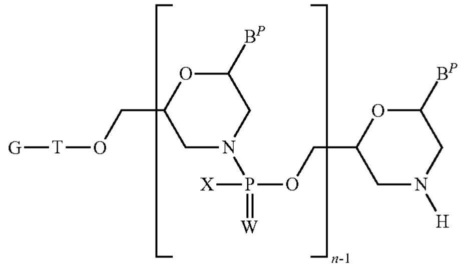

wherein $B^P$, G, T, X, and W are as defined above, and n represents an integer from 1 to 50.

n is suitably an integer from 1 to 50, preferably an integer from 1 to 30, and more preferably an integer from 1 to 25.

A more specific embodiment of the compound [A] is, for example, a compound of general formula [A-1-2]:

Formula [A-1-2]:

[A-1-2]

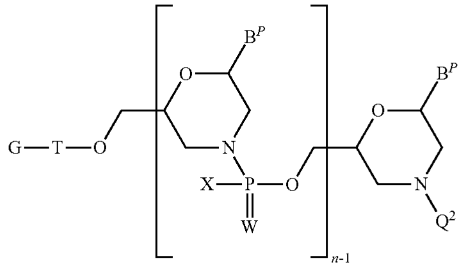

wherein $B^P$ is an optionally protected nucleic acid base, $Q^2$ is H or a removable group under an acidic condition, W represents a lone pair of electrons, an oxygen atom or a sulfur atom, preferably an oxygen atom or a sulfur atom and more preferably an oxygen atom, X is di($C_{1-6}$ alkyl)amino, G is selected from the group consisting of the following formulae:

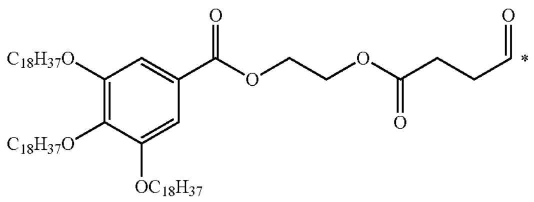

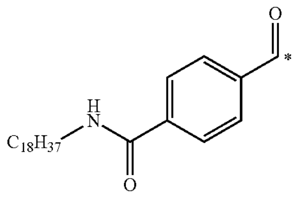

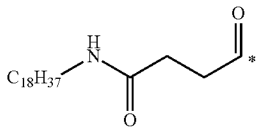

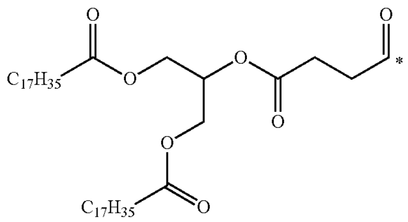

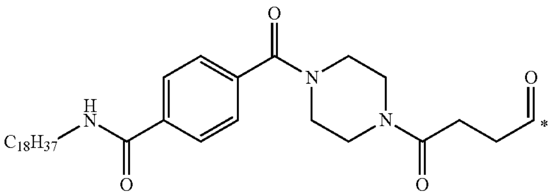

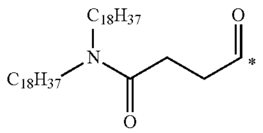

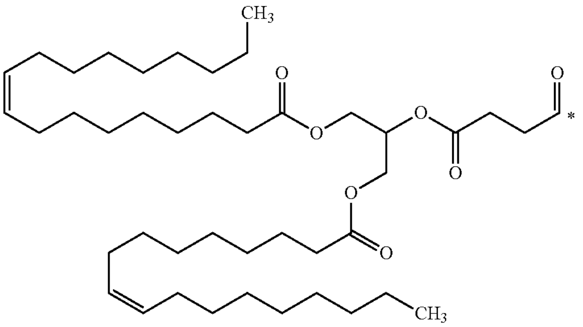

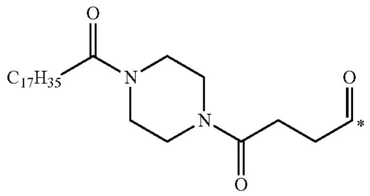

-continued

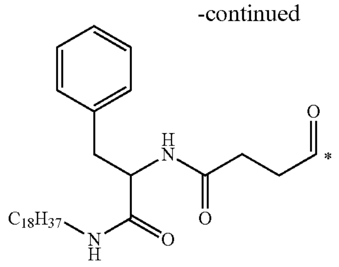

wherein

* represents a binding position with T,

T is a single bond, and n is 1 to 25.

(A-2) Compound [A] Comprising One or More Nucleoside Units Selected from Group Consisting of Nucleoside Unit [4a], Nucleoside Unit [4b], and Nucleoside Unit [4c]

In each of the nucleoside units represented by the above general formulae [4a], [4b], and [4c],

* is (1) a binding position with a phosphate bond to an oxygen atom at the 5'-position of an adjacent nucleoside unit, or (2) a binding position with the substituent [6], and

** is (1) a binding position with a phosphate bond to an oxygen atom at the 3'-position of an adjacent nucleoside unit, or (2) a binding position with a hydrogen atom.

One embodiment of the compound [A] is, for example, a compound in which the oxygen atom at the 3'-position of the 3'-terminal nucleoside unit is substituted with, for example, the substituent [6].

In this case, the phosphate bonds between the nucleoside units of the compound [A] are each, for example, suitably the phosphate bond [5]. It should be noted that, in the phosphate bond represented by the above general formula [5], one of * and ** represents an oxygen atom at the 3'-position of a nucleoside unit, and the other of * and ** represents a binding position with an oxygen atom at the 5'-position of a nucleoside unit different from said nucleoside unit.

A more specific embodiment of the compound [A] is, for example, a compound represented by the following general formula [A-2] (hereinafter, referred to as "compound [A-2] 1")

[A-2]

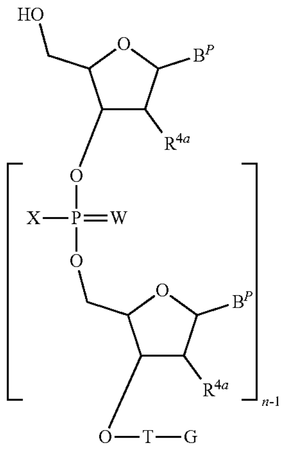

wherein n, $B^P$, G, $R^{4a}$, T, X, and W are as defined above.

Specific examples of the substituents [7] in the compound [A-1] and the compound [A-2] include the following substituents.

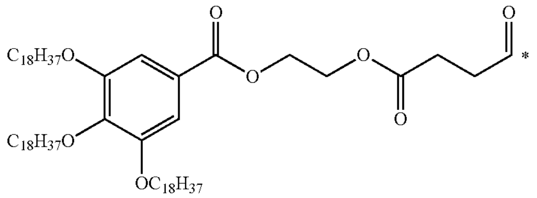

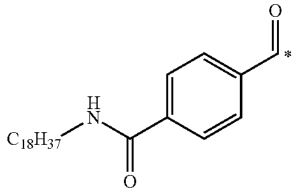

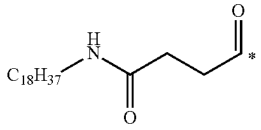

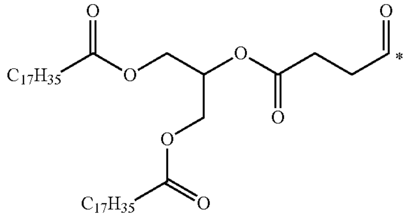

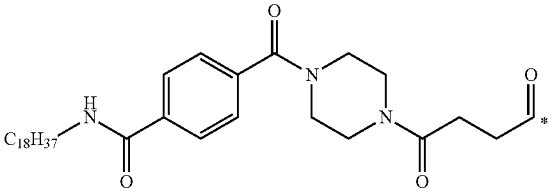

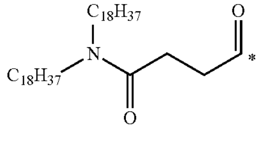

-continued

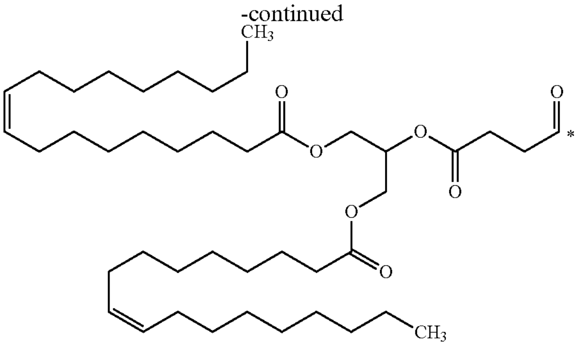

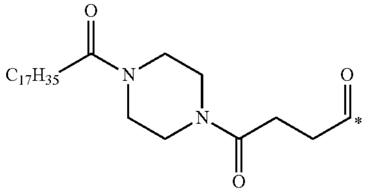

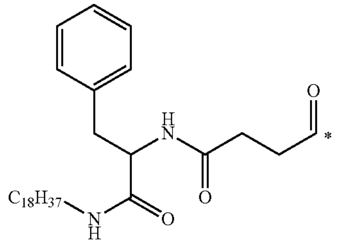

wherein * represents a binding position with T.

(B) Compound [B]

An example of the compound [B] that can be used in this preparation method is a compound having the substituent [1].

One specific embodiment of the compound [B] is, for example, a compound containing one or more nucleoside units in a molecule thereof. More specifically, a compound containing 1 to 10 nucleoside units is suitable, a compound containing 1 to 7 nucleoside units is preferable, and a compound containing 1 to 5 nucleoside units is more preferable.

Examples of the nucleoside units contained in the compound [B] include nucleoside units represented by the following general formulae [4e] to [4h] (hereinafter, referred to as "nucleoside unit [4e]", "nucleoside unit [4f]", "nucleoside unit [4g]", and "nucleoside unit [4h]", respectively):

[4e]

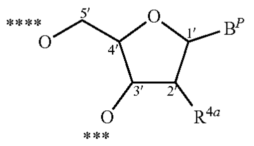

[4f]

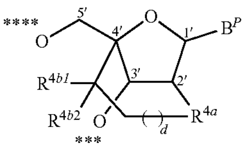

-continued

[4g]

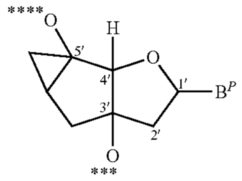

[4h]

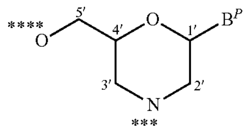

wherein d, $B^P$, J, $R^{4a}$, $R^{4b1}$b, and $R^{4b2}$ are as defined above,

*** represents (1) a binding position with a phosphate bond to an oxygen atom at the 5'-position of an adjacent nucleoside unit, (2) a binding position with the substituent [1], or (3) a binding position with a removable group under an acidic condition, and

**** represents (1) a binding position with a phosphate bond to an oxygen atom at the 3'-position of or a nitrogen atom at the 3'-position of an adjacent nucleoside unit, (2) a binding position with the substituent [1], or (3) a binding position with a removable group under an acidic condition.

Preferred embodiments of the nucleoside unit [4e] to [4h] are, for example, nucleoside units represented by the following general formulae [4e1] to [4h1] (hereinafter, referred to as "nucleoside unit [4e1]", "nucleoside unit [4f1]", "nucleoside unit [4g1]", and "nucleoside unit [4h1]", respectively):

[4e1]

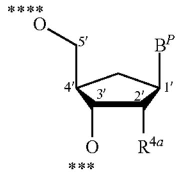

[4f1]

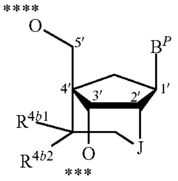

[4g1]

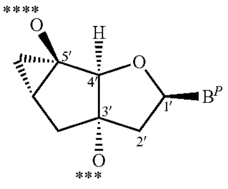

-continued

[4h1]

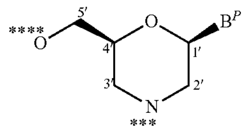

wherein d, $B^P$, J, $R^{4a}$, $R^{4b1}$, and $R^{4b2}$ are as defined above,

*** represents (1) a binding position with a phosphate bond to an oxygen atom at the 5'-position of an adjacent nucleoside unit, (2) a binding position with the substituent [1], or (3) a binding position with a removable group under an acidic condition, and

**** represents (1) a binding position with a phosphate bond to an oxygen atom at the 3'-position of or a nitrogen atom at the 3'-position of an adjacent nucleoside unit, (2) a binding position with the substituent [1], or (3) a binding position with a removable group under an acidic condition.

In the case where the compound [B] contains a plurality of nucleoside units in a molecule thereof, adjacent nucleoside units in the compound are preferably bound to each other via a phosphate bond.

In this case, the phosphate bonds between the nucleoside units of the compound [B] are, for example, the same or different and are each the phosphate bond [5]. It should be noted that, in the phosphate bond represented by the above general formula [5], one of * and ** represents an oxygen atom at the 3'-position of a nucleoside unit, and the other of * and ** represents a binding position with an oxygen atom at the 5'-position of a nucleoside unit different from said nucleoside unit.

Hereinafter, typical examples of the compound [B] is described.

(B-1) Compound [B] Comprising One or More Nucleoside Units [4h]

In the nucleoside unit represented by the above general formula [4h],

*** is (1) a binding position with a phosphate bond to an oxygen atom at the 5'-position of an adjacent nucleoside unit, or (2) a binding position with a removable group under an acidic condition, and

**** is (1) a binding position with a phosphate bond to a nitrogen atom at the 3'-position of an adjacent nucleoside unit, or (2) a binding position with the substituent [1].

One embodiment of the compound [B] is, for example, a compound in which a nitrogen atom at the 3'-position of the 3'-terminal nucleoside unit is substituted with a removable group under an acidic condition.

In this case, the phosphate bonds between the nucleoside units of the compound [B] are, for example, the same or different and are each the phosphate bond [5]. It should be noted that, in the phosphate bond represented by the above general formula [5], one of * and ** represents a nitrogen atom at the 3'-position of a nucleoside unit, and the other of * and ** represents a binding position with an oxygen atom at the 5'-position of a nucleoside unit different from said nucleoside unit.

In addition, at the oxygen atom at the 5'-position of the 5'-terminal nucleoside unit of the compound [B], the compound [B] suitably has a substituent containing a phosphorus atom and represented by the following general formula [1A]:

[1A]

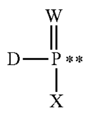

wherein

D, W, and X are as defined above, and

** represents a binding position with a residue of the compound [B].

A more specific embodiment of the compound [B] is, for example, a compound represented by the following general formula [B-1] (hereinafter, referred to as "compound [B-1]"):

[B-1]

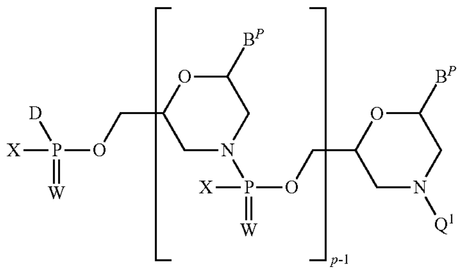

wherein $B^P$, D, X, and W are as defined above, p represents an integer from 1 to 10, and $Q^1$ represents a removable group under an acidic condition.

p is suitably an integer from 1 to 10, preferably an integer from 1 to 7, and more preferably an integer from 1 to 5.

Specific examples of the compound [B-1] with p=1 include compounds listed in Table 1 below.

TABLE 1
| Abbreviation | Chemical structure |
|---|---|
| morA | 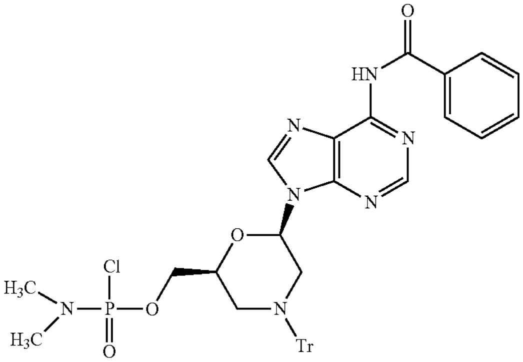 |
| morA-2 | 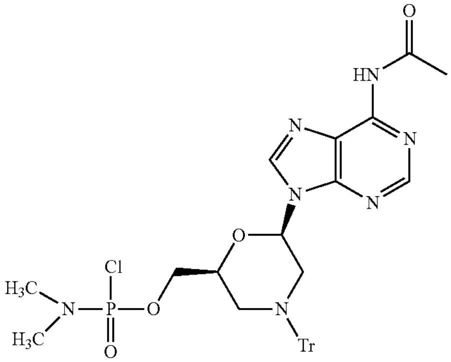 |
| morC | 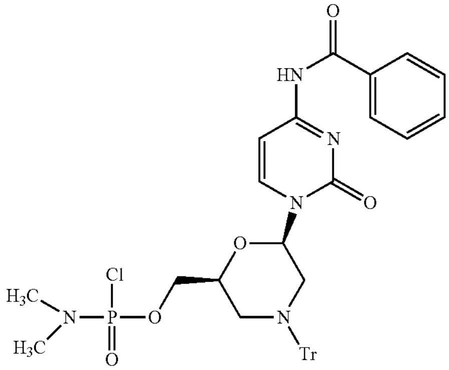 |
| morC-2 | 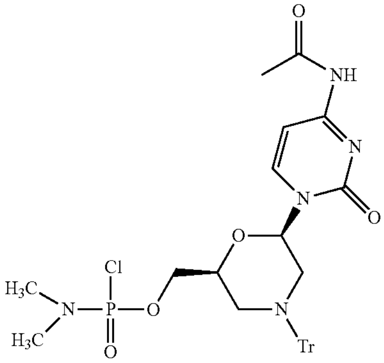 |

TABLE 1-continued
| Abbreviation | Chemical structure |
|---|---|
| morU | 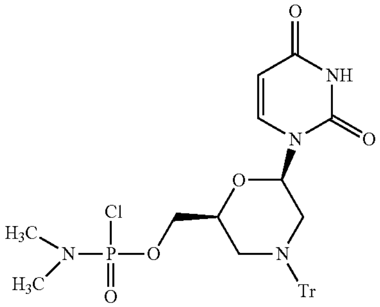 |
| morT | 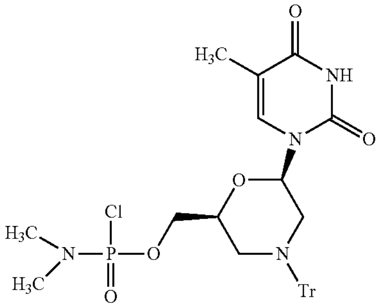 |
| morG | 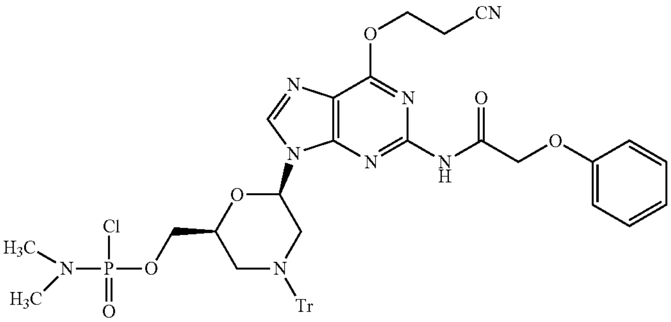 |
| morG-2 | 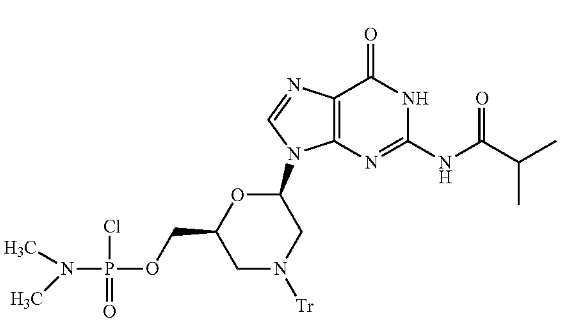 |

TABLE 1-continued

| Abbreviation | Chemical structure |
| --- | --- |
| morG-3 | 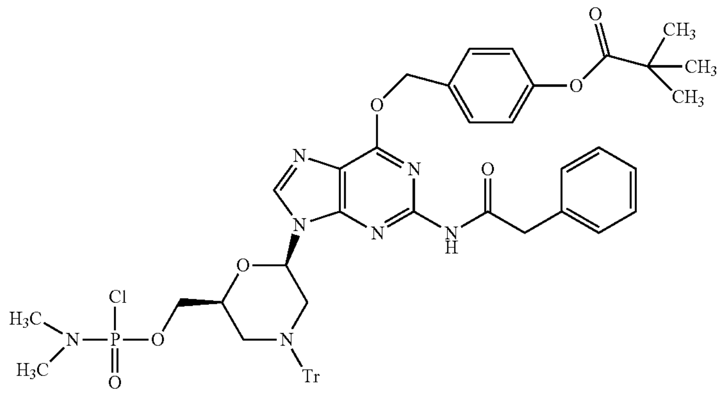 |

(B-2) Compound [B] Comprising One or More Nucleoside Units Selected from Group Consisting of Nucleoside Unit [4e], Nucleoside Unit [4f], and Nucleoside Unit [4g]

In each of the nucleoside units represented by the above general formulae [4e], [4f], and [4g],

*** is (1) a binding position with a phosphate bond to an oxygen atom at the 3'-position of an adjacent nucleoside unit, or (2) a binding position with the substituent [1], and

**** is (1) a binding position with a phosphate bond to an oxygen atom at the 5'-position of an adjacent nucleoside unit, or (2) a binding position with a removable group under an acidic condition.

One embodiment of the compound [B] is, for example, a compound in which an oxygen atom at the 5'-position of the 5'-terminal nucleoside unit is substituted with a removable group under an acidic condition.

In this case, the phosphate bonds between the nucleoside units of the compound [B] are, for example, the same or different and are each the phosphate bond [5]. It should be noted that, in the phosphate bond represented by the above general formula [5], one of * and ** represents an oxygen atom at the 3'-position of a nucleoside unit, and the other of * and ** represents a binding position with an oxygen atom at the 5'-position of a nucleoside unit different from said nucleoside unit.

In addition, at the oxygen atom at the 3'-position of the 3'-terminal nucleoside unit of the compound [B], the compound [B] suitably has a substituent containing a phosphorus atom and represented by the following general formula [1B]:

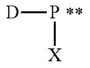

[1B]

wherein

D and X are as defined above, and

** represents a binding position with a residue of the compound [B].

One of more specific embodiments of the compound [B] is, for example, a compound represented by the following general formula [B-2] (hereinafter, referred to as "compound [B-21]")

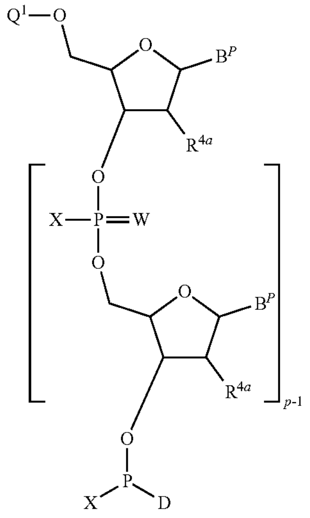

[B-2]

wherein p, $B^P$, D, $Q^1$, $R^{4a}$, X, and W are as defined above.

Specific examples of the compound [B-2] with p=1 include compounds listed in Table 2 below. In Table 2, DMTr represents dimethoxytrityl, and TBDMS represents tert-butyldimethylsilyl.

TABLE 2
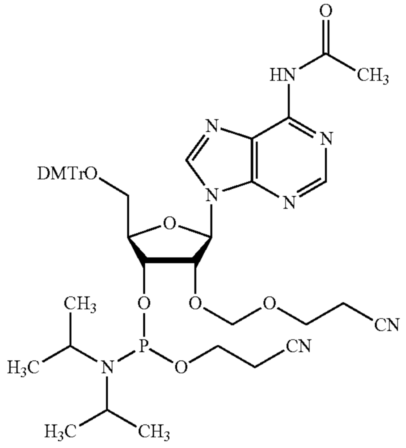
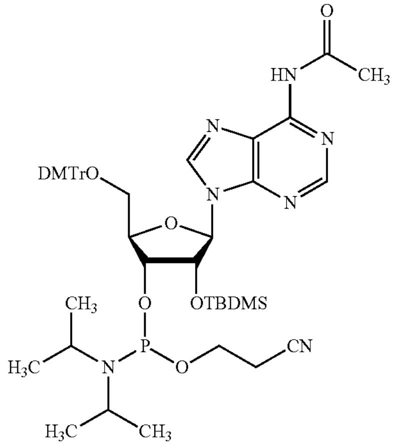
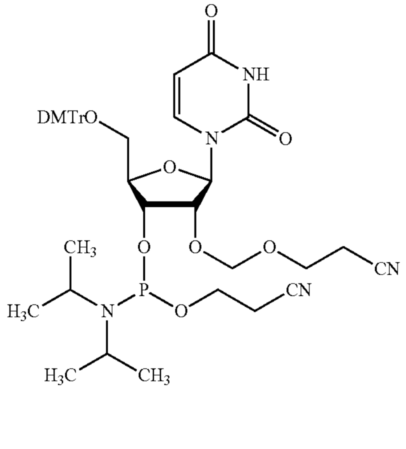
TABLE 2-continued
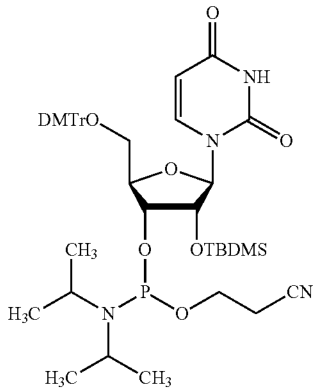
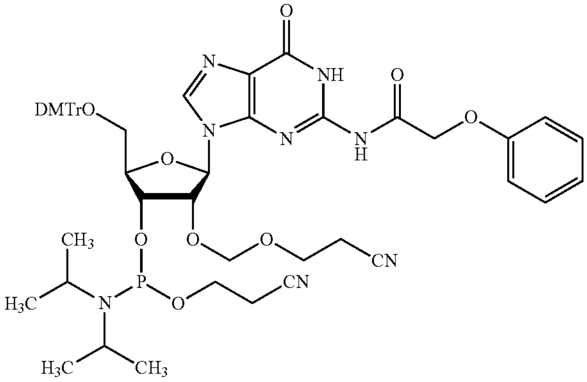
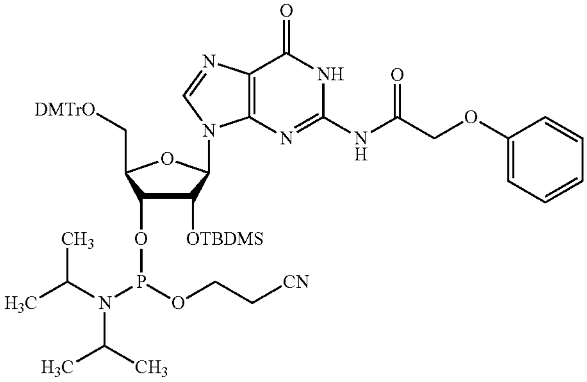
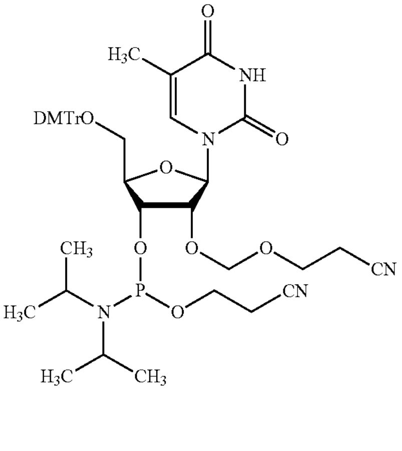

TABLE 2-continued

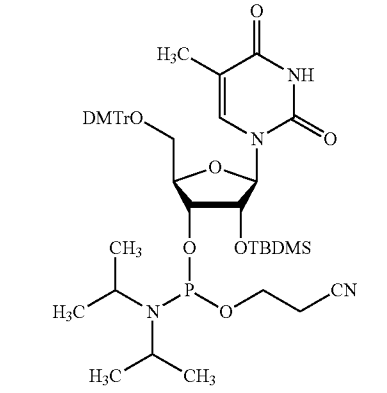

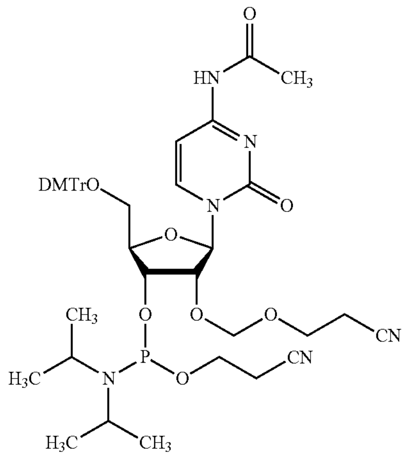

TABLE 2-continued

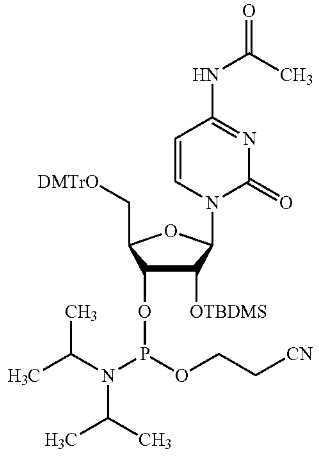

(C) Compound [C]

An example of the compound [C] is a compound that can be prepared by subjecting the compound [A] and the compound [B] to a condensation reaction.

Hereinafter, typical examples of the compound [C] is described.

(C-1) Compound [C] Comprising One or More Nucleoside Units [4d] and One or More Nucleoside Units [4h]

A specific embodiment of the compound [C] is, for example, a compound represented by the following general formula [C-1] (hereinafter, referred to as "compound [C-1]")

[C-1]

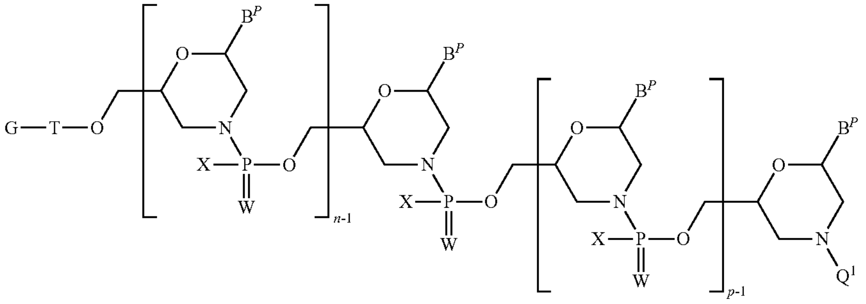

wherein n, p, $B^P$, G, $Q^1$, T, W, and X are as defined above.

As described below, examples of a phosphate bond newly formed in a method, for preparing the compound [C-1] by reacting the compound [A-1] with the compound [B-1] include the phosphate bond [5]. It should be noted that, in the phosphate bond represented by the above general formula [5], one of * and ** represents a nitrogen atom at the 3'-position of a nucleoside unit, and the other of * and ** represents a binding position with an oxygen atom at the 5'-position of a nucleoside unit different from said nucleoside unit.

(C-2) Compound [C] Comprising One or More Nucleoside Units Selected from Group Consisting of Nucleoside Unit [4a], Nucleoside Unit [4b], and Nucleoside Unit [4c] and One or More Nucleoside Units Selected from Group Consisting of Nucleoside Unit [4e], Nucleoside Unit [4f], and Nucleoside Unit [4g]

One specific embodiment of the compound [C] is, for example, a compound represented by the following general formula [C-2] (hereinafter, referred to as "compound [C-2]")

[C-2]

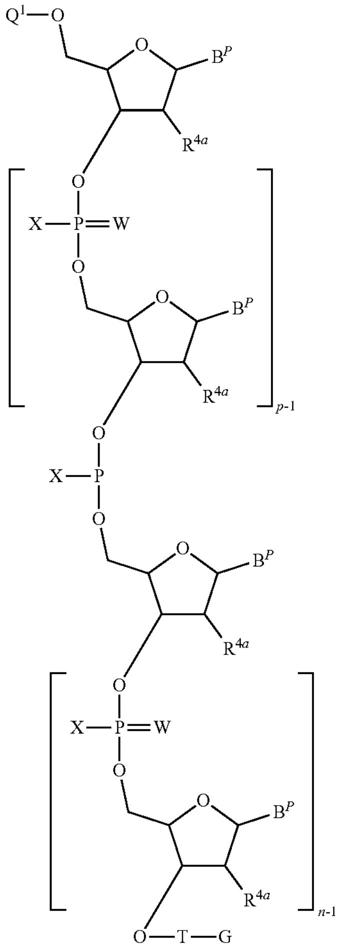

wherein n, p, $B^P$, G, $Q^1$, $R^{4a}$, T, W, and X are as defined above.

A phosphate bond newly formed in a method, for preparing the compound [C-2] by reacting the compound [A-2] with the compound [B-2], which is described hereinafter is, for example, a bond containing a phosphorus atom and represented by the following general formula [5a] (hereinafter, referred to as "phosphorous bond [5a]"):

[5a]

wherein

X is as defined above, and one of * an ** represents a binding position with an oxygen atom at the 3'-position of a nucleoside unit, and the other of * and ** represents a binding position with an oxygen atom at the 5'-position of a nucleoside unit different from said nucleoside unit.

By reacting the compound [C-2] with an oxidizing agent, the compound [C-2] can be converted to a compound having an oxidized phosphorus atom on a phosphorus bond in a molecule thereof and represented by the following general formula [D-2] (hereinafter, referred to as "compound [D-2]"):

[D-2]

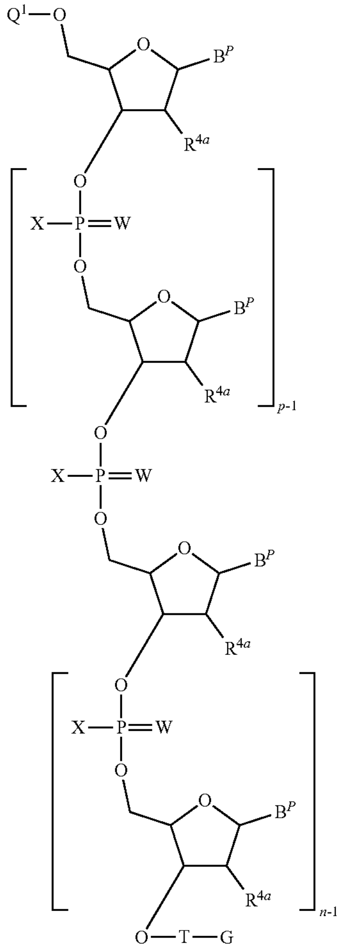

wherein n, p, $B^P$, G, $Q^1$, $R^{4a}$, T, W, and X are as defined above.

(D) Description of Terms

Examples of the "nucleic acid base", as used herein, include adenine, guanine, hypoxanthine, cytosine, thymine, uracil, and modified bases thereof. Examples of such modified bases include, but are not limited to, pseudouracil, 3-methyluracil, dihydrouracil, 5-alkylcytosines (for example, 5-methylcytosine), 5-alkyluracils (for example, 5-ethyluracil), 5-halouracils (5-bromouracil), 6-azapyrimidine, 6-alkylpyrimidines (6-methyluracil), 2-thiouracil, 4-thiouracil, 4-acetylcytosine, 5-(carboxyhydroxymethyl) uracil, 5'-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, $N^6$-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-$N^6$-isopentenyladenine, uracil-5-oxyacetic acid, 2-thiocytosine, purine, 2,6-diaminopurine, 2-aminopurine, isoguanine, indole, imidazole, and xanthine. The amino group or hydroxyl group of the nucleic acid base for $B^P$ may be protected.

Examples of the "optionally protected nucleic acid base", as used herein, includes both unprotected "nucleic acid base" and protected "nucleic acid base", such as adenine, guanine, hypoxanthine, cytosine, thymine, uracil, wherein the amino group and/or hydroxyl group is unprotected of protected.

The amino-protective group is not particularly limited as long as it is used as a protective group for a nucleic acid, and specific examples thereof include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl, and (dimethylamino)methylene. As the amino-protective group, benzoyl, acetyl, phenylacetyl, and 4-tert-butylphenoxyacetyl are preferable. Examples of the hydroxy-protective group include 2-cyanoethyl, 4-nitrophenethyl, phenylsulfonylethyl, methylsulfonylethyl, trimethylsilylethyl, phenyl optionally substituted with 1 to 5 electron-withdrawing groups at any substitutable positions, diphenylcarbamoyl, dimethylcarbamoyl, diethylcarbamoyl, methylphenylcarbamoyl, 1-pyrolidinylcarbamoyl, morpholinocarbamoyl, 4-(tert-butylcarboxy)benzyl, 4-[(dimethylamino)carboxy]benzyl, and 4-(phenylcarboxy)benzyl, (see, for example, WO2009/064471A1). As the hydroxy-protective group, 2-cyanoethyl, 4-nitrophenethyl, and 4-(tert-butylcarboxy)benzyl are preferable. A protective group for the hydroxyl group at the 6-position of guanine is preferably 2-cyanoethyl.

In one embodiment, examples of the protected nucleic acid base include those shown below.

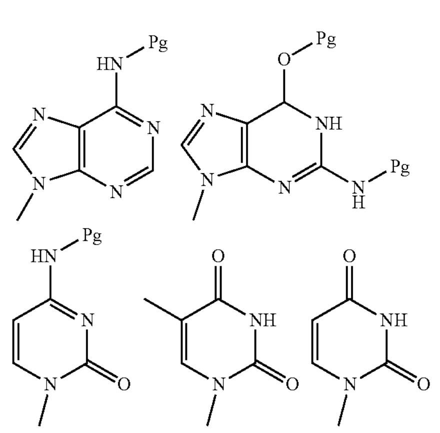

wherein Pg represents a protecting group.

A more specific embodiment of the protected nucleic acid base includes, but are not limited to, adenine ($A^{Bz}$) having an amino group protected by benzoyl, cytosine ($C^{Bz}$) having an amino group protected by benzoyl, and guanine ($G^{CE,Pac}$) having a hydroxyl group protected by 2-cyanoethyl and an amino group protected by phenoxyacetyl.

The "long-chain alkyl" indicates, for example, linear or branched alkyl having 10 to 300 carbon atoms, preferably indicates linear or branched alkyl having 10 to 100 carbon atoms, and more preferably indicates linear or branched alkyl having 10 to 30 carbon atoms.

Examples of the "long-chain alkyl" moieties of the "long-chain alkyl-carbonyl" and the "long-chain alkyloxy" include the same as those for the "long-chain alkyl".

The "long-chain alkenyl" indicates, for example, linear or branched alkenyl having 10 to 300 carbon atoms, preferably indicates linear or branched alkenyl having 10 to 100 carbon atoms, and more preferably indicates linear or branched alkenyl having 10 to 30 carbon atoms.

Examples of the "long-chain alkenyl" moieties of the "long-chain alkenyloxy" and the "long-chain alkyl-carbonyl" include the same as those for the "long-chain alkenyl".

Examples of the "halogen" include a fluorine atom, a chlorine atom, a bromine atom, and an iodine atom.

Examples of the "5- to 6-membered saturated cyclic amino" include a 5- to 6-membered saturated cyclic amino group that has one or two nitrogen atoms and optimally has one oxygen or sulfur atom as ring-constituting atoms, and specific examples thereof include 1-pyrrolidinyl, 1-imidazolidinyl, piperidino, 1-piperazinyl, 1-tetrahydropyrimidinyl, 4-morpholino, 4-thiomorpholino, 1-homopiperazinyl, and oxazolidine-3-yl.

The "$C_{1-6}$ alkyl" indicates linear or branched alkyl having 1 to 6 carbon atoms, and specific examples thereof include methyl, ethyl, n-propyl, isopropyl, n-butyl, isobutyl, sec-butyl, tert-butyl, n-pentyl, and n-hexyl.

The "$C_{1-6}$ alkoxy" indicates linear or branched alkoxy having 1 to 6 carbon atoms, and specific examples thereof include methoxy, ethoxy, n-propoxy, isopropoxy, n-butoxy, isobutoxy, sec-butoxy, tert-butoxy, n-pentyloxy, and n-hexyloxy.

Examples of the "$C_{1-6}$ alkoxy" moiety of the "$C_{1-6}$ alkoxy $C_{1-6}$ alkyl" include the same as those for the "$C_{1-6}$ alkoxy".

Examples of the "$C_{1-6}$ alkyl" moieties of the "di($C_{1-6}$ alkyl)amino", mono(amino-$C_{1-6}$ alkyl substituted with a removable group under a basic condition)amino, di(amino-$C_{1-6}$ alkyl substituted with a removable group under a basic condition)amino, mono($C_{1-6}$ alkyl)amino-$C_{1-6}$ alkyl, di($C_{1-6}$ alkyl)amino-$C_{1-6}$ alkyl, tri($C_{1-6}$ alkyl)ammonio-$C_{1-6}$ alkyl, mono($C_{1-6}$ alkyl)amino, di($C_{1-6}$ alkyl)amino, tri($C_{1-6}$ alkyl) ammonio, mono(amino-$C_{1-6}$ alkyl)amino, and di(amino-$C_{1-6}$ alkyl)amino include the same as those for the "$C_{1-6}$ alkyl".

The "$C_{2-10}$ alkylene" refers to a divalent group produced by removing one hydrogen atom bound to a different constituent carbon atom from linear or branched alkyl having 2 to 10 carbon atoms, and examples thereof include an ethylene group, a propylene group, an isopropylene group, a butylene group, a pentylene group, and a hexylene group. Such "alkylene" may be substituted with 1 to 12 halogens at any substitutable positions. As the "alkylene" for $L^1$, ethylene is particularly preferable.

The "$C_{6-10}$ arylene" refers to a divalent group produced by removing two hydrogen atoms bound to two different ring-constituting carbon atoms from a monocyclic or polycyclic aromatic hydrocarbon having 6 to 10 carbon atoms, and examples thereof include phenylene and naphthylene. Such "arylene" may be substituted with 1 to 6 halogens at any substitutable positions. As the "arylene" for $L^1$, phenylene is particularly preferable.

Examples of the "$C_{1-6}$ alkyl" moieties of the "1,1,3,3-tetra($C_{1-6}$ alkyl) guanidyl", the "$C_{1-6}$ alkoxy $C_{1-6}$ alkyl", the "di($C_{1-6}$ alkyl)amino", the "di($C_{1-6}$ alkyl)amino-$C_{1-6}$ alkyl", the "tri($C_{1-6}$ alkyl)ammonio", the "tri($C_{1-6}$ alkyl)ammonio-$C_{1-6}$ alkyl", the "mono($C_{1-6}$ alkyl)amino substituted with a removable group under a basic condition", the "mono($C_{1-6}$ alkyl)amino-$C_{1-6}$ alkyl substituted with a removable group under a basic condition", the "mono(amino-$C_{1-6}$ alkyl substituted with a removable group under a basic condition) amino", and the "di(amino-$C_{1-6}$ alkyl substituted with a removable group under a basic condition)amino" include the same as those for the "$C_{1-6}$ alkyl".

Examples of the "a removable group under an acidic condition" include trityl, monomethoxytrityl, and dimethoxytrityl.

An example of the "a removable group under a basic condition" is trifluoroacetyl.

Examples of the "a removable group under a neutral condition" include a group that can be removed by tetrabutylammonium fluoride or hydrogen trifluoride/triethylamine salt to act, and specific examples thereof include 2-cyanoethoxymethoxy, 2-cyanoethoxy-2-ethoxy, and tert-butyldimethylsilyl.

Examples of the "silyl substituent" include triphenylsilyl, diisopropylphenylsilyl, tert-butyldimethylsilyl, and tert-butyldiphenylsilyl.

An example of the "aryl" is phenyl.

Examples of the "heteroaryl" include pyridyl, pyrimidyl, pyridazil, pyrazinyl, thienyl, and furanyl.

As the "solid-phase carrier", any carrier that can be generally used for solid-phase synthesis of nucleic acids, peptides, peptide nucleic acids, sugars, etc., can be used without any particular problem. Examples thereof include controlled pore glass (CPG), oxalyzed controlled pore glass (see, for example, Nucleic Acids Research, Vol. 19, 1527 (1991)), TentaGel support-aminopolyethylene glycol derivatized support (see, for example, Tetrahedron Letters, Vol. 34, 3373 (1993)), Poros-polystyrene/divinylbenzene copolymers, polystyrene resins, and polyacrylamide resins.

Examples of the "soluble polymer soluble in an organic solvent" include non-crosslinked styrene polymers and polyethylene glycol derivatives.

Examples of the "soluble polymer soluble in an organic solvent" moiety of the "(soluble polymer soluble in an organic solvent)-oxy" and the "(soluble polymer soluble in an organic solvent)-amino" include the same as those for the "soluble polymer soluble in an organic solvent".

Examples of the "non-crosslinked styrene polymers" include derivatives of polystyrene not crosslinked with divinylbenzene and having a spacer such as polyethylene glycol (TentaGel series, ArgoGel series).

Examples of the "polyethylene glycol derivatives" include derivatives, of polyethylene glycol with a molecular weight of 100 to 40,000, having a substituent (SUNBRIGHT (registered trademark) series).

(E) Preparation Method for Compound [C]

The compound [C] can be prepared, for example, by subjecting the compound [A] having a hydroxyl group or a primary or secondary amino group and the compound [B] having the substituent [1], to a condensation reaction.

As described in the following Examples and Test Examples, in the preparation of the compound [C], a phosphate bond can be efficiently formed in the presence of a reaction accelerator.

The solvent that can be used in this preparation method is not limited so long as it is a solvent generally used in the art, and a single solvent may be used, or two or more solvents may be used in combination.

Examples of the solvent that can be used in this preparation method include aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like. These solvents may be used in combination.

In this preparation method, a base may be used if necessary. Examples of the "base" that can be used in this preparation method include diisopropylamine, N,N-diisopropylethylamine, triethylamine, N-ethylmorpholine, and 2,6-lutidine.

The amount of the base that can be used in this preparation method is, for example, suitably in the range of 1 mole to 100 moles, preferably in the range of 1 mole to 10 moles, and further preferably in the range of 1 mole to 5 moles, per mole of the compound [A].

In this preparation method, a reaction accelerator is used. The "reaction accelerator" that can be used in this preparation method may be at least one selected from the group consisting of quaternary ammonium salts, quaternary imidazolium salts, quaternary morpholinium salts, quaternary phosphonium salts, quaternary piperidinium salts, quaternary pyridinium salts, quaternary pyrrolidinium salts, and quaternary sulfonium salts, preferably one selected from the group consisting of quaternary ammonium salts, quaternary imidazolium salts, quaternary phosphonium salts, quaternary pyridinium salts, and quaternary pyrrolidinium salts. More preferably, a salt containing a quaternary nitrogen cation selected from the group consisting of quaternary ammonium salts, quaternary imidazolium salts, quaternary pyridinium salts and quaternary pyrrolidinium salts, and still more preferably at least one selected from the group consisting of quaternary ammonium salts, quaternary imidazolium salts and quaternary pyrrolidinium salts may be used.

Examples of the quaternary ammonium salts that can be used in this preparation method include amyltriethylammonium bis(trifluoromethanesulfonyl)imide butyltrimethylammonium bis(trifluoromethanesulfonyl)imide, benzyl(ethyl) dimethylammonium bis(trifluoromethanesulfonyl)imide, cyclohexyltrimethylammonium bis(trifluoromethanesulfonyl)imide, diethyl(methyl)ppropylammonium bis(fluorosulfonyl)imide, diethyl(2-methoxyethyl)methylammonium bis(fluorosulfonyl)imide, ethyl(2-methoxyethyl) dimethylammonium bis(fluorosulfonyl)imide, ethyl(2-methoxyethyl) dimethylammonium bis(trifluoromethanesulfonyl)imide, ethyl(3-methoxypropyl)dimethylammonium bis(trifluoromethanesulfonyl)imide, ethyl(dimethyl) (2-phenylethyl) ammonium bis(trifluoromethanesulfonyl)imide, methyltri-n-octylammonium bis(trifluoromethanesulfonyl)imide, tetrabutylammonium bromide, tetrabutylammonium chloride, tetrabutylammonium iodide, tetrabutylammonium tetrafluoroborate, tetrahexylammonium iodide, tetraamylammonium iodide, tetra-n-octylammonium iodide, tetrabutylammonium hexafluorophosphate, tetraheptylammonium iodide, tetraamylammonium bromide, tetraamylammonium chloride, tetrabutylammonium trifluoromethanesulfonate, tetrahexylammonium bromide, tetraheptylammonium bromide, tetra-n-octylammonium bromide, tetrapropylammonium chloride, tributylmethylammonium bis(trifluoromethanesulfonyl)imide, tetrabutylammonium acetate, trimethylpropylammonium bis(trifluoromethanesulfonyl)imide, tributyl(methyl)ammonium dicyanamide, tetrabutylammonium p-toluenesulfonate, and tributylmethylammonium iodide.

Examples of the quaternary ammonium salt that can be used in this preparation method include tetra $C_{1-18}$ alkyl ammonium salts (for example, tetra $C_{1-18}$ alkyl ammonium chloride), tri $C_{1-18}$ alkyl (hydroxy $C_{1-18}$ alkyl) ammonium salt, and the like, wherein the $C_{1-18}$ alkyl may be same or different, preferably tetramethylammonium chloride, tetraethylammonium chloride, tetrapropylammonium chloride, tetrabutylammonium chloride, tetrabutylammonium bromide, dodecyltrimethyl ammonium chloride, choline chloride, N,N,N-trimethylbutan-1-aminochloride.

Examples of the quaternary imidazolium salt that can be used in this preparation method include 1-allyl-3-methylimidazolium chloride, 1-allyl-3-methylimidazolium bis(trifluoromethanesulfonyl)imide, 1-butyl-3-methylimidazolium bromide, 1-butyl-3-methylimidazolium chloride, 1-butyl-3-methylimidazolium tetrafluoroborate, 1-butyl-3-methylimidazolium hexafluorophosphate, trifluoromethanesulfonic acid 1-butyl-3-methylimidazolium, 1-butyl-2,3-dimethylimidazolium chloride, 1-butyl-2,3-dimethylimidazolium hexafluorophosphate, 1-butyl-2,3-dimethylimidazolium tetrafluoroborate, 1-butyl-3-methylimidazolium bis(trifluoromethanesulfonyl)imide, 1-butyl-3-methylimidazolium tetrachloroferrate, 1-butyl-3-methylimidazolium iodide, 1-butyl-2,3-dimethylimidazolium bis(trifluoromethanesulfonyl)imide, 1-butyl-3-methylimidazolium methanesulfonate, 1-butyl-3-methylimidazolium trifluoro(trifluoromethyl)borate, 1-butyl-3-methylimidazolium tribromide, 1-butyl-3-methylimidazolium thiocyanate, 1-butyl-2,3-dimethylimidazolium trifluoromethane sulfonate, 3,3'-(butane-1,4-diyl) bis(1-vinyl-3-imidazolium) bis(trifluoromethanesulfonyl)imide, 1-butyl-3-methylimidazolium disianamide, 1-butyl-3-methylimidazolium tricyanomethanide, 1-butyl-3-methylimidazolium trifluoroacetate, 1-butyl-3-methylimidazoliummethyl sulfate, 1-benzyl-3-methylimidazolium chloride, 1-butyl-3-methylimidazolium hydrogen sulfate, 1-butyl-3-methylimidazolium dibutyl phosphate, 1-butyl-3-methylimidazolium hexafluoroantimonate, 1-benzyl-3-methylimidazolium tetrafluoroborate, 1-benzyl-3-methylimidazolium hexafluorophosphate, 1,3-dimethylimidazolium dimethyl phosphate, 1,3-dimethylimidazolium chloride, 1,2-dimethyl-3-propylimidazolium iodide, 2,3-dimethyl-1-propylimidazolium bis(trifluoromethanesulfonyl)imide, 1-decyl-3-methylimidazolium bis(trifluoromethanesulfonyl)imide, 1,3-dimethylimidazolium iodide, 1,3-dimethylimidazolium methylsulfate, 1,3-dimethylimidazolium bis(trifluoromethanesulfonyl)imide, 1-decyl-3-methylimidazolium bromide, 1-decyl-3-methylimidazolium chloride, 1-dodecyl-3-methylimidazolium bromide, 1-decyl-3-methylimidazolium tetrafluoroborate, 1-dodecyl-3-methylimidazolium bis(trifluoromethanesulfonyl)imide, 1-ethyl-3-methylimidazolium chloride, 1-ethyl-3-methylimidazolium hexafluorophosphate, 1-ethyl-3-methylimidazolium trifluoromethanesulfonate, 1-ethyl-3-methylimidazolium tetrafluoroborate, 1-ethyl-3-methylimidazolium bromide, 1-ethyl-3-methylimidazolium iodide, 1-ethyl-3-methylimidazolium bis(trifluoromethanesulfonyl)imide, 1-ethyl-3-methyl imidazolium ethyl sulfate, 1-ethyl-3-methylimidazolium p-toluenesulfonate, 1-ethyl-3-methylimidazolium dicyanamide, 1-ethyl-3-methylimidazolium tetrachloroferrate, 1-ethyl-2,3-dimethylimidazolium bis(trifluoromethanesulfonyl)imide, 1-ethyl-3-methylimidazolium hydrogen sulfate, 1-ethyl-3-methylimidazolium methanesulfonate, 1-ethyl-3-methylimidazolium nitrate, 1-ethyl-3-methylimidazolium thiocyanate, 1-ethyl-3-methylimidazolium trifluoro(trifluoromethyl)borate, 1-ethyl-3-methylimidazolium acetate, 3-ethyl-1-vinylimidazolium bis(trifluoromethanesulfonyl)imide, 1-ethyl-3-methylimidazolium tricyanomethanide, 1-ethyl-3-methylimidazolium trifluoroacetate, 1-ethyl-3-methylimidazolium methylsulfate, 1-ethyl-3-methylimidazolium diethylphosphate, 1-hexyl-3-methylimidazolium chloride, 1-hexyl-3-methylimidazolium hexafluorophosphate, 1-hexyl-3-methylimidazolium tetrafluoroborate, 1-hexyl-3-methylimidazolium trifluoromethanesulfonate, 1-hexyl-3-methylimidazolium bromide, 1-(2-hydroxyethyl)-3-methylimidazolium chloride, 1-hexyl-2,3-dimethylimidazolium iodide, 1-hexyl-3-methylimidazolium bis(trifluoromethanesulfonyl)imide, 1-(2-hydroxyethyl)-3-methylimidazolium tetrafluoroborate, 1-hexyl-3-methylimidazolium iodide, 1-(2-hydroxyethyl)-3-methylimidazolium bis(trifluoromethanesulfonyl)imide, 1-methyl-3-propylimidazolium iodide, 1-methyl-3-N-octylimidazolium bromide, 1-methyl-3-N-octylimidazolium chloride, 1-methyl-3-N-octylimidazolium hexafluorophosphate, 1-methyl-3-N-octylimidazolium trifluoromethanesulfonate, 1-methyl-3-N-octylimidazolium tetrafluoroborate, 1-methyl-3-propylimidazolium bromide, 1-methyl-3-propylimidazolium chloride, 1-methyl-3-propylimidazolium tetrafluoroborate, 1-methyl-3-pentylimidazolium bromide, 1-methyl-3-N-octyl imidazolium bis(trifluoromethanesulfonyl)imide, 1-methyl-3-propylimidazolium bis(trifluoromethanesulfonyl)imide, 1-methyl-3-(4-sulfobutyl)imidazolium bis(trifluoromethanesulfonyl)imide, 1-methyl-3-(4-sulfobutyl)imidazolium hydrogen sulfate, and 1-methylimidazole, and preferably 1-ethyl-3-methylimidazolium chloride, 1-methyl-3-N-octylimidazolium chloride.

Examples of the quaternary imidazolium salt that can be used in this preparation method include 1-$C_{1-18}$ alkyl-3-$C_{1-18}$ alkylimidazolium chloride, 1-$C_{1-18}$ alkyl-3-N—$C_{1-18}$ alkylimidazolium chloride, preferably 1-ethyl-3-methylimidazolium chloride and 1-methyl-3-N-octylimidazolium chloride.

Examples of the quaternary phosphonium salt that can be used in this preparation method include tetra $C_{1-18}$ alkyl phosphonium salts, tri $C_{1-18}$ alkyl (hydroxy $C_{1-18}$ alkyl) phosphonium salts, wherein $C_{1-18}$ alkyl may be same or different, preferably trihexyltetradecylphosphonium chloride.

Examples of the quaternary pyridinium salt that can be used in this preparation method include 1-$C_{1-18}$ alkylpyridinium salts, preferably 1-ethylpyridinium bromide, 1-ethylpyridinium chloride, 1-butylpyridinium chloride.

Examples of the quaternary pyrrolidinium salt that can be used in this preparation method include 1-allyl-1-methylpyrrolidinium bis(trifluoromethanesulfonyl)imide, 1-butyl-1-methylpyrrolidinium bis(trifluoromethanesulfonyl)imide, 1-butyl-1-methylpyrrolidinium chloride, 1-butyl-1-methylpyrrolidinium bromide, 1-butyl-1-methylpyrrolidinium bis(fluorosulfonyl)imide, 1-butyl-1-methylpyrrolidinium disianamide, 1-butyl-1-methylpyrrolidinium trifluoromethanesulfonate, 1-butyl-1-methylpyrrolidinium hexafluorophosphate, 1-ethyl-1-methylpyrrolidinium tetrafluoroborate, 1-ethyl-1-methylpyrrolidinium bromide, 1-methyl-1-propylpyrrolidinium bis(trifluoromethanesulfonyl)imide, 1-methyl-1-propylpyrrolidinium bis(fluorosulfonyl)imide, 1-(2-methoxyethyl)-1-methylpyrrolidinium bis(fluorosulfonyl)imide, 1-methyl-1-N-octylpyrrolidinium bis(trifluoromethanesulfonyl)imide, and 1-methyl-1-pentylpyrrolidinium bis(trifluoromethanesulfonyl)imide, and preferably 1-butyl-1-methylpyrrolidinium chloride.

Examples of the quaternary pyrrolidinium salt that can be used in this preparation method include 1-$C_{1-18}$ alkyl-1-$C_{1-}$ 18 alkylpyrrolidinium chloride, wherein $C_{1-18}$ alkyl may be same or different, preferably 1-butyl-1-methylpyrrolidium chloride.

Examples of the reaction accelerator that can be used in this preparation method include at least one selected from the group consisting of:

tetramethylammonium chloride,
tetraethylammonium chloride,
tetrapropylammonium chloride,
tetrabutylammonium chloride,
tetrabutylammonium bromide,
dodecyltrimethylammonium chloride,
trioctylmethylammonium chloride,
N,N,N-trimethylbutan-1-aminochloride,
1-ethylpyridinium bromide,
1-ethylpyridinium chloride,
1-butylpyridinium chloride,
1-ethyl-3-methylimidazolium chloride,
1-methyl-3-N-octylimidazolium chloride,
1-butyl-1-methylpyrrolidinium chloride, and
trihexyltetradecylphosphonium chloride.

In one embodiment, preferred reaction accelerators that can be used in this preparation method include tetra $C_{1-18}$ alkylammonium chloride, 1-$C_{1-18}$ alkyl-1-$C_{1-18}$ alkylpyrrolidinium chloride, 1-$C_{1-18}$ alkyl-3-$C_{1-18}$ alkylimidazolium chloride, preferably one selected from the group consisting of tetrabutylammonium chloride, 1-butyl-1-methylpyrrolidinium chloride and 1-methyl-3-N-octylimidazolium chloride.

The amount of the reaction accelerator that can be used in this preparation method is in the range of 1 to 100 times, preferably 1 to 50 times, still more preferably 1.5 to 20 times, in molar ratio per 1 mol of the compound [A].

The reaction temperature is, for example, suitably in the range of −78° C. to 130° C., preferably in the range of −40° C. to 100° C., and further preferably in the range of 0° C. to 80° C.

The reaction time is different depending on the type of the compound [A] to be used, the type of the compound [B] to be used, the type of the reaction solvent to be used, the type of the base to be used, and the reaction temperature, but is, for example, suitably in the range of 1 minute to 300 minutes, and preferably in the range of 5 minutes to 120 minutes.

When the compound [C], which is an oligonucleic acid compound, can be prepared, this preparation method can be applied to both a batch method and a flow method.

Moreover, this preparation method can also be applied to a solid-phase method and a liquid-phase method that are known as preparation methods for an oligonucleic acid compound, and a liquid-phase method using a hydrophobic group-binding nucleoside, a pseudo-solid phase-protected nucleoside, or the like.

When the compound [C], which is an oligonucleic acid compound, can be prepared by using the solid-phase method, the compound [A] supported on a solid-phase carrier at the oxygen atom at the 3'-position of the 3'-terminal nucleoside unit of the compound [A] or at the oxygen atom at the 5'-position of the 5'-terminal nucleoside unit of the compound [A], can be used.

When the oligonucleic acid compound can be prepared by using the liquid-phase method, the compound [A] supported on a soluble polymer soluble in an organic solvent at the oxygen atom at the 3'-position of the 3'-terminal nucleoside unit of the compound [A] or at the oxygen atom at the 5'-position of the 5'-terminal nucleoside unit of the compound [A], can be used.

When the oligonucleic acid compound can be prepared by using the liquid-phase method using a hydrophobic group-binding nucleoside, a pseudo-solid phase-protected nucleoside, or the like, the compound [A] having, for example, a hydrophobic group bound or supported on a pseudo-solid phase at the oxygen atom at the 3'-position of the 3'-terminal nucleoside unit of the compound [A] or at the oxygen atom at the 5'-position of the 5'-terminal nucleoside unit of the compound [A], can be used (see, for example, JP2010-275254 and WO 2012/157723).

Hereinafter, a detailed description is given with the compound [C-1] and the compound [C-2] as examples.

(E-1) Preparation Method for Compound [C-1]

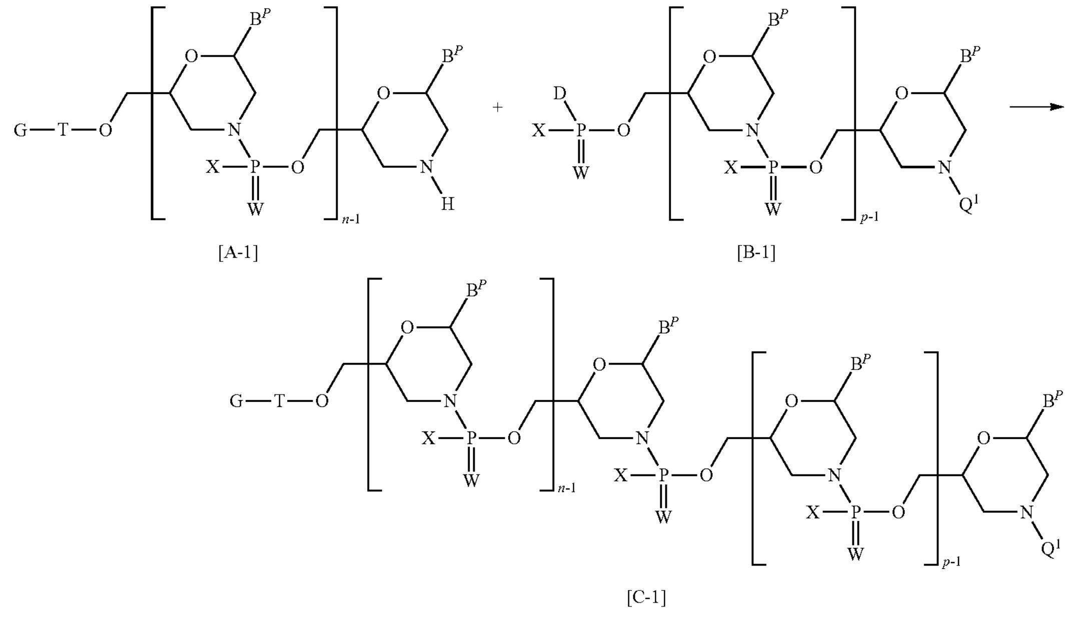

[A-1] [B-1]

[C-1]

wherein n, p, $B^P$, D, G, $Q^1$, T, W, and X are as defined above.

The compound "C-1" can be prepared by subjecting the compound [A-1] to a condensation reaction with the compound [B-1].

The solvent that can be used in this preparation method is not limited so long as it is a solvent generally used in the art, and a single solvent may be used, or two or more solvents may be used in combination. Examples of the solvent include aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane; and the like. These solvents may be used in combination.

Examples of the solvent that can be used in this preparation method include polar solvents, halogen-based solvents and the like.

Examples of the polar solvent that can be used in this preparation method include dimethylacetamide, dimethylsulfoxide, dimethylformamide, sulfolane, N-methylpiperidone, 1,3-dimethyl-2-imidazolidinone, N,N'-dimethylpropylene urea, and mixed solvents thereof. Among them, dimethylacetamide, dimethylsulfoxide, N-methylpiperidone, 1,3-dimethyl-2-imidazolidinone, and N,N'-dimethylpropylene urea are preferable.

Examples of the halogen-based solvent that can be used in this preparation method include chloroform, dichloromethane, 1,1-dichloroethane, 1,2-dichloroethane, 1,1,2-trichloroethane, 1,2-dichloroethylene, and mixed solvents thereof. Among them, chloroform, dichloromethane, 1,1-dichloroethane, and 1,2-dichloroethane are preferable.

As for the proportion of the polar solvent in the mixed solvent containing the polar solvent and the halogen-based solvent that can be used in this preparation method, the lower limit thereof is 1.0% by weight, preferably 2.0% by weight, more preferably 3.0% by weight, and further preferably 5.0% by weight. In addition, the upper limit thereof is 90% by weight, preferably 75% by weight, more preferably 50% by weight, further preferably 40% by weight, and particularly preferably 30% by weight. Furthermore, the upper limit and the lower limit can be used appropriately in combination, and the proportion of the polar solvent is, for example, suitably in the range of 1% to 90%, preferably in the range of 5% to 75%, and particularly preferably in the range of 5% to 50%.

In this preparation method, a base may be used if necessary. Examples of the "base" that can be used in this preparation method include diisopropylamine, N,N-diisopropylethylamine, triethylamine, N-ethylmorpholine, and 2,6-lutidine.

The amount of the base that can be used in this preparation method is, for example, suitably in the range of 1 mole to 100 moles, preferably in the range of 1 mole to 10 moles, and further preferably in the range of 1 mole to 5 moles, per mole of the compound [A].

In this preparation method, an additive may be used if necessary. Examples of the "additive" that can be used in this preparation method include LiBr, LiCl, LiI, and NaI are preferable.

The amount of the additive that can be used in this preparation method is, for example, suitably in the range of 0.2 moles to 6.0 moles, preferably in the range of 0.4 moles to 3.0 moles, and further preferably in the range of 1.0 mole to 2.5 moles, per mole of the compound [A].

The reaction temperature is, for example, suitably in the range of −78° C. to 130° C., preferably in the range of −40° C. to 100° C., and further preferably in the range of 0° C. to 80° C.

The reaction time is different depending on the type of the compound [A] to be used, the type of the compound [B] to be used, the type of the reaction solvent to be used, the type of the base to be used, and the reaction temperature, but is, for example, suitably in the range of 1 minute to 300 minutes, and preferably in the range of 5 minutes to 120 minutes.

In the case where the compound [A-1] has a solid-phase carrier in a molecule thereof, that is, in the case where G is the substituent [7] and Z is a solid-phase carrier in the compound [A-1], this condensation reaction can be carried out, for example, by (1) filling the compound [A-1] in a suitable column and eluting a reaction solution containing the compound [B-1], or (2) shaking or stirring a reaction solution containing the compound [A-1] and the compound [B-1] in a reaction vessel with a filter.

In the case where G is (1) a silyl substituent, (2) long-chain alkyl-carbonyl, (3) benzoyl substituted with 1 to 5 long-chain alkyloxy and/or long-chain alkenyloxy, or (4) the substituent [7] in the compound [A-1] (however, except for the case where Z is a solid-phase carrier), this condensation reaction can be carried out, for example, by (1) stirring the compound [A-1] and the compound [B-1] in a reaction solvent in a suitable reaction vessel or (2) independently supplying a solution containing the compound [A-1] and a solution containing the compound [B-1] to the inside of a flow reactor or a reaction channel via a flow channel and mixing these solutions in the flow reactor or the like.

The "flow channel", as used herein, means a channel for continuously supplying a solution, the "reaction channel" means a channel that allows a reaction to be carried out while allowing a solution to flow therethrough, and the flow reactor means a reactor with which operations are continuously performed such that input of a solution, a reaction, and collection of a product are performed simultaneously.

Examples of a method for supplying the solution containing the compound [A-1] and the solution containing the compound [B-1] to the flow channel include a pump for supplying a liquid, which is usually used in this field, and specific examples of such a method include a syringe pump, a plunger pump, a diaphragm pump, and a gear pump.

Examples of the flow reactor include in-line mixers such as a microreactor and a static mixer.

An example of a method for guiding the solution containing the compound [A-1] and the solution containing the compound [B-1] from the flow channel to the reaction channel is a multi-stage collision type micromixer.

Examples of the materials of the flow channel and the reaction channel include tubes made of a synthetic resin selected from the group consisting of fluorine resins such as perfluoroalkoxy alkane (PFA), vinyl chloride resins, polyamide resins, and aromatic polyetherketone resins, and pipes made of a metal selected from the group consisting of stainless steel, copper, an alloy thereof, titanium, and an alloy thereof.

Each of the inner diameters of the flow channel and the reaction channel may be normally selected, for example, from among sizes in the range of 0.1 mm to 1.0 mm, and is preferably selected, for example, from among sizes in the range of 0.2 mm to 1.0 mm.

(E-2) Preparation Method for Compound [C-2]

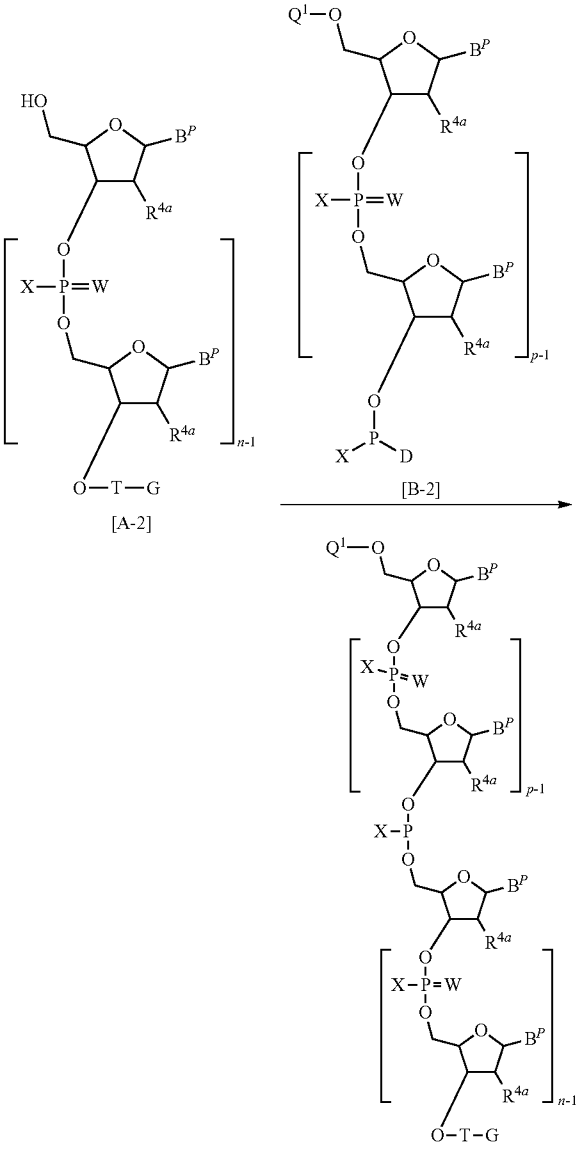

[A-2] [B-2] [C-2]

wherein n, p, $B^P$, D, G, $Q^1$, $R^{4a}$, T, W, and X are as defined above.

The compound "C-2" can be prepared by subjecting the compound [A-2] to a condensation reaction with the compound [B-2].

In this preparation method, a base may be used if necessary. Examples of the "base" that can be used in this preparation method include diisopropylamine, N,N-diisopropylethylamine, triethylamine, N-ethylmorpholine, and 2,6-lutidine.

In the case where the compound [A-2] has a solid-phase carrier in a molecule thereof, that is, in the case where G is the substituent [7] and Z is a solid-phase carrier in the compound [A-2], this condensation reaction can be carried out, for example, by (1) filling the compound [A-1] in a suitable column and eluting a reaction solution containing the compound [B-2], or (2) shaking or stirring a reaction solution containing the compound [A-2] and the compound [B-2] in a reaction vessel with a filter.

In the case where G is (1) a silyl substituent, (2) long-chain alkyl-carbonyl, (3) benzoyl substituted with 1 to 5 long-chain alkyloxy and/or long-chain alkenyloxy, or (4) the substituent [7] in the compound [A-2] (however, except for the case where Z is a solid-phase carrier), this condensation reaction can be carried out, for example, by (1) stirring the compound [A-2] and the compound [B-2] in a reaction solvent in a suitable reaction vessel or (2) independently supplying a solution containing the compound [A-2] and a solution containing the compound [B-2] to the inside of a flow reactor or a reaction channel via a flow channel and mixing these solutions in the flow reactor or the like.

Furthermore, after the condensation reaction, the compound [C-2] can be obtained by (1) purification from the reaction mixture using a column, or (2) adding a suitable solvent to the reaction mixture, collecting the obtained precipitate by filtration, and washing the precipitate with a suitable solvent.

The compound "C-2", which is a compound of which nucleoside units are the nucleoside units [4a] and the nucleoside units [4e], can be prepared by the same method as described above, even if the compound "C-2" is a compound in which all or a part of the nucleoside units [4a] or the nucleoside units [4e] is replaced by the nucleoside unit [4b], the nucleoside unit [4c], the nucleoside unit [4f], or the nucleoside unit [4g].

(F) Purification Method for Compound [C]

In the case where the compound [C] has a substituent exhibiting very high lipophilicity in a molecule thereof, the compound [C] can be easily isolated and purified merely by crystallization or extraction operation without requiring complicated operations such as column purification.

Examples of such a compound include compounds that are the compound [C-1] and the compound [C-2] in each of which G is (1) long-chain alkyl-carbonyl, (2) benzoyl substituted with 1 to 5 long-chain alkyloxy and/or long-chain alkenyloxy, or (3) the substituent [7] (however, except for the case where Z is a solid-phase carrier).

In the case where the compound [C] has a solid-phase carrier in a molecule thereof, the compound [C] can be purified, for example, by filling the compound [C] in a suitable column and washing the compound [C] using a suitable solvent to remove unnecessary substances.

Examples of such a compound include compounds that are the compound [C-1] and the compound [C-2] in each of which G is the substituent [7] and Z is a solid-phase carrier.

Moreover, in the case where G is a silyl substituent in the compound [C-1] or the compound [C-2], the target compound can be isolated and purified by performing operations such as column purification using a suitable solvent.

(G) Method for Removing $Q^1$ in Molecule of Compound [C]

In the case where the compound [C] is a compound containing two or more nucleoside units, the compound [C] may have a hydroxyl group or a primary or secondary amino group protected by a removable group under an acidic condition, in a molecule thereof.

In such a case, the compound [C] in which the number of nucleoside units is increased by one can be prepared by carrying out the condensation reaction described above in "(E) Preparation method for compound [C]", on a new compound prepared by selectively removing the removable group under an acidic condition in the molecule.

Hereinafter, a detailed description is given with the compound [C-1] and the compound [C-2] as examples.

(G-1) Method for Removing $Q^1$ in Molecule of Compound [C-1]

$Q^1$ substituted at the nitrogen atom at the 3'position of the 3'-terminal nucleoside unit of the compound [C-1] can be removed by reacting the compound [C-1] with an acid. A compound represented by the following general formula [E-1](hereinafter, referred to as "compound [E-1]") can be prepared by removing $Q^1$ in the molecule of the compound [C-1].

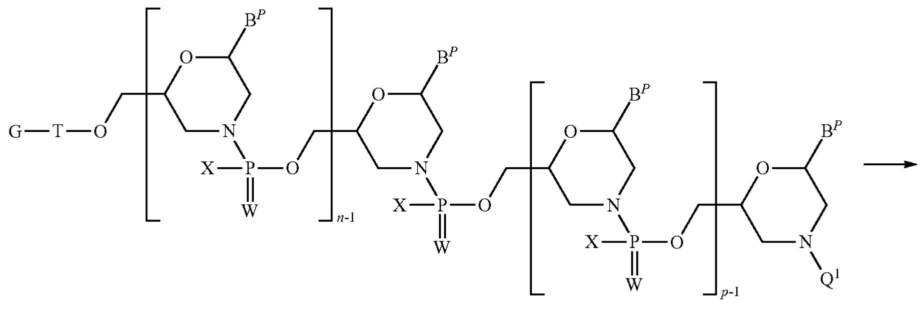

[C-1]

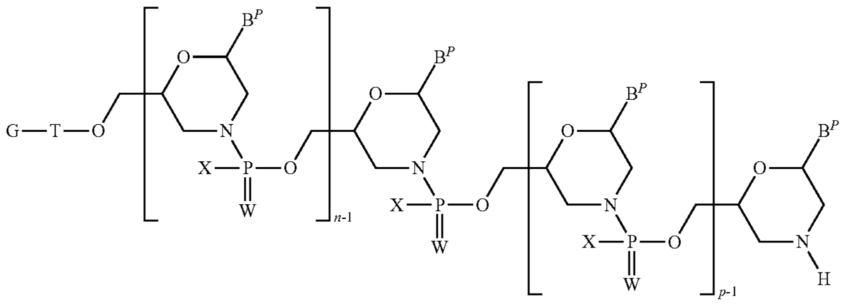

[E-1]

wherein n, p, $B^P$, G, $Q^1$, T, W, and X are as defined above.

In one embodiment, before removing the $Q^1$ substituent on the oxygen atom at the 5'position of the nucleoside on the 5'-end of compound [C-1-1], the phosphorus atom on the phosphate bond, as formed in said condensation reaction, is firstly oxidized from trivalent to pentavalent using an oxidizing agent to convert into a compound of general formula [C-1] (Hereinafter Referred to as “compound [C-1]”)

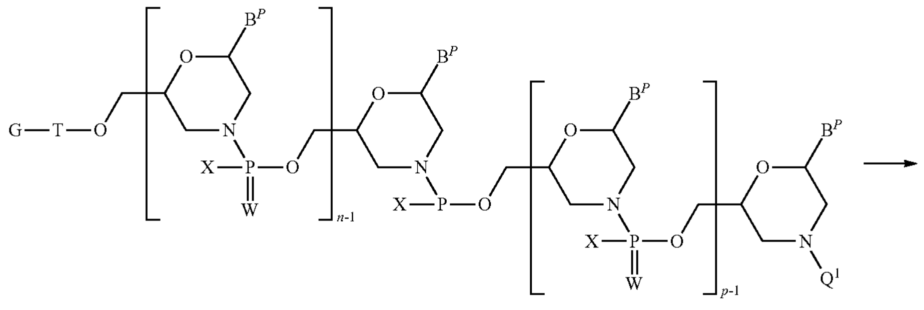

[C-1-1]

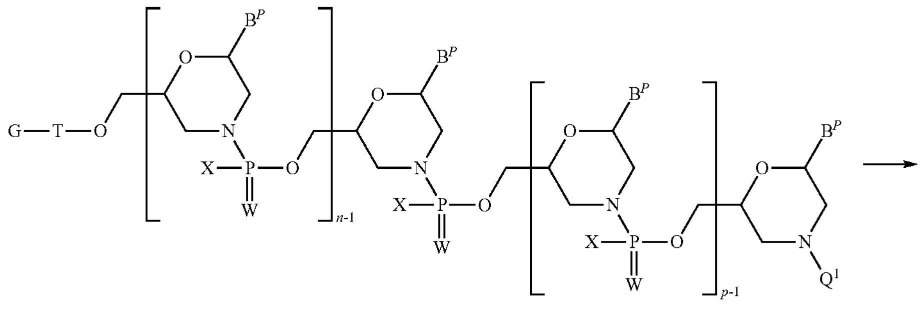

[C-1]

-continued

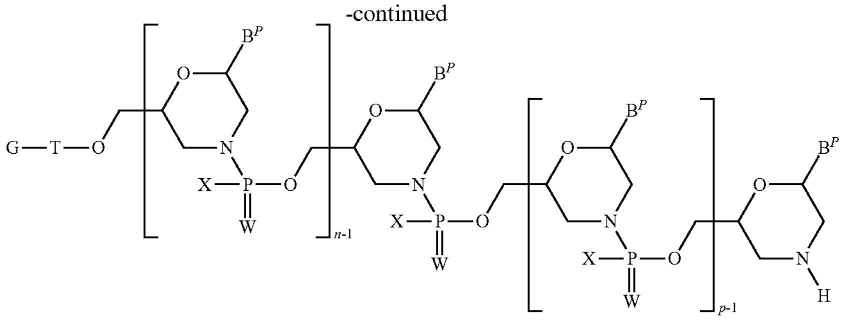

[E-1]

In the case where G is the substituent [7] and Z is a solid-phase carrier in the compound [C-1], this removal can be carried out, for example, by (1) filling the compound [C-1] in a suitable column and eluting a solution containing the acid, or (2) shaking or stirring a solution containing the compound [C-1] and the acid in a reaction vessel with a filter.

The solvent that can be used in this removal is not limited so long as it is a solvent generally used in the art, and a single solvent may be used, or two or more solvents may be used in combination. Examples of the solvent include aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like. These solvents may be used in combination.

Examples of the solvent that can be used in this removal include polar solvents, halogen-based solvents and the like.

The solvent that can be used for this removal is not particularly limited, but, for example, a mixed solvent containing a polar solvent and a halogen-based solvent can be used. As for the proportion of the polar solvent in the mixed solvent containing the polar solvent and the halogen-based solvent, the lower limit thereof is 1.0% by weight, preferably 2.0% by weight, more preferably 3.0% by weight, and further preferably 5.0% by weight. In addition, the upper limit thereof is 90% by weight, preferably 75% by weight, more preferably 50% by weight, further preferably 40% by weight, and particularly preferably 30% by weight. Furthermore, the upper limit and the lower limit can be used appropriately in combination, and the proportion of the polar solvent is, for example, suitably in the range of 1% to 50%, preferably in the range of 1% to 40%, and particularly preferably in the range of 1% to 30%.

Examples of the "acid" that can be used for this removal include trifluoroacetic acid, cyanopyridine trifluoroacetic acid salts, triethylamine trifluoroacetic acid salts, cyanoacetic acid, trichloroacetic acid, phosphoric acid, methanesulfonic acid, p-toluenesulfonic acid, and hydrochloric acid. When each of these acids is used, the acid may be used in combination with a base (for example, triethylamine) such that the acidity thereof is adjusted.

The amount of the acid that can be used for this removal is, for example, suitably in the range of 1 mole to 500 moles, and preferably in the range of 2 moles to 200 moles, per mole of the compound [C-1].

The acid that can be used for this removal is suitable to be diluted with a suitable solvent such that the concentration thereof is in the range of 5% to 80%, and is preferably diluted with a suitable solvent such that the concentration thereof is in the range of 5% to 50%.

The solvent for dissolving the acid that can be used for this removal is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

Moreover, a scavenger may be used if necessary for this removal.

Examples of the "scavenger" that can be used for this removal include ethanol, triisopropylsilane, 1-hydroxybenzotriazole, pyrrole, indole, 2,2,2-trifluoroethanol, methanol, anisole, mercaptoethanol, and thioanisole.

The amount of the scavenger that can be used for this removal is, for example, suitably in the range of 1 mole to 100 moles, and preferably in the range of 1 mole to 50 moles, per mole of the compound [C-1].

In the case where G is (1) a silyl substituent, (2) long-chain alkyl-carbonyl, (3) benzoyl substituted with 1 to 5 long-chain alkyloxy and/or long-chain alkenyloxy, or (4) the substituent [7] in the compound [C-1] (however, except for the case where Z is a solid-phase carrier), this removal can be carried out, for example, by (1) stirring the compound [C-1] and the acid in a suitable reaction solvent in a suitable reaction vessel or (2) independently supplying a solution containing the compound [C-1] and a solution containing the acid to the inside of a flow reactor or a reaction channel via a flow channel and mixing these solutions in the flow reactor or the like.

The solvent that can be used for this removal is not particularly limited, but, for example, a mixed solvent containing a polar solvent and a halogen-based solvent can be used. As for the proportion of the polar solvent in the mixed solvent containing the polar solvent and the halogen-based solvent, the lower limit thereof is 1.0% by weight, preferably 2.0% by weight, more preferably 3.0% by weight, and further preferably 5.0% by weight. In addition, the upper limit thereof is 90% by weight, preferably 75% by weight, more preferably 50% by weight, further preferably 40% by weight, and particularly preferably 30% by weight.

Furthermore, the upper limit and the lower limit can be used appropriately in combination, and the proportion of the polar solvent in the mixed solvent containing the polar solvent and the halogen-based solvent is, for example, suitably in the range of 1% to 50%, preferably in the range of 1% to 40%, and particularly preferably in the range of 1% to 30%.

Examples of the "acid" that can be used for this removal include the same as those described above. When each of these acids is used, the acid may be used in combination with a base (for example, triethylamine) such that the acidity thereof is adjusted.

The amount of the acid that can be used for this removal is, for example, suitably in the range of 1 mole to 500 moles, and preferably in the range of 2 moles to 200 moles, per mole of the compound [C-1].

The acid that can be used for this removal is suitable to be diluted with a suitable solvent such that the concentration thereof is in the range of 5% to 80%, and is preferably diluted with a suitable solvent such that the concentration thereof is in the range of 5% to 50%.

The solvent for dissolving the acid that can be used for this removal is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

Moreover, in this step, a scavenger may be used if necessary.

Examples of the "scavenger" that can be used for this removal include the same as those described above.

The amount of the scavenger that can be used for this removal is, for example, suitably in the range of 1 mole to 100 moles, and preferably in the range of 1 mole to 50 moles, per mole of the compound [C-1].

Examples of a method for supply to the flow channel that can be used for this removal include a pump for supplying a liquid, which is usually used in this field, and specific examples of such a method include a syringe pump, a plunger pump, a diaphragm pump, and a gear pump.

Examples of the flow reactor that can be used for this removal include in-line mixers such as a microreactor and a static mixer.

An example of a method for guiding from the flow channel to the reaction channel that can be used for this removal is a multi-stage collision type micromixer.

Examples of the materials of the flow channel and the reaction channel that can be used for this removal include tubes made of a synthetic resin selected from the group consisting of fluorine resins such as perfluoroalkoxy alkane (PFA), vinyl chloride resins, polyamide resins, and aromatic polyetherketone resins, and pipes made of a metal selected from the group consisting of stainless steel, copper, an alloy thereof, titanium, and an alloy thereof.

Each of the inner diameters of the flow channel and the reaction channel that can be used for this removal may be normally selected, for example, from among sizes in the range of 0.1 mm to 1.0 mm, and is preferably selected, for example, from among sizes in the range of 0.2 mm to 1.0 mm.

As described in following Test Examples and Examples, in a method for producing the compound [E-1], removal of $Q^1$ can be carried out in situ as this continuous reaction by adding a solution containing an acid to a reaction mixture containing the compound [C-1], which is prepared by subjecting the compound [A-1] and the compound [B-1] to a condensation reaction, using a reaction accelerator. In addition, in the method for producing the compound [C-1], this continuous reaction can be carried out by removing $Q^1$ of a compound [A-1-1] using a reaction accelerator and subjecting the compound [A-1] and the compound [B-1] to a condensation reaction in situ to form the compound [C-1].

The solvent that can be used in this continuous reaction is not limited so long as it is a solvent generally used in the art, and a single solvent may be used, or two or more solvents may be used in combination. Examples of the solvent include aromatic solvents such as benzene, toluene, xylene, mesitylene and the like; ester solvents such as ethyl acetate, isopropyl acetate and the like; aliphatic solvents such as hexane, pentane, heptane, octane, nonane, cyclohexane and the like. These solvents may be used in combination.

Examples of the solvent that can be used in this continuous reaction include polar solvents, halogen-based solvents and the like.

The solvent that can be used for this continuous reaction is not particularly limited, but, for example, a mixed solvent containing a polar solvent and a halogen-based solvent can be used. As for the proportion of the polar solvent in the mixed solvent containing the polar solvent and the halogen-based solvent, the lower limit thereof is 1.0% by weight, preferably 2.0% by weight, more preferably 3.0% by weight, and further preferably 5.0% by weight. In addition, the upper limit thereof is 90% by weight, preferably 75% by weight, more preferably 50% by weight, further preferably 40% by weight, and particularly preferably 30% by weight. Furthermore, the upper limit and the lower limit can be used appropriately in combination, and the proportion of the polar solvent in the mixed solvent containing the polar solvent and the halogen-based solvent is, for example, suitably in the range of 1% to 50%, preferably in the range of 1% to 40%, and particularly preferably in the range of 1% to 30%.

An example of this continuous reaction is a method which comprises: removing $Q^1$ from a compound of formula [A-1-1]:

[A-1-1]

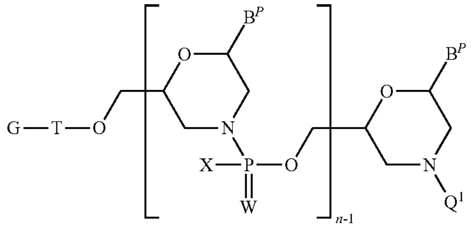

wherein $B^P$ is an optionally protected nucleic acid base, $Q^1$ is a removable group under an acidic condition, W is an oxygen atom or a sulfur atom, X is di($C_{1-6}$ alkyl)amino or selected from among substituents represented by general formulae [2-1] to [2-8]:

[2=1]

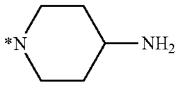

[2-2]

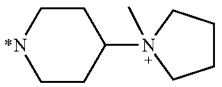

[2-3]

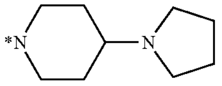

[2-4]

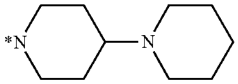

[2-5]

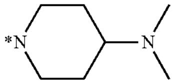

-continued

[2-6]

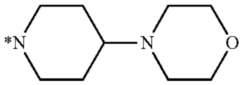

[2-7]

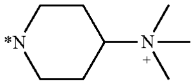

[2-8]

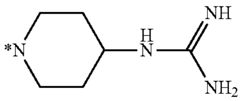

wherein * represents a binding position with a phosphorus atom, and X is preferably di($C_{1-6}$ alkyl)amino and further preferably dimethylamino, G represents a substituent represented by general formula [7]:

Z-L* [7]

wherein

* represents a binding position with T,

Z is a substituent represented by one of general formulae [8A] to [8D], [8E], [8G], [8H], [8J], [8K], and [8N]

[8A]

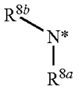

[8B]

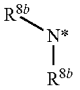

[8C]

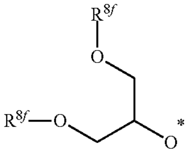

[8D]

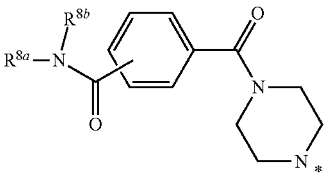

[8E]

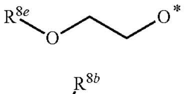

[8G]

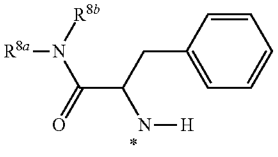

[8H]

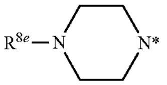

-continued

[8J]

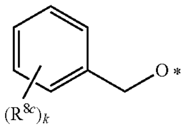

[8K]

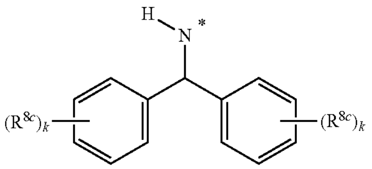

[8N]

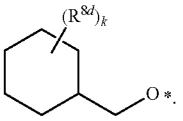

wherein

* represents a binding position with L, k represents an integer from 0 to 5, $R^{8a}$ represents a hydrogen atom or $C_{1-6}$ alkyl, $R^{8b}$ is the same or different and each represent long-chain alkyl, $R^{8c}$ is the same or different and each represent a substituent represented by the following general formula [9A]:

$*O—R^9$ [9A]

wherein

* represents a binding position, and $R^9$ represents long-chain alkyl and/or long-chain alkenyl, $R^{8d}$ is the same or different and each represent a hydrogen atom, a halogen, long-chain alkyl optionally substituted with 1 to 13 halogens, or long-chain alkyloxy optionally substituted with 1 to 13 halogens, $R^{8e}$ represents (1) long-chain alkyl, (2) long-chain alkyl-carbonyl, or (3) benzoyl substituted with 1 to 5 long-chain alkyloxy and/or long-chain alkenyloxy, and $R^{8f}$ represents (1) long-chain alkyl, (2) long-chain alkyl-carbonyl, or (3) long-chain alkenyl-carbonyl, and L represents a substituent represented by general formula [10]:

[10]

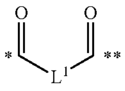

wherein

* represents a binding position with Z,

** represents a binding position with an oxygen atom, and $L^1$ represents an optionally substituted $C_{2-10}$ alkylene or an optionally substituted $C_{6-10}$ arylene, T is a single bond or a substituent represented by the following general formula [11]:

[11]

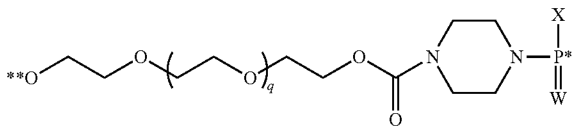

wherein

X and W are as defined above,

* represents a binding position with O,

** represents a binding position with G, and q represents an integer from 0 to 10, and n is 1 to 25, to form a compound of formula [A-1]:

[A-1]

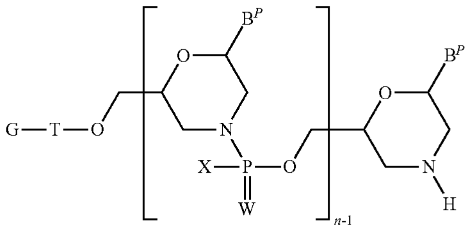

wherein $B^P$, W, X, G, T, and n are as defined above, and then reacting the compound of general formula [A-1] with a compound of formula [B-1]:

[B-1]

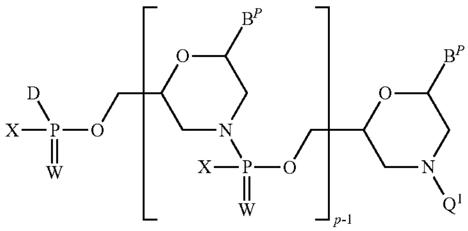

wherein $B^P$, $Q^1$, W, X, G, and T are as defined above,

D is a halogen, and p is an integer from 1 to 10, to obtain a compound of formula [C-1]

[C-1]

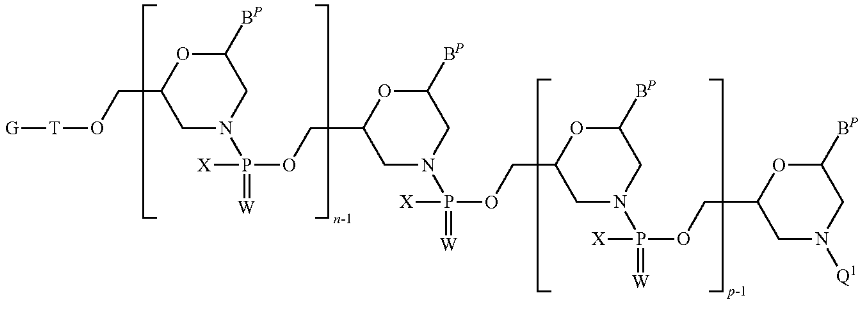

wherein n, p, $B^P$, $Q^1$, W, X, G, and T are as defined above, in the presence of a reaction accelerator.

This continuous reaction may comprises, for example, removing $Q^1$ from a compound of formula [A-1-1]

[A-1-1]

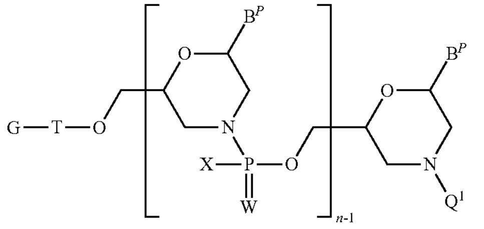

wherein $Q^1$ is trityl, monomethoxytrityl, or dimethoxytrityl, and n, $B^P$, W, X, G, and T are as defined above, in the presence of trifluoroacetic acid and 2,2,2-trifluoroethanol, and optionally triisopropylsilane or ethanol, in the presence of a reaction accelerator.

This continuous reaction can be carried out in a flow reactor. An example of this continuous reaction is a method that comprises supplying a solution containing the compound of general formula [A-1-1] and a solution containing an acid to a flow reactor to remove $Q^1$ to form the compound of formula [A-1], and supplying a solution containing the compound of general formula [A-1] and a solution containing the compound of general formula [B-1] to a subsequent flow reactor to obtain the compound of general formula [C-1].

Optionally, a flow reactor that supplies a solution containing the compound of formula [A-1] and a solution containing a scavenger, or a flow reactor that supplies a solution containing the compound of formula [B-1] in excess and the compound of the formula [C-1] and a solution containing at least one selected from the group consisting of morpholine, 1-methylpiperazine, and N-ethylmorpholine, can be used.

(G-2) Method for Removing $Q^1$ in Molecule of Compound [C-2]

The compound [C-2] is an unstable compound. Thus, preferably, before removing $Q^1$, which is substituted at the oxygen atom at the 5'-position of the 5'-terminal of the compound [C-2], from the compound [C-2], the phosphorus atom on the phosphorous bond formed by the condensation reaction is initially oxidized from trivalent to pentavalent using an oxidizing agent to convert the compound [C-2] to a compound represented by the following general formula [D-2](hereinafter, referred to as "compound [D-2]"):

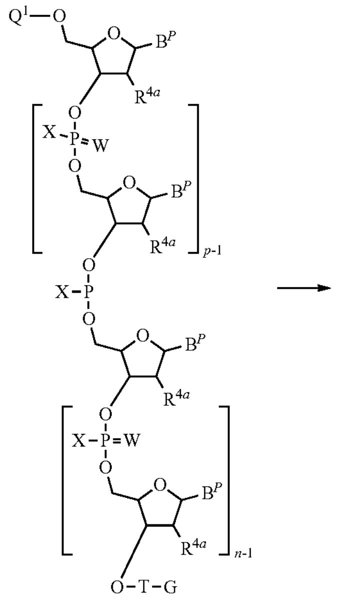

[C-2]

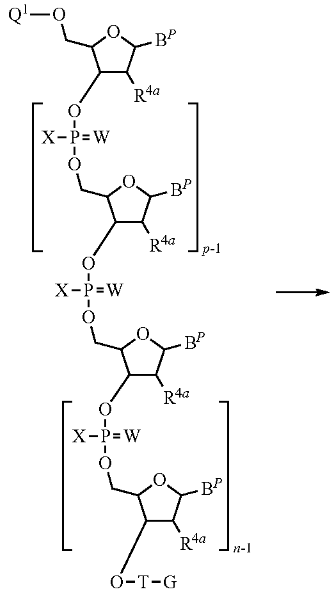

[D-2]

-continued

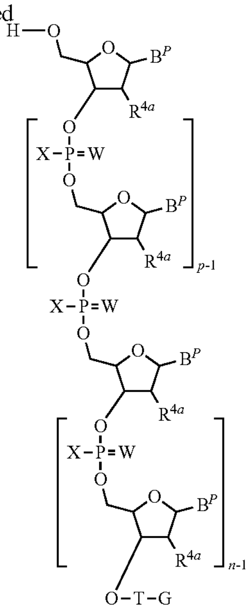

[E-2]

wherein n, p, $B^P$, G, $Q^1$, $R^{4d}$, T, W, and X are as defined above.

Step 1: Preparation of Compound [D-2]

In the case where G is the substituent [7] and Z is a solid-phase carrier in the compound [C-2], the oxidation reaction of the phosphorus atom can be carried out according to a known method (Current Protocols in Nucleic Acid Chemistry).

Examples of the oxidizing agent that can be used in this step include commercially available oxidizing solutions for nucleic acid synthesis [oxidizing solution-2, 0.1 mol/L iodine/78% tetrahydrofuran/20% pyridine/2% water, manufactured by FUJIFILM Wako Pure Chemical Industries, Ltd.; oxidizing solution, 0.5 M acetone solution of 0.5 M (1S)-(+)-(10-camphorsulfonyl)-oxaziridine, manufactured by Glen Research Corporation].

In addition, in the case of oxidizing the phosphorus atom for phosphorothioation, the oxidation reaction of the phosphorus atom can be carried out according to a known method (see, for example, Current Protocols in Nucleic Acid Chemistry).

Examples of the oxidizing agent that can be used in this step include commercially available sulfurizing reagents for nucleic acid synthesis [3-{(N,N-dimethylaminomethylidene)amino})-3H-1,2,4-dithiazole-5-thion (DDTT), manufactured by Glen Research Corporation; 5-phenyl-3H-1,2,4-dithiazole-3-one for nucleic acid synthesis, manufactured by FUJIFILM Wako Pure Chemical Industries, Ltd]. In this step, these oxidizing agents are suitable to be dissolved in a suitable solvent and used.

In the case where G is (1) a silyl substituent, (2) long-chain alkyl-carbonyl, (3) benzoyl substituted with 1 to 5 long-chain alkyloxy and/or long-chain alkenyloxy, or (4) the substituent [7] in the compound [C-2] (however, except for the case where Z is a solid-phase carrier), the oxidation reaction of the phosphorus atom can be carried out according to a known method (see, for example, Nucleic Acids Research, Vol. 21, No. 5, 1213-1217 (1993)).

Examples of the oxidizing agent that can be used in this step include (+)-camphorylsulfonyl oxaziridine (CSO), (+)-(8,8-dichlorocamphorylsulfonyl)-oxaziridine (DCSO), methyl ethyl ketone peroxide, and tert-butyl hydroperoxide (TBHP).

Step 2: Preparation of Compound [E-2]

$Q^1$ substituted at the oxygen atom at the 5'-position of the 5'-terminal nucleoside unit of the compound [D-2] can be removed by reacting the compound [D-2] with an acid. A compound represented by the above general formula [E-2] (hereinafter, referred to as compound [E-2]) can be prepared by removing $Q^1$ in the molecule of the compound [D-2] from the compound [D-2].

In the case where G is the substituent [7] and Z is a solid-phase carrier in the compound [D-2], the removal of $Q^1$ can be carried out, for example, by filling the compound [D-2] in a suitable column and eluting a solution containing the acid, or shaking or stirring a solution containing the compound [D-2] and the acid in a reaction vessel with a filter.

$Q^1$ in the molecule of the compound [D-2] can be removed according to a known method (see, for example, Current Protocols in Nucleic Acid Chemistry).

Examples of the acid that can be used in this step include commercially available deblocking solutions for nucleic acid synthesis [for example, deblocking solution-1, 3 w/v % trichloroacetic acid/dichloromethane solution (manufactured by Fujifilm Wako Pure Chemical Industries, Ltd.), Deblocking Mix 3% dichloroacetic acid/dichloromethane solution (manufactured by Glen Research Corporation)].

In the case where G is (1) a silyl substituent, (2) long-chain alkyl-carbonyl, (3) benzoyl substituted with 1 to 5 long-chain alkyloxy and/or long-chain alkenyloxy, or (4) the substituent [7] in the compound [D-2] (however, except for the case where Z is a solid-phase carrier), the removal of $Q^1$ can be carried out, for example, by (1) stirring the compound [D-2] and the acid in a suitable reaction solvent in a suitable reaction vessel or (2) independently supplying a solution containing the compound [D-2] and a solution containing the acid to the inside of a flow reactor or a reaction channel via a flow channel and mixing these solutions in the flow reactor or the like.

$Q^1$ in the molecule of the compound [D-2] can be removed according to a known method (see, for example, Nucleic Acids Research, Vol. 21, No. 5, 1213-1217 (1993)).

Examples of the acid that can be used in this step include dichloroacetic acid and trichloroacetic acid.

(H) Final Deprotection, Nucleic Acid Compound Isolation Step

In the case where the compound [C-1], the compound [D-2], the compound [E-1], or the compound [E-2] has a protective group in a molecule thereof, a compound in which all the protective groups are removed, and then can be prepared by performing a deprotection treatment corresponding to the type or properties of the protective group. All the protective groups of the compound can be removed, for example, according to the deprotection method described in "Green's PROTECTIVE GROUPS in ORGANIC SYNTHESIS, 4th Edition, 2006". Specifically, the protective groups for the substituent [6] and the amino group or the hydroxyl group of the nucleic acid base in the molecule of the compound [C-1], the compound [D-2], the compound [E-1], or the compound [E-2] can be removed, for example, by performing a treatment with (1) ammonia water, (2) ammonia water/ethanol, or (3) a mixed solution containing ammonia water and a methylamine aqueous solution.

In addition, the protective group for the amino group at the 3'-position of the 3'-terminal nucleoside of the compound [C-1] and the removable group under an acidic condition that is substituted at the hydroxyl group at the 5'-position of the 5'-terminal nucleoside of the compound [D-2], can be removed, for example, by performing a treatment with an acid that is the same as the "acid" described above in "Method for removing $Q^1$ in molecule of compound [C-1]", an acid that is the same as the "acid" described above in "Step 2: Preparation of compound [E-2]" in "Method for removing $Q^1$ in molecule of compound [C-2]", or a solution obtained by diluting hydrochloric acid or acetic acid with a suitable solvent.

In the case of removing the removable group under an acidic condition that is substituted at the hydroxyl group at the 5'-position of the 5'-terminal nucleoside of the compound [D-2] after the protective group for the nucleic acid base moiety is removed, a solution obtained by diluting an acid with water is used. In the case where the nucleic acid base moiety is protected, a solution obtained by diluting an acid with a suitable organic solvent is used.

(I) Purification and Separation Step

The compound in which all the protective groups of the compound [C-1] or the compound [E-1] are removed, and then can be isolated from a reaction mixture by usual separation and purification method, for example, by using method such as extraction, concentration, neutralization, filtration, centrifugation, recrystallization, C8 to C18 reverse phase column chromatography, cation exchange column chromatography, anion exchange column chromatography, gel filtration column chromatography, high performance liquid chromatography, dialysis, and ultra-filtration, alone or in combination (see, for example, WO1991/09033A1).

In the case of purifying the target compound using reverse phase chromatography, for example, a mixed solution containing 20 mM triethylamine/acetate buffer and acetonitrile can be used as an elution solvent.

In the case of purifying the desired compound using ion exchange chromatography, for example, a mixed solution containing a 1 M solution of NaCl and a 10 mM aqueous solution of sodium hydroxide, or a 0.3 M NaCl solution in 50 mM phosphate buffer can be used.

The compound in which all the protective groups of the compound [D-2] or the compound [E-2] are removed, and then can be isolated from the reaction mixture by usual separation and purification method, for example, by using method such as extraction, concentration, neutralization, filtration, centrifugation, recrystallization, C8 to C18 reverse phase column chromatography, C8 to C18 reverse phase cartridge column, cation exchange column chromatography, anion exchange column chromatography, gel filtration column chromatography, high performance liquid chromatography, dialysis, and ultra-filtration, alone or in combination.

Examples of the "elution solvent" include single solvents such as acetonitrile, methanol, ethanol, isopropyl alcohol, and water, and mixed solvents containing these solvents at any ratios. In this case, the pH of the solution can be adjusted in the range of 1 to 9 by adding, as an additive, for example, sodium phosphate, potassium phosphate, sodium chloride, potassium chloride, ammonium acetate, triethylammonium acetate, sodium acetate, potassium acetate, tris hydrochloric acid, or ethylenediamine tetraacetic acid at a concentration of 1 mM to 2 M.

(J) Preparation of Compound [A]

The compound [A] is prepared, for example, by introducing the substituent [6] into a hydroxyl group of a compound corresponding to the compound [A] according to a known method.

Hereinafter, the preparation method for the compound [A] is described by introducing typical examples.

(J-1) Preparation of Compound [A-1]

The compound [A] comprising one or more nucleoside units [4d] and in which the phosphate bond between each nucleoside unit is the phosphate bond [5], can be prepared, for example, according to methods described in (i) to (iv) below.

(i) Preparation of Compound [A-1] in which G is a Silyl Substituent and T is a Single Bond

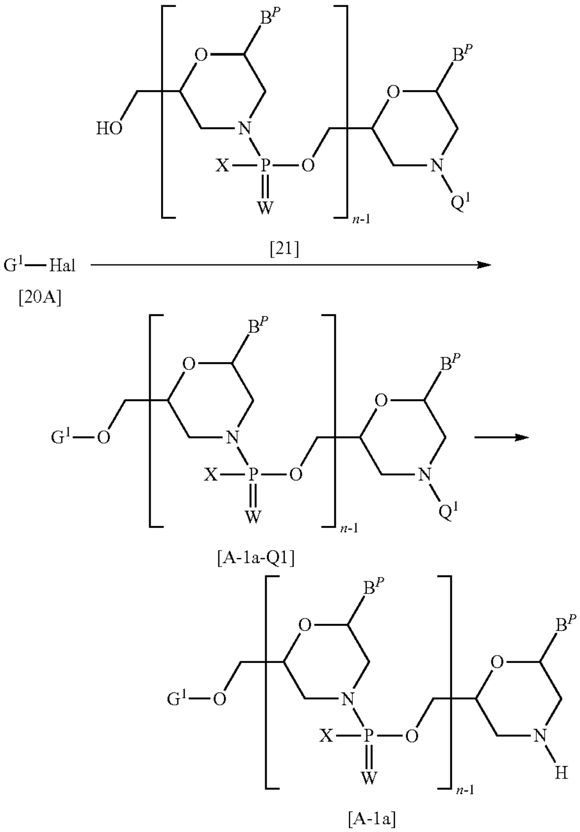

wherein n, $B^P$, $Q^1$, X, and W are as defined above,

Hal represents a halogen, and $G^1$ represents a silyl substituent.

A compound represented by the above general formula [A-1a] (hereinafter, referred to as "compound [A-1a]") is the compound [A-1] in which G is a silyl substituent and T is a single bond.

Hereinafter, an example of a preparation method for the compound [A-1a] is described.

Step 1: Preparation of Compound Represented by Above General Formula [A-1a-Q1] (Hereinafter, Referred to as "Compound [A-1a-Q1]")

The compound [A-1a-Q1] can be prepared by using a compound represented by the above general formula [20A] (hereinafter, referred to as "compound [20A]") on a compound represented by the above general formula [21] (hereinafter, referred to as "compound [21]") and introducing a silyl substituent to the 5'-terminal hydroxyl group of the compound [21]. The introduction reaction of the silyl substituent can be carried out according to a known method.

Step 2: Preparation of Compound [A-1a]

The compound [A-1a] can be prepared by treating the compound [A-1a-Q1] with an acid.

Examples of the "acid" that can be used in this step include the same "acids" described above in "Method for removing $Q^1$ in molecule of compound [C-1]".

The amount of the acid that can be used in this step is, for example, suitably in the range of 1 mole to 500 moles, and preferably in the range of 2 moles to 200 moles, per mole of the compound [A-1a-Q1], The acid that can be used in this step may be diluted with a suitable solvent, and such as solvent is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

In this step, a scavenger may be used if necessary.

Examples of the "scavenger" that can be used in this step include the same "scavengers" described above in "Method for removing $Q^1$ in molecule of compound [C-1]".

The amount of the scavenger that can be used in this step is, for example, suitably in the range of 1 mole to 100 moles, and preferably in the range of 1 mole to 50 moles, per mole of the compound [A-1a-Q1], (ii) Preparation of Compound [A-1] in which G is (1) Long-Chain Alkyl-Carbonyl, (2) Benzoyl Substituted with 1 to 5 Long-Chain Alkyloxy and/or Long-Chain Alkenyloxy, or (3) the Substituent [7], and T is a Single Bond

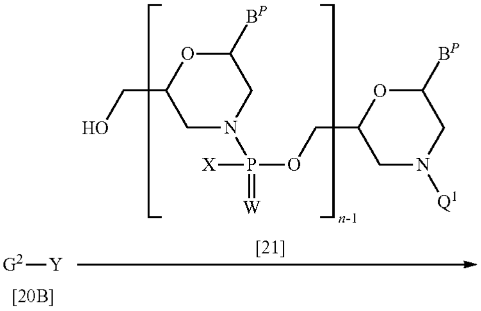

-continued

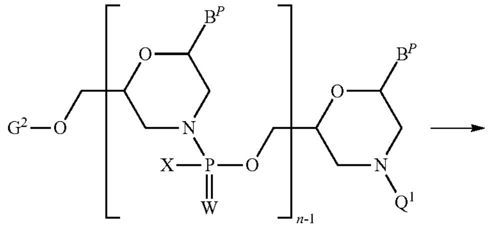

[A-1b-Q1]

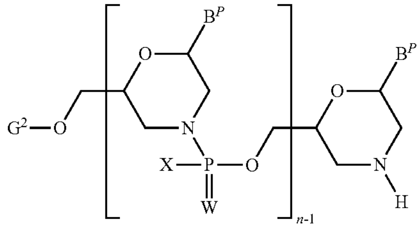

[A-1b]

wherein n, $B^P$, $Q^1$, X, and W are as defined above, $G^2$ represents (1) long-chain alkyl-carbonyl, (2) benzoyl substituted with 1 to 5 long-chain alkyloxy and/or long-chain alkenyloxy, or (3) the substituent [7], and Y represents a hydroxyl group or a halogen.

A compound represented by the above general formula [A-1b] (hereinafter, referred to as "compound [A-1b]") is the compound [A-1] in which G is (1) long-chain alkyl-carbonyl, (2) benzoyl substituted with 1 to 5 long-chain alkyloxy and/or long-chain alkenyloxy, or (3) the substituent [7], and T is a single bond.

Hereinafter, an example of a preparation method for the compound [A-1b] is described.

Step 1: Preparation of Compound Represented by Above General Formula [A-1b-Q1] (Hereinafter, Referred to as "Compound [A-Lb-Q1]")

The compound [A-1b-Q1] can be prepared by condensing the compound [21] with a compound represented by the above general formula [20B] (hereinafter, referred to as "compound [20B][1]"). The condensation reaction can be carried out according to a known method.

In the case of using the compound [20B] having a hydroxyl group as Y in this step, the condensation reaction can be carried out in the range of −20° C. to 100° C. using a condensing agent in the presence or absence of a base.

In the case of using the compound [20B] having a halogen as Y in this step, the condensation reaction can be carried out in the range of −20° C. to 100° C. in the presence of a base.

Examples of the condensing agent that can be used in this step include 1,1'-oxalyldiimidazole, 1-ethyl-3-(3-dimethylaminopropyl)carbodiimide, dicyclohexylcarbodiimide, diethyl cyanophosphonate, 0-(benzotriazole-1-yl)-N,N,N',N'-tetramethyluronium hexafluorophosphate, 0-(7-azabenzotriazole-1-yl)-N,N,N',N'-tetramethyluronium hexafluorophosphate, and 1H-benzotriazole-1-yloxytripyrrolidinophosphonium hexafluorophosphate.

Examples of the base that can be used in this step include organic bases such as triethylamine, N,N-diisopropylethylamine, N,N-dimethylaniline, pyridine, and 1,8-diazabicyclo[5,4,0]-7-undecene.

The solvent that can be used in this step is not particularly limited, but examples thereof include: ethers such as THF, 1,4-dioxane, and diethyl ether; amides such as dimethylformamide and dimethylacetamide; nitriles such as acetonitrile and propionitrile; hydrocarbons such as benzene and toluene; halogenated hydrocarbons such as chloroform and methylene chloride; and mixed solvents thereof.

Moreover, in the case of using the compound [20B] having a hydroxyl group as Y in this step, an additive can be used if necessary.

Examples of the additive that can be used in this step include 4-dimethylaminopyridine, 1-hydroxybenzotriazole, and 1-hydroxy-7-azabenzotriazole.

The reaction time is different depending on the type of the raw material to be used, the reaction temperature, etc., but the range of 10 minutes to 24 hours is usually suitable.

Each of the amounts of the compound [21] and the condensing agent is, for example, suitably in the range of 1 mole to 1.5 moles per mole of the compound [20B].

The amount of the base is, for example, in the range of 1 equivalent to 10 equivalents, and preferably in the range of 1 equivalent to 4 equivalents, with respect to the compound [20B].

Step 2: Preparation of Compound [A-1b]

The compound [A-1b] can be prepared by treating the compound [A-1b-Q1] with an acid.

Examples of the "acid" that can be used in this step include the same "acids" described above in "Method for removing $Q^1$ in molecule of compound [C-1]".

The amount of the acid that can be used in this step is, for example, suitably in the range of 1 mole to 500 moles, and preferably in the range of 2 moles to 200 moles, per mole of the compound [A-1b-Q1].

The acid that can be used in this step may be diluted with a suitable solvent, and is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

In this step, a scavenger may be used if necessary.

Examples of the "scavenger" that can be used in this step include the same "scavengers" described above in "Method for removing $Q^1$ in molecule of compound [C-1]".

The amount of the scavenger that can be used in this step is, for example, suitably in the range of 1 mole to 100 moles, and preferably in the range of 1 mole to 50 moles, per mole of the compound [A-1b-Q1].

(iii) Preparation of Compound [A-1] in which G is (1) Long-Chain Alkyl-Carbonyl, (2) Benzoyl Substituted with 1 to 5 Long-Chain Alkyloxy and/or Long-Chain Alkenyloxy, or (3) the Substituent [7], and T is the Substituent [11]

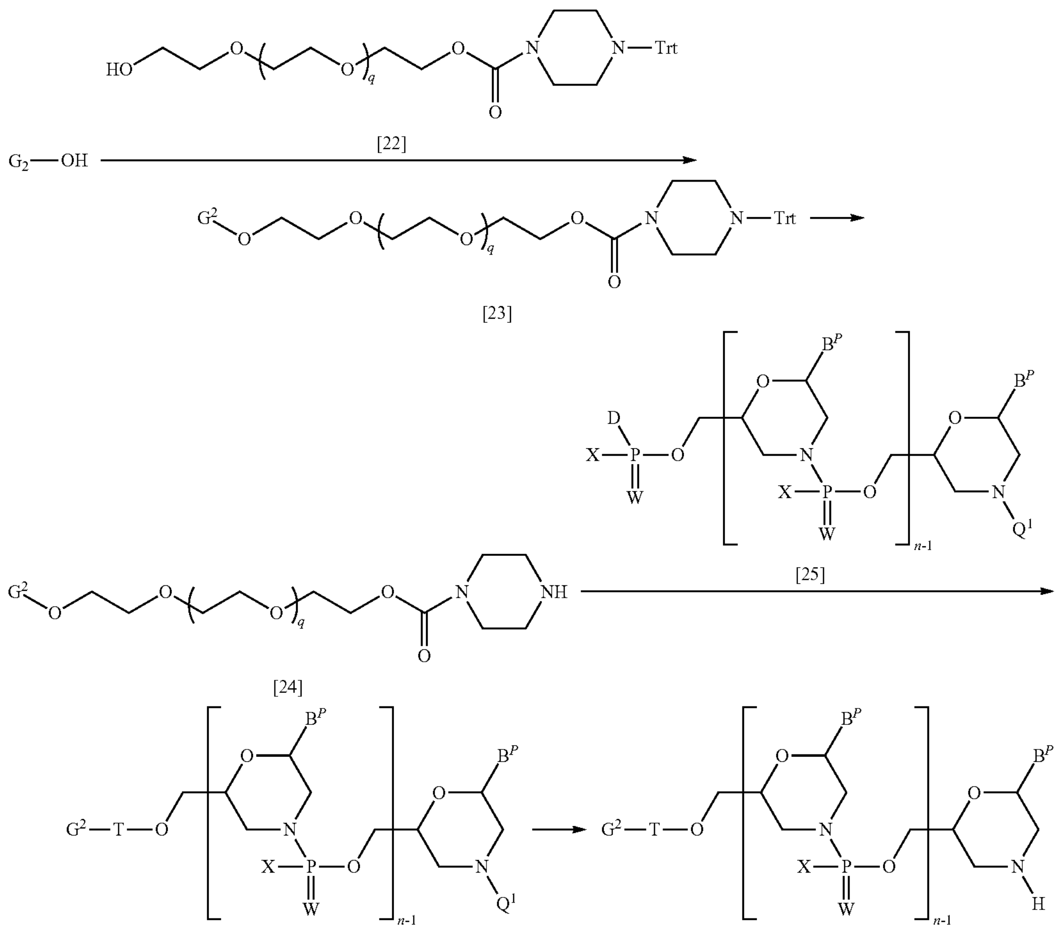

[A-1c-Q1] [A-1c]

wherein n, q, $B^P$, D, $G^2$, $Q^1$, T, X, and W are as defined above, and Trt is trityl.

A compound represented by the above general formula [A-1c] (hereinafter, referred to as "compound [A-1c]") is the compound [A-1] in which G is (1) long-chain alkyl-carbonyl, (2) benzoyl substituted with 1 to 5 long-chain alkyloxy and/or long-chain alkenyloxy, or (3) the substituent [7], and T is the substituent [11].

Hereinafter, an example of a preparation method for the compound [A-1c] is described.

Step 1: Preparation of Compound Represented by Above General Formula [23] (Hereinafter, Referred to as "Compound [23]")

The compound [23] can be prepared by condensing a compound represented by the above general formula [20C] (hereinafter, referred to as "compound [20C]") with a compound represented by the above general formula [22] (hereinafter, referred to as "compound [22]").

Although the compound [20C] is a carboxylic acid compound, a reactive derivative thereof can also be used in this step. Examples of the reactive derivative of the compound [20C] include those usually used in ester condensation formation reactions such as acid halides (for example, acid chloride, acid bromide).

The compound [22] can be prepared according to a known method (see, for example, US2014/0330006A1).

In addition, the compound [20C] in which G is benzoyl substituted with 1 to 5 long-chain alkyloxy and/or long-chain alkenyloxy can be prepared according to a known method (see, for example, WO2014/077292A1).

Step 2: Preparation of Compound Represented by Above General Formula [24] (Hereinafter, Referred to as "Compound [24]")

The compound [24] can be prepared by removing the trityl group in the molecule of the compound [23] with an acid.

Step 3: Preparation of Compound Represented by Above General Formula [A-1c-Q1] (Hereinafter, Referred to as "Compound [A-1c-Q1]")

The compound [A-1c-Q1] can be prepared by condensing the compound [24] with a compound represented by the above general formula [25] (hereinafter, referred to as "compound [25]"). The condensation reaction and the deprotection reaction can be carried out according to a known method.

Step 4: Preparation of Compound [A-1c]

The compound [A-1c] can be prepared by treating the compound [A-1c-Q1] with an acid.

Examples of the "acid" that can be used in this step include the same "acids" described above in "Method for removing $Q^1$ in molecule of compound [C-1]".

The amount of the acid that can be used in this step is, for example, suitably in the range of 1 mole to 500 moles, and preferably in the range of 2 moles to 200 moles, per mole of the compound [A-1c-Q1].

The acid that can be used in this step may be diluted with a suitable solvent, and is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

In this step, a scavenger may be used if necessary.

Examples of the "scavenger" that can be used in this step include the same "scavengers" described above in "Method for removing $Q^1$ in molecule of compound [C-1]".

The amount of the scavenger that can be used in this step is, for example, suitably in the range of 1 mole to 100 moles, and preferably in the range of 1 mole to 50 moles, per mole of the compound [A-1c-Q1].

(iv) Preparation of Compound [A-1] in which G is the Substituent [7] and T is a Single Bond

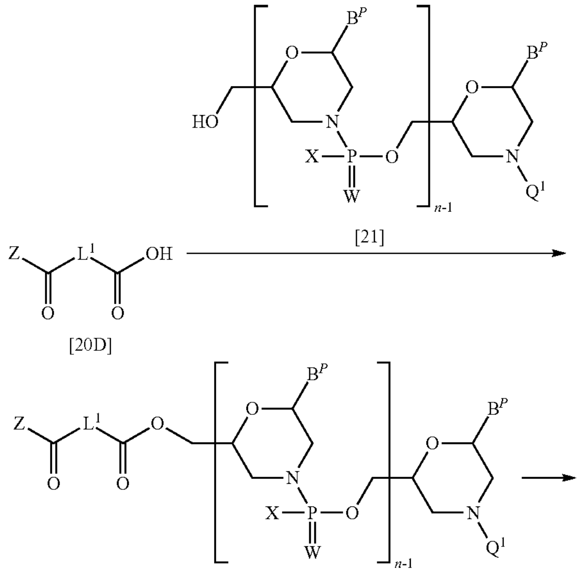

[21]

[20D]

[A-1d-Q1]

-continued

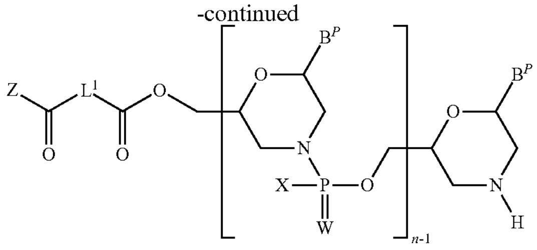

[A-1d]

wherein n, $B^P$, $L^1$, $Q^1$, X, W, and Z are as defined above.

A compound represented by the above general formula [A-1d] (hereinafter, referred to as "compound [A-1d]") is the compound [A-1] in which G is the substituent [7] and T is a single bond.

Hereinafter, an example of a preparation method for the compound [A-1d] is described.

Step 1: Preparation of Compound Represented by Above General Formula [A-1d-Q1] (Hereinafter, Referred to as "Compound [A-1d-Q1]")

The compound [A-1d-Q1] can be prepared by condensing a compound represented by the above general formula [20D](hereinafter, referred to as "compound [20D]") with a compound represented by the above general formula [21] (hereinafter, referred to as "compound [21]"). The condensation reaction can be carried out according to a known method.

Although the compound [20D] is a carboxylic acid compound, a reactive derivative thereof can also be used in this step. Examples of the reactive derivative of the compound [20D] include those usually used in ester condensation formation reactions such as acid halides (for example, acid chloride, acid bromide).

In the case of using the compound [20D], the reaction can be carried out in the range of −20° C. to 100° C. using a condensing agent in the presence or absence of a base.

Examples of the condensing agent that can be used in this step include 1,1'-oxalyldiimidazole, 1-ethyl-3-(3-dimethylaminopropyl)carbodiimide, dicyclohexylcarbodiimide, diethyl cyanophosphonate, 0-(benzotriazole-1-yl)-N,N,N',N'-tetramethyluronium hexafluorophosphate, 0-(7-azabenzotriazole-1-yl)-N,N,N',N'-tetramethyluronium hexafluorophosphate, and 1H-benzotriazole-1-yloxytripyrrolidinophosphonium hexafluorophosphate.

Examples of the base that can be used in this step include organic bases such as triethylamine, N,N-diisopropylethylamine, N,N-dimethylaniline, pyridine, and 1,8-diazabicyclo [5,4,0]-7-undecene.

The solvent that can be used in this step is not particularly limited, but examples thereof include: ethers such as THF, 1,4-dioxane, and diethyl ether; amides such as dimethylformamide and dimethylacetamide; nitriles such as acetonitrile and propionitrile; hydrocarbons such as benzene and toluene; halogenated hydrocarbons such as chloroform and methylene chloride; and mixed solvents thereof. Moreover, an additive can be used if necessary.

Examples of the additive that can be used in this step include 4-dimethylaminopyridine, 1-hydroxybenzotriazole, and 1-hydroxy-7-azabenzotriazole.

The reaction time is different depending on the type of the raw material to be used, the reaction temperature, etc., but the range of 10 minutes to 24 hours is usually suitable.

Each of the amounts of the compound [21] and the condensing agent is, for example, suitably in the range of 1 mole to 1.5 moles per mole of the compound [20D].

The amount of the base is, for example, in the range of 1 equivalent to 10 equivalents, and preferably in the range of 1 equivalent to 4 equivalents, with respect to the compound [20D].

Step 2: Preparation of Compound [A-1d]

The compound [A-1d] can be prepared by treating the compound [A-1d-Q1] with an acid.

Examples of the "acid" that can be used in this step include the same "acids" described above in "Method for removing $Q^1$ in molecule of compound [C-1]".

The amount of the acid that can be used in this step is, for example, suitably in the range of 1 mole to 500 moles, and preferably in the range of 2 moles to 200 moles, per mole of the compound [A-1d-Q1].

The acid that can be used in this step may be diluted with a suitable solvent, and is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

Moreover, in this step, a scavenger may be used if necessary.

Examples of the "scavenger" that can be used in this step include the same "scavengers" described above in "Method for removing $Q^1$ in molecule of compound [C-1]".

The amount of the scavenger that can be used in this step is, for example, suitably in the range of 1 mole to 100 moles, and preferably in the range of 1 mole to 50 moles, per mole of the compound [A-1d-Q1].

The compound [20D] can be prepared, for example, according to a preparation method described below.

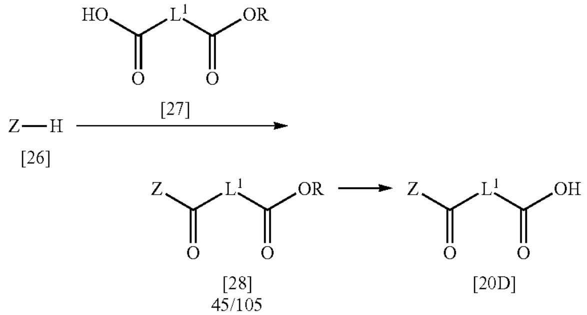
[27]
[26]
[28]
45/105
[20D]

wherein $L^1$ and Z are as defined above, and

R represents $C_{1-6}$ alkyl.

Step 1: Preparation of Compound Represented by Above General Formula [28] (Hereinafter, Referred to as "Compound [28]")

The compound [28] can be prepared by condensing a compound represented by the above general formula [26] (hereinafter, referred to as "compound [26]") with a compound represented by the above general formula [27] (hereinafter, referred to as "compound [27]"). The condensation reaction can be carried out according to a known method.

As the reagents, reaction conditions, etc., that can be used in this step, the same as those described above in "Preparation of compound [A-1b-Q1]" can be used.

Step 2: Preparation of Compound [20D]

The compound [20D] can be prepared by carrying out ester hydrolysis of the compound [28]. The ester hydrolysis reaction can be carried out according to a known method.

The solvent that can be used in this step is not particularly limited, but examples thereof include: water; alcohols such as methanol and ethanol; ethers such as tetrahydrofuran, 1,4-dioxane, and diethyl ether; nitriles such as acetonitrile and propionitrile; hydrocarbons such as benzene and toluene; halogenated hydrocarbons such as chloroform and methylene chloride; and mixed solvents thereof.

This step is performed in the range of 20° C. to 100° C. in the presence of a base such as sodium hydroxide, potassium hydroxide, and lithium hydroxide.

The reaction time is different depending on the type of the raw material to be used, the reaction temperature, etc., but the range of 10 minutes to 24 hours is usually suitable.

The compound [26] can be prepared, for example, according to methods described in (a) to (j) below.

(a) The compound [26] in which Z is the substituent [8A], $R^{8a}$ is a hydrogen atom, and $R^{8b}$ is long-chain alkyl, can be prepared, for example, by using a primary amine compound available as a commercial product or by aminating a halogenated alkyl available as a commercial product.

(b) The compound [26] in which Z is the substituent [8A] or the substituent [8B], $R^{8a}$ is $C_{1-6}$ alkyl, $R^{8b}$ is the same or different and are each long-chain alkyl, can be prepared, for example, by alkylating a primary amine compound available as a commercial product. The alkylation reaction can be carried out according to a known method.

(c) The compound [26] in which Z is the substituent [8C] can be prepared according to a known method (see, for example, Cancer Res., 2008 Nov. 1; 68 (21): 8843-8851, Chem. Sci., 2016, 7, 2308-2321).

(d) The compound [26] in which Z is the substituent [8D] can be prepared, for example, by condensing methyl phthalate with 1-(tert-butoxycarbonyl)piperazine, then hydrolyzing the ester moiety with an alkali such as sodium hydroxide, further condensing the hydrolysate with the compound [26] in which Z is the substituent [8A], and then removing the tert-butoxycarbonyl group with an acid such as trifluoroacetic acid. The condensation reaction, the hydrolysis reaction with the alkali, and the deprotection reaction of the tert-butoxycarbonyl group with the acid can be carried out according to a known method.

(e) The compound [26] in which Z is the substituent [8E] and $R^{8e}$ is a long-chain alkyl group can be prepared, for example, by alkylating one of the hydroxyl groups of ethane-1,2-diol using halogenated alkyl.

The compound [26] in which Z is the substituent [8E] and $R^{8e}$ is long-chain alkyl-carbonyl can be prepared, for example, by converting one of the hydroxyl groups of ethane-1,2-diol to long-chain alkyl-carbonyl. As the compound used for conversion to long-chain alkyl-carbonyl, for example, the corresponding carboxylic acid compound or a reactive derivative thereof can be used. Examples of the reactive derivative include those usually used in ester condensation formation reactions such as acid halides (for example, acid chloride, acid bromide).

The compound [26] in which Z is the substituent [8E] and $R^{8e}$ is a benzoyl group substituted with 1 to 5 long-chain alkyloxy and/or long-chain alkenyloxy, can be prepared, for example, by condensing one of the hydroxyl groups of ethane-1,2-diol with the compound [20C].

(f) The compound [26] in which Z is the substituent [8F] can be prepared, for example, according to the same method as the preparation method for the compound (18) in which Z is the substituent [8E], using 2-aminoethanol instead of ethane-1,2-diol.

(g) The compound [26] in which Z is the substituent [8G] can be prepared, for example, by condensing 9-fluorenylmethyloxycarbonyl-phenylalanine with the compound [26] in which Z is the substituent [8A], and then removing the 9-fluorenylmethyloxycarbonyl group with piperidine. The condensation reaction and the deprotection reaction of the 9-fluorenylmethyloxycarbonyl-phenylalanine group can be carried out according to a known method.

(h) The compound [26] in which Z is the substituent [8H] can be prepared, for example, by: performing preparation according to the same method as the preparation method for the compound [26] in which Z is the substituent [8E], using 1-(tert-butoxycarbonyl)piperazine instead of ethane-1,2-diol; and then deprotecting the tert-butoxycarbonyl group in the molecule with an acid.

(i) The compound [26] in which Z is the substituent [81], the substituent [8J], the substituent [8K], the substituent [8L], or the substituent [8N], can be prepared according to a known method (see, for example, Japanese Patent No. 5705512, Tetrahedron Letters, Vol. 53, 1936-1939 (2012), WO2014/189142A1, WO2016/060135A1, and WO2016/140232A1).

(j) 9H-xanthene-9-one having corresponding long-chain alkyloxy can be prepared, for example, by treatment 9H-xanthene-9-one having a hydroxyl group with a base such as sodium hydride, and followed by reaction with appropriate halogenated long-chain alkyl. The compound [26] in which Z is the substituent [8M] can be prepared by further reaction by optionally substituted phenylmagnesium bromide. It should be noted that the compound [26] in which the desired Z is the substituent [8M] can be prepared by adjusting a 9H-xanthene-9-one derivative or phenylmagnesium bromide derivative having various substituents according to a known method.

The compound [21] with n=1 can be prepared according to a known method (see, for example, WO91/09033A1), and the compound [21] with n>1 can be prepared according to a method described hereinafter.

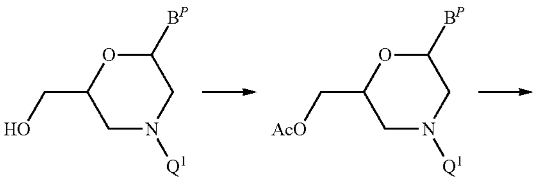

[29] [30]

-continued

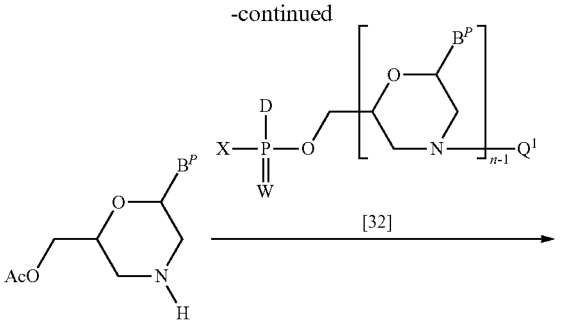

[31]

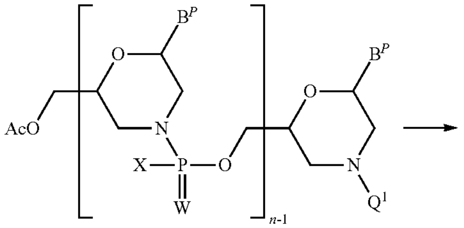

[33]

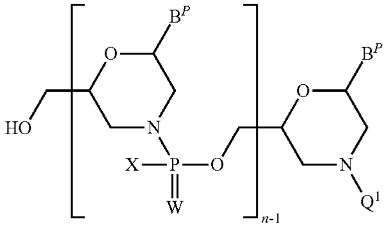

[21]

wherein n, $B^P$, D, $Q^1$, X, and W are as defined above, and Ac represents acetyl.

Step 1: Preparation of Compound Represented by Above General Formula [30] (Hereinafter, Referred to as "Compound [30]")

The compound [30] can be prepared by acetylating a compound represented by the above general formula [29] (see, for example, WO91/09033A1) with acetic anhydride in the presence of a base. The acetylation reaction can be carried out according to a known method.

Step 2: Preparation of Compound Represented by Above General Formula [31] (Hereinafter, Referred to as "Compound [31]")

The compound [31] can be prepared by treating the compound [30] with an acid. $Q^1$ can be removed according to a known method.

Step 3: Preparation of Compound Represented by Above General Formula [33] (Hereinafter, Referred to as "Compound [33]")

The compound [33] can be prepared by condensing the compound [31] with a compound represented by the above general formula [32] (hereinafter, referred to as "compound [32]"). The condensation reaction can be carried out according to a known method (see, for example, WO91/09033A1).

The compound [32] can be prepared, for example, according to a known method (see, for example, WO91/09033A1).

Step 4: Preparation of Compound [21]

The compound [21] can be prepared, for example, by selectively removing the acetyl group of compound [33] using an alkali metal alkoxide such as sodium methoxide. Acetyl can be removed according to a known method (see, for example, Tetrahedron Letters, Vol. 50, 1751-1753 (2009)).

(J-2) Preparation of Compound [A-2]

The compound [A] comprising one or more nucleoside units selected from the group consisting of the nucleoside unit [4a], the nucleoside unit [4b], and the nucleoside unit [4c] and in which the phosphate bond between each nucleoside unit is the phosphate bond [5], can be prepared, for example, according to methods described in (i) to (iv) below.

(i) Preparation of Compound [A-2] in which G is a Silyl Substituent and T is a Single Bond

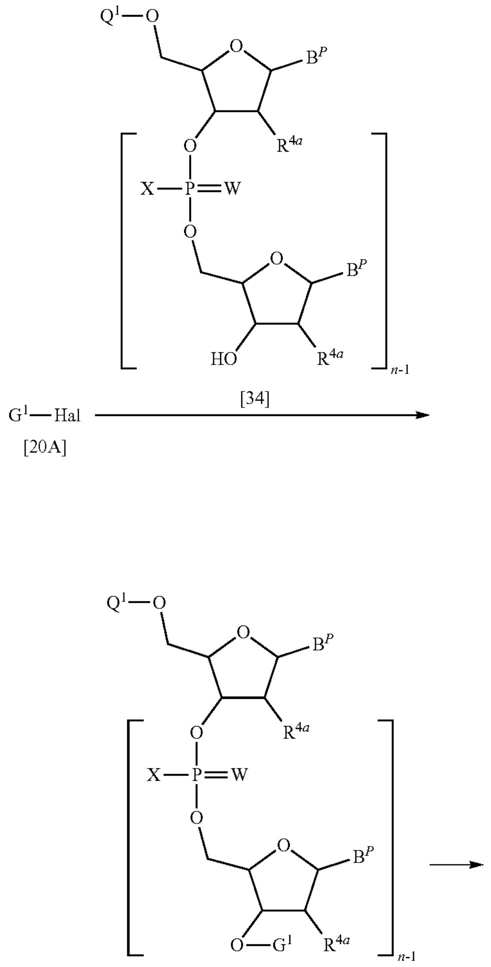

[34]

[20A]

[A-2a-Q1]

-continued

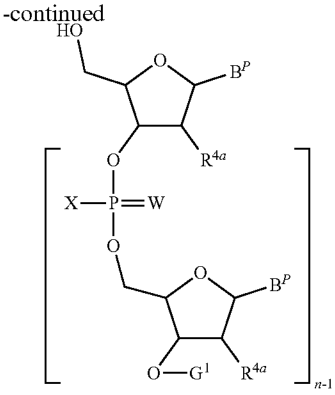

[A-2a]

wherein n, $B^P$, $G^1$, Hal, $Q^1$, $R^{4a}$, X, and W are as defined above.

A compound represented by the above general formula [A-2a] (hereinafter, referred to as "compound [A-2a]") is the compound [A-2] in which G is a silyl substituent and T is a single bond.

Hereinafter, an example of a preparation method for the compound [A-2a] is described.

Step 1: Preparation of Compound Represented by Above General Formula [A-2a-Q1] (Hereinafter, Referred to as "Compound [A-2A-Q1]")

The compound [A-2a-Q1] can be prepared by using the compound [20A] on a compound represented by the above general formula [34] (hereinafter, referred to as "compound [34]") and introducing a silyl substituent to the hydroxyl group at the 3'-position of the 3'-terminal nucleoside unit of the compound [34]. The introduction reaction of the silyl substituent can be carried out according to a known method.

Step 2: Preparation of Compound [A-2a]

The compound [A-2a] can be prepared by treating the compound [A-2a-Q1] with an acid.

Examples of the "acid" that can be used in this step include the same "acids" described above in "Removal of $Q^1$ in molecule of compound [D-2]".

The amount of the acid that can be used in this step is, for example, suitably in the range of 1 mole to 500 moles, and preferably in the range of 2 moles to 200 moles, per mole of the compound [A-2a-Q1].

The acid that can be used in this step may be diluted with a suitable solvent, and is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

In this step, a scavenger may be used if necessary.

Examples of the "scavenger" that can be used in this step include the same "scavengers" described above in "Removal of $Q^1$ in molecule of compound [D-2]".

The amount of the scavenger that can be used in this step is, for example, suitably in the range of 1 mole to 100 moles, and preferably in the range of 1 mole to 50 moles, per mole of the compound [A-2a-Q1].

(ii) Preparation of Compound [A-2] in which G is (1) Long-Chain Alkyl-Carbonyl (2) Benzoyl Substituted with 1 to 5 Long-Chain Alkyloxy and/or Long-Chain Alkenyloxy, or (3) the Substituent [7], and T is a Single Bond

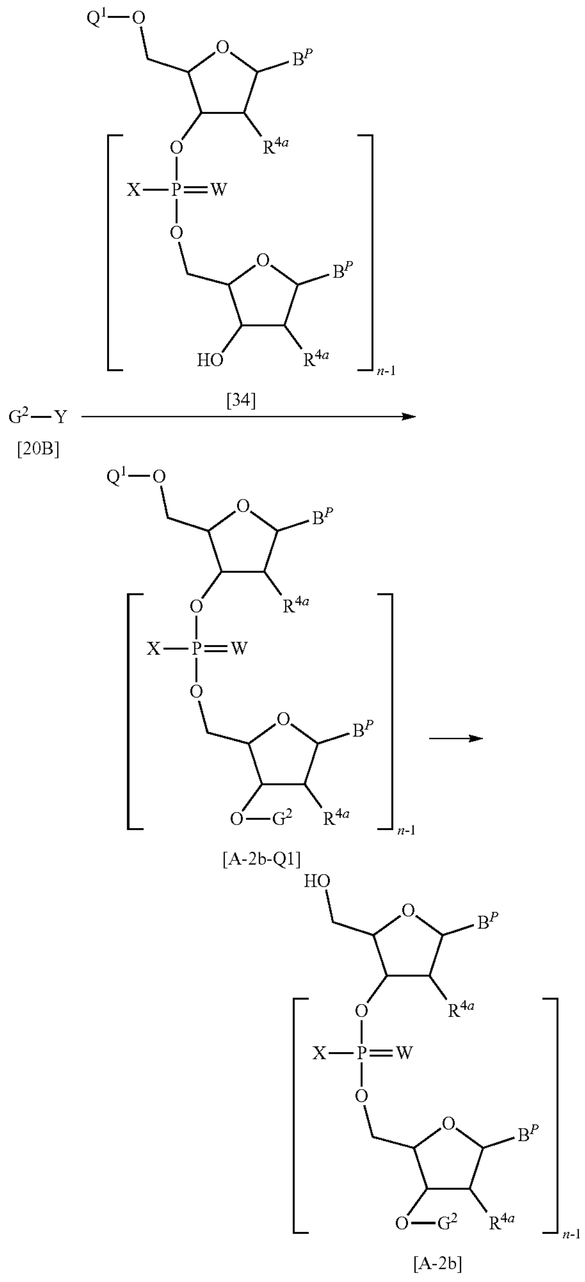

[20B] [34] [A-2b-Q1] [A-2b]

wherein n, $B^P$, $G^2$, $Q^1$, $R^{4a}$, X, Y, and W are as defined above.

A compound represented by the above general formula [A-2b] (hereinafter, referred to as "compound [A-2b]") is the compound [A-2] in which G is (1) long-chain alkyl-carbonyl, (2) benzoyl substituted with 1 to 5 long-chain alkyloxy and/or long-chain alkenyloxy, or (3) the substituent [7], and T is a single bond.

Hereinafter, an example of a preparation method for the compound [A-2b] is described.

Step 1: Preparation of Compound Represented by Above General Formula [A-2b-Q1] (Hereinafter, Referred to as "Compound [A-2b-Q1]")

The compound [A-2b-Q1] can be prepared by condensing the compound [20B] with the compound [34]. The condensation reaction can be carried out according to a known method.

In the case of using the compound [20B] having a hydroxyl group as Y in this step, the condensation reaction can be carried out in the range of −20° C. to 100° C. using a condensing agent in the presence or absence of a base.

In the case of using the compound [20B] having a halogen as Y in this step, the condensation reaction can be carried out in the range of −20° C. to 100° C. in the presence of a base.

Examples of the condensing agent that can be used in this step include 1,1'-oxalyldiimidazole, 1-ethyl-3-(3-dimethylaminopropyl)carbodiimide, dicyclohexylcarbodiimide, diethyl cyanophosphonate, 0-(benzotriazole-1-yl)-N,N,N',N'-tetramethyluronium hexafluorophosphate, 0-(7-azabenzotriazole-1-yl)-N,N,N',N'-tetramethyluronium hexafluorophosphate, and 1H-benzotriazole-1-yloxytripyrrolidinophosphonium hexafluorophosphate.

Examples of the base that can be used in this step include organic bases such as triethylamine, N,N-diisopropylethylamine, N,N-dimethylaniline, pyridine, and 1,8-diazabicyclo[5,4,0]-7-undecene.

The solvent that can be used in this step is not particularly limited, but examples thereof include: ethers such as THF, 1,4-dioxane, and diethyl ether; amides such as dimethylformamide and dimethylacetamide; nitriles such as acetonitrile and propionitrile; hydrocarbons such as benzene and toluene; halogenated hydrocarbons such as chloroform and methylene chloride; and mixed solvents thereof.

Moreover, in the case of using the compound [20B] having a hydroxyl group as Y in this step, an additive can be used if necessary.

Examples of the additive that can be used include 4-dimethylaminopyridine, 1-hydroxybenzotriazole, and 1-hydroxy-7-azabenzotriazole.

The reaction time is different depending on the type of the raw material to be used, the reaction temperature, etc., but the range of 10 minutes to 24 hours is usually suitable.

Each of the amounts of the compound [20B] and the condensing agent is, for example, suitably in the range of 1 mole to 1.5 moles per mole of the compound [34].

The amount of the base is, for example, in the range of 1 equivalent to 10 equivalents, and preferably in the range of 1 equivalent to 4 equivalents, with respect to the compound [34].

Step 2: Preparation of Compound [A-2b]

The compound [A-2b] can be prepared by treating the compound [A-2b-Q1] with an acid.

Examples of the "acid" that can be used in this step include the same "acids" described above in "Removal of $Q^1$ in molecule of compound [D-2]".

The amount of the acid that can be used in this step is, for example, suitably in the range of 1 mole to 500 moles, and preferably in the range of 2 moles to 200 moles, per mole of the compound [A-2b-Q1].

The acid that can be used in this step may be diluted with a suitable solvent, and is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

In this step, a scavenger may be used if necessary.

Examples of the "scavenger" that can be used in this step include the same "scavengers" described above in "Removal of $Q^1$ in molecule of compound [D-2]".

The amount of the scavenger that can be used in this step is, for example, suitably in the range of 1 mole to 100 moles, and preferably in the range of 1 mole to 50 moles, per mole of the compound [A-2b-Q1].

(iii) Preparation of Compound [A-2] in which G is (1) Long-Chain Alkyl-Carbonyl. (2) Benzoyl Substituted with 1 to 5 Long-Chain Alkyloxy and/or Long-Chain Alkenyloxy, or (3) the Substituent [7], and T is the Substituent [11]

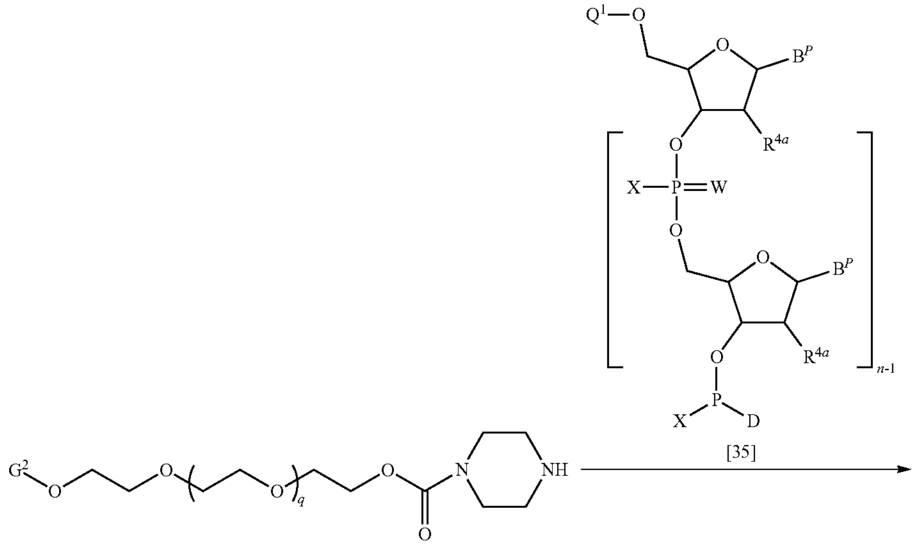

[35]

[24]

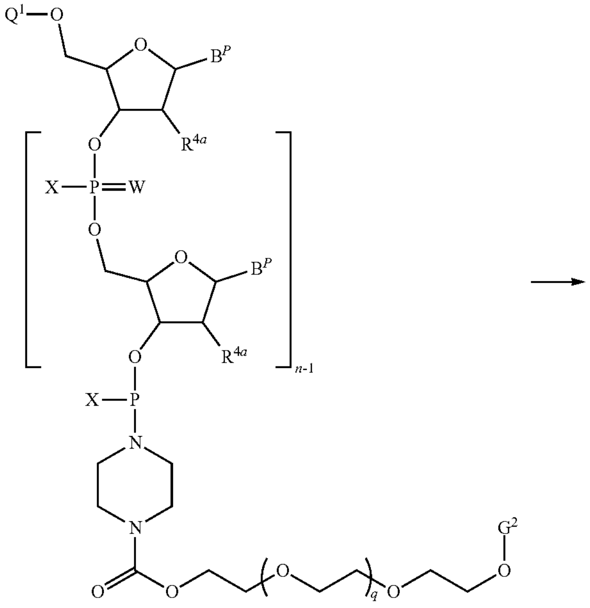

[36]

-continued

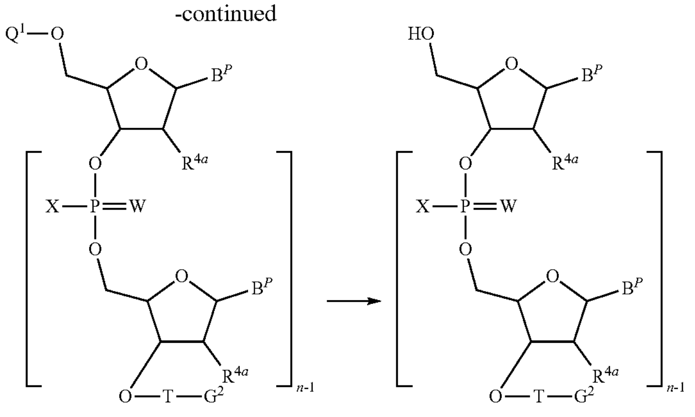

[A-2c-Q1] [A-2c]

wherein n, q, $B^P$, D, $G^2$, $Q^1$, $R^{4a}$, T, X, and W are as defined above.

A compound represented by the above general formula [A-2c] (hereinafter, referred to as "compound [A-2c]") is the compound [A-2] in which G is (1) long-chain alkyl-carbonyl, (2) benzoyl substituted with 1 to 5 long-chain alkyloxy and/or long-chain alkenyloxy, or (3) the substituent [7], and T is the substituent [11].

Hereinafter, an example of a preparation method for the compound [A-2c] is described.

Step 1: Preparation of Compound Represented by Above General Formula [36] (Hereinafter, Referred to as "Compound [36]")

The compound [36] can be prepared by condensing the compound [24] with a compound represented by the above general formula [35] (hereinafter, referred to as "compound [35]"). The condensation reaction and the deprotection reaction can be carried out according to a known method.

Step 2: Preparation of Compound Represented by Above General Formula [A-2c-Q1] (Hereinafter, Referred to as "Compound [A-2c-Q1]")

The compound [A-2c-Q1] can be prepared by an oxidizing agent to the compound [36]. The oxidation reaction can be carried out according to a known method.

Examples of the "oxidizing agent" include iodine and tert-butyl hydroperoxide. In addition, the oxidizing agent that can be used in this step can also be used after being diluted with a suitable solvent such that the concentration thereof is 0.05 to 2 M. The solvent is not particularly limited, but examples thereof include pyridine, tetrahydrofuran, water, and mixed solvents thereof. For example, iodine/water/pyridine-tetrahydrofuran, iodine/pyridine-acetic acid, or a peroxide agent (tert-butyl hydroperoxide/methylene chloride, etc.) can be used.

The reaction temperature is preferably 20° C. to 50° C.

The reaction time is different depending on the type of the oxidizing agent to be used and the reaction temperature, but 1 minute to 30 minutes is usually suitable.

The amount of the oxidizing agent is preferably 1 to 100 moles, and more preferably 10 to 50 moles, per mole of the compound [36], Step 3: Preparation of Compound [A-2c]

The compound [A-2c] can be prepared by treating the compound [A-2c-Q1] with an acid.

Examples of the "acid" that can be used in this step include the same "acids" described above in "Removal of $Q^1$ in molecule of compound [D-2]".

The amount of the acid that can be used in this step is, for example, suitably in the range of 1 mole to 500 moles, and preferably in the range of 2 moles to 200 moles, per mole of the compound [A-2c-Q1].

The acid that can be used in this step may be diluted with a suitable solvent, and is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

Moreover, in this step, a scavenger may be used if necessary.

Examples of the "scavenger" that can be used in this step include the same "scavengers" described above in "Removal of $Q^1$ in molecule of compound [D-2]".

The amount of the scavenger that can be used in this step is, for example, suitably in the range of 1 mole to 100 moles, and preferably in the range of 1 mole to 50 moles, per mole of the compound [A-2c-Q1].

(iv) Preparation of Compound [A-2] in which G is the Substituent [7] and T is a Single Bond

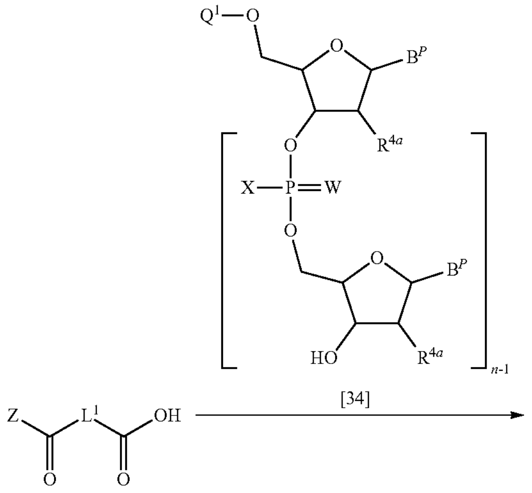

[34]

[20D]

-continued

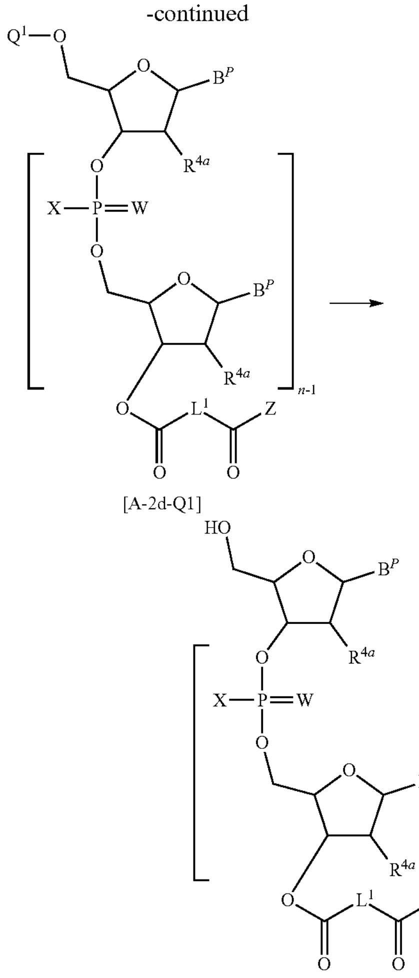

[A-2d]

wherein n, $B^P$, $L^1$, $Q^1$, $R^{4a}$, X, W, and Z are as defined above.

A compound represented by the above general formula [A-2d] (hereinafter, referred to as "compound [A-2d]") is the compound [A-2] in which G is the substituent [7] and T is a single bond.

Hereinafter, an example of a preparation method for the compound [A-2d] is described.

Step 1

A compound represented by the above general formula [A-2d-Q1] (hereinafter, referred to as "compound [A-2d-Q1]") can be prepared by condensing the compound [20D] with the compound [34]. The condensation reaction can be carried out according to a known method.

Although the compound [20D] is a carboxylic acid compound, a reactive derivative thereof can also be used in this step. Examples of the reactive derivative of the compound [20D]include those usually used in ester condensation formation reactions such as acid halides (for example, acid chloride, acid bromide).

In the case of using the compound [20D], the reaction can be carried out in the range of −20° C. to 100° C. using a condensing agent in the presence or absence of a base.

Examples of the condensing agent that can be used in this step include 1,1'-oxalyldiimidazole, 1-ethyl-3-(3-dimethylaminopropyl)carbodiimide, dicyclohexylcarbodiimide, diethyl cyanophosphonate, O-(benzotriazole-1-yl)-N,N,N',N'-tetramethyluronium hexafluorophosphate, 0-(7-azabenzotriazole-1-yl)-N,N,N',N'-tetramethyluronium hexafluorophosphate, and 1H-benzotriazole-1-yloxytripyrrolidinophosphonium hexafluorophosphate.

Examples of the base that can be used in this step include organic bases such as triethylamine, N,N-diisopropylethylamine, N,N-dimethylaniline, pyridine, and 1,8-diazabicyclo [5,4,0]-7-undecene.

The solvent that can be used in this step is not particularly limited, but examples thereof include: ethers such as THF, 1,4-dioxane, and diethyl ether; amides such as dimethylformamide and dimethylacetamide; nitriles such as acetonitrile and propionitrile; hydrocarbons such as benzene and toluene; halogenated hydrocarbons such as chloroform and methylene chloride; and mixed solvents thereof. Moreover, an additive can be used if necessary.

Examples of the additive that can be used in this step include 4-dimethylaminopyridine, 1-hydroxybenzotriazole, and 1-hydroxy-7-azabenzotriazole.

The reaction time is different depending on the type of the raw material to be used, the reaction temperature, etc., but the range of 10 minutes to 24 hours is usually suitable.

Each of the amounts of the compound [20D] and the condensing agent is, for example, suitably in the range of 1 mole to 1.5 moles per mole of the compound [34].

The amount of the base is, for example, in the range of 1 equivalent to 10 equivalents, and preferably in the range of 1 equivalent to 4 equivalents, with respect to the compound [34].

Step 2

The compound [A-2d] can be prepared by treating the compound [A-2d-Q1] with an acid.

Examples of the "acid" that can be used in this step include the same "acids" described above in "Removal of $Q^1$ in molecule of compound [D-2]".

The amount of the acid that can be used in this step is, for example, suitably in the range of 1 mole to 500 moles, and preferably in the range of 2 moles to 200 moles, per mole of the compound [A-2d-Q1].

The acid that can be used in this step may be diluted with a suitable solvent, and is not particularly limited, but examples thereof include chloroform, dichloromethane, 1,1-dichloroethane, 1,2-dichloroethane, 1,1,2-trichloroethane, 1,2-dichloroethylene, 2,2,2-trifluoroethanol, and mixed solvents thereof.

Moreover, in this step, a scavenger may be used if necessary.

Examples of the "scavenger" that can be used in this step include the same "scavengers" described above in "Removal of $Q^1$ in molecule of compound [D-2]".

The amount of the scavenger that can be used in this step is, for example, suitably in the range of 1 mole to 100 moles, and preferably in the range of 1 mole to 50 moles, per mole of the compound [A-2d-Q1].

The compound [34] with n=1 can be prepared according to a known method (Current Protocols in Nucleic Acid Chemistry), and the compound [34] with n>1 can be prepared according to a known method (see, for example, US2010/273999A1).

Although the compound "A-2" is a compound of which each nucleoside unit is the nucleoside unit [4a], a compound in which all or a part of the nucleoside units [4a] are replaced by the nucleoside unit [4b] or the nucleoside unit [4c] can also be prepared by using the same method as described above.

(K) Preparation of Compound [B]

The compound [B] can be prepared, for example, by introducing the substituent [1] into a hydroxyl group of a compound corresponding to the compound [B].

Hereinafter, a preparation method for the compound [B] is described by introducing typical examples.

(K-1) Preparation of Compound [B-1]

The compound [B] comprising one or more nucleoside units [4h] and in which the phosphate bond between each nucleoside unit is the phosphate bond [5] can be prepared, for example, according to a method described hereinafter.

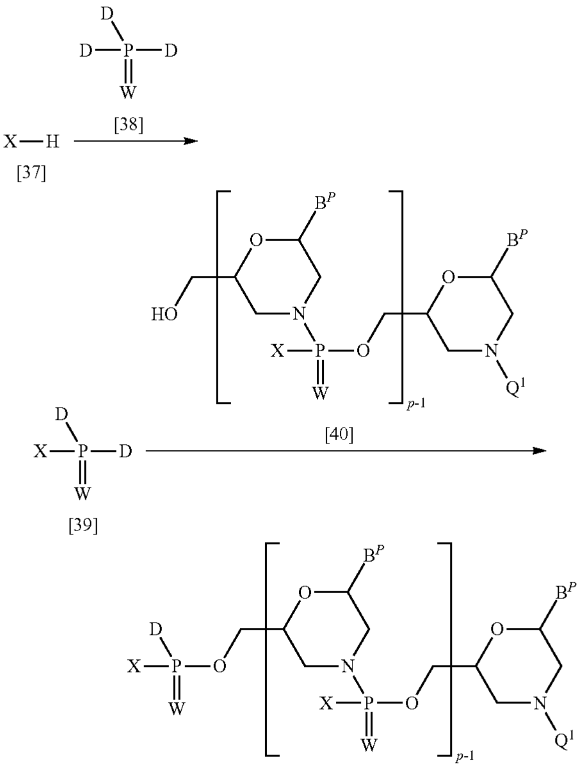

[38] [37] [40] [39]

[B-1]

wherein p, $B^P$, $Q^1$, D, X, and W are as defined above.

Step 1: Preparation of Compound Represented by Above General Formula [39] (Hereinafter, Referred to as "Compound [39]")

The compound [39] can be prepared by condensing a compound represented by the above general formula [37] (hereinafter, referred to as "compound [37]") with a compound represented by the above general formula [38] (hereinafter, referred to as "compound [38]"). The condensation reaction can be carried out according to a known method (see, for example, US2014/0330006A1, WO2012/043730A1, and WO2013/082548A1).

Step 2: Preparation of Compound [B-1]

The compound [B-1] can be prepared by condensing a compound represented by the above general formula [40] (hereinafter, referred to as "compound [40]") with the compound [39]. The condensation reaction can be carried out according to a known method (see, for example, US2014/0330006A1, WO2012/043730A1, WO2013/082548A1, and WO91/09033A1).

The compound [40] can be prepared by using the same method as the preparation method for the compound [21].

(K-2) Preparation of Compound [B-2]

The compound [B] comprising one or more nucleoside units selected from the group consisting of the nucleoside unit [4e], the nucleoside unit [4f], and the nucleoside unit [4g] and in which the phosphate bond between each nucleoside unit is the phosphate bond [5], can be prepared, for example, according to a method described below.

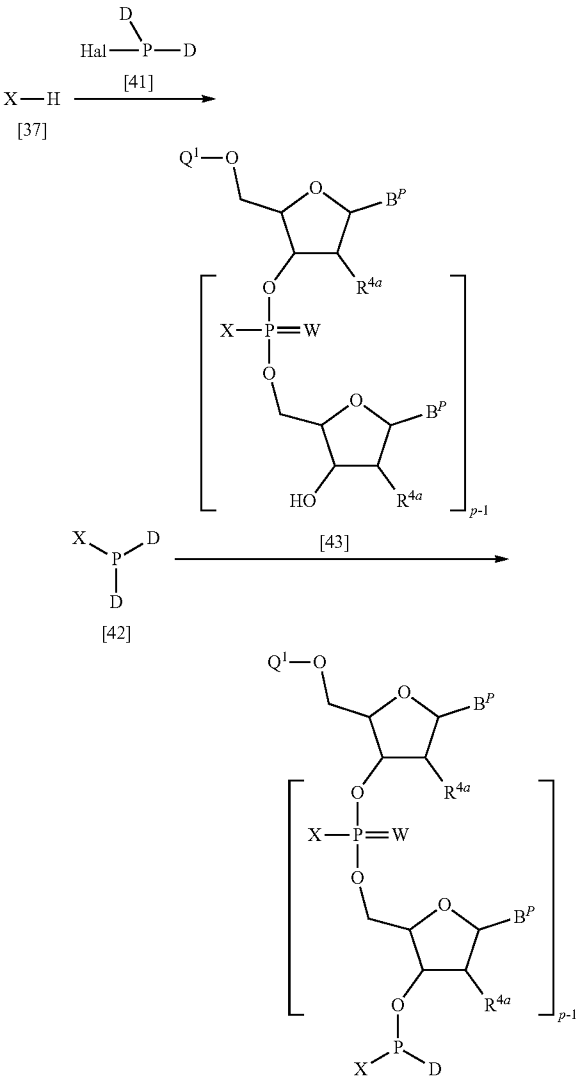

[41] [37] [43] [42]

[B-2]

wherein p, $B^P$, Hal, $Q^1$, D, $R^{4a}$, X, and W are as defined above.

Step 1: Preparation of Compound Represented by Above General Formula [42] (Hereinafter, Referred to as "Compound [42]")

The compound [42] can be prepared by reacting the compound [37] with a compound represented by the above general formula [41] (hereinafter, referred to as "compound [41]"). This reaction can be carried out according to a known method (see, for example, Helvetica Chimica Acta, Vol. 70, 175-186 (1987), WO2003/106468A1, Acta Nature, 6, 116-118 (2014), and Russian Journal of General Chemistry, Vol. 67, No. 1, 62-64 (1997)).

Step 2: Preparation of Compound [B-2]

The compound [B-2] can be prepared according to a known method by reacting a compound represented by the general formula [43] (hereinafter, referred to as "compound [43]") with the compound [42] to introduce a substituent containing a phosphorus atom into the hydroxyl group at the 3'-position of the 3'-terminal nucleoside unit.

In this step, an activator can also be used if necessary.

The solvent used in this step is not particularly limited, but examples thereof include acetonitrile and tetrahydrofuran.

The amount of the compound [42] is suitably 1 to 20 moles, and preferably 1 to 10 moles, per mole of the compound [43].

Examples of the "activator" include 1H-tetrazole, 5-ethylthiotetrazole, 4,5-dichloroimidazole, 4,5-dicyanoimidazole, benzotriazole triflate, imidazole triflate, pyridinium triflate, N,N-diisopropylethylamine, and 2,4,6-collidine/N-methylimidazole.

The amount of the "activator" is suitably 1 to 20 moles, and preferably 1 to 10 moles, per mole of the compound [43]

The reaction temperature is suitably 0° C. to 120° C.

The reaction time is different depending on the type of the raw material to be used, the reaction temperature, etc., but 30 minutes to 24 hours is usually suitable.

Although the compound [B-2] is a compound of which each nucleoside unit is the nucleoside unit [4e], a compound in which all or a part of the nucleoside units [4e] is replaced by the nucleoside unit [4f] or the nucleoside unit [4g] can also be prepared according to the same method as described above.

EXAMPLES

Hereinafter, the present invention is described in more detail in Examples, Comparative Examples, and Test Examples, but the present invention is not limited thereto.

The term "conversion yield (%)" means the ratio at which a raw material is converted to a target product, and is calculated by "{peak area (%) corresponding to target product detected by" high performance liquid chromatography (hereinafter, referred to as "HPLC")}÷{peak area (%) corresponding to raw material detected by HPLC+peak area (%) corresponding to target product detected by HPLC}×100.

Conditions of HPLC:

For a product, 0.5 mg of the product was dissolved in acetonitrile or 80% aqueous acetonitrile solution, HPLC analysis was performed under the following conditions, and the coupling efficiency was calculated by using the integral value of a peak area obtained by absorption at UV=264 nm by HPLC.

<ODS Conditions>

Column: Waters XBridge C8 (5 μm, 4.6×75 mm), 60° C.
Detection wavelength: 264 nm
Mobile phase A: 50 mM TEAA aq.
Mobile phase B: MeOH
Flow rate: 0.75 mL/min
Gradient: 70-95% B (0-20 min), 95% B (20-25 min), 70% B (25-35 min)

Conditions of LC/MS:

Equipment Used:

Ultra-high performance fluid chromatograph ACQUITY UPLC (Waters Corporation)
Quadrupole time-of-flight mass spectrometer SYNAPT-MS (Waters Corporation)
Column: YMC-Triart C8 1.9 μm, 2.1×50 mm (YMC)
Temperature: 50° C.
Flow rate: 0.4 mL/min
Mobile phase: 10 mM ammonia water
Mobile phase: MeOH
Gradient: 70-95% B (8 min)
Detector 1: UV 264 nm
Detector 2: Quadrupole time-of-flight mass spectrometer
Ionization method: ESI+
Measuring range: 100-2000 m/z Example 1: 4-(octadecylamino)-4-oxobutanoic acid [(2S,6R)-6-(5-methyl-2,4-dioxo-3,4-dihydropyrimidine-1(2H)-yl)morpholin-2-yl]methyl (Hereinafter, Referred to as "G1-suc-morT-OFF")

Step 1: Preparation of 4-(octadecylamino)-4-oxobutanoic acid (Hereinafter, Referred to as "G1-Suc")

Succinic anhydride (8.96 g, 1.1 eq.) and triethylamine (17 mL, 1.5 eq.) were added to a solution of octadecane-1-amine (21.94 g) in dichloromethane (500 mL), and the mixture was stirred at room temperature for 7 hours. The mixture was concentrated under reduced pressure, 150 mL of acetone was added to the residue, and the mixture was stirred for 16 hours. The precipitate was filtration under reduced pressure, washed with acetone (400 mL), and then dried under reduced pressure at 30° C. for 3 hours to obtain G1-suc (29.1 g, 96.6%) as white powder.

Step 2: Preparation of 4-(octadecylamino)-4-oxobutanoic acid [(2S,6R)-6-(5-methyl-2,4-dioxo-3,4-dihydropyrimidine-1(2H)-yl)morpholin-2-yl]methyl (Hereinafter, Referred to as "G1-suc-morT-OFF")

1-ethyl-3-(3-dimethylaminopropyl)carbodiimide hydrochloride (8.56 g, 1.2 eq.) was added to a solution of G1-suc (14.4 g) in tetrahydrofuran (150 mL), and the mixture was stirred at room temperature. Then, 1-((2R,6S)-6-(hydroxymethyl)-4-tritylmorpholin-2-yl)-5-methylpyrimidine-2,4(1H,3H)-dione (hereinafter, referred to a "morT-OH") (18 g, 1.0 eq.) and 4.57 g of 4-(N,N-dimethylamino)pyridine were added to the mixture, and the mixture was stirred in a water bath at 70° C. for 1 hour. The mixture was cooled to room temperature, then a 0.1 M aqueous solution of sodium dihydrogen phosphate was added to the mixture, and the mixture was stirred for a while. Then, the aqueous layer was removed, and the organic layer was washed once with a 0.1 M aqueous solution of sodium dihydrogen phosphate and once with brine diluted 2-fold with water. The aqueous layers were combined and extracted with dichloromethane, and the organic layers were combined and dried over anhydrous sodium sulfate. After filtration, the solvent was distilled off, and drying was performed under reduced pressure to obtain 4-(octadecylamino)-4-oxobutanoic acid [(2S,6R)-6-(5-methyl-2,4-dioxo-3,4-dihydropyrimidine-1(2H)-yl)-4-tritylmorpholin-2-yl]methyl (Hereinafter Referred to as "G1-suc-morT-ON") (white amorphous, 28.1 g, 89.5%). G1-suc-morT-ON was dissolved in 140 mL of dichloromethane, 20 mL of 2,2,2-trifluoroethanol and 10.3 mL of triisopropylsilane were added while stirring the mixture in an ice bath, and the mixture was stirred for a while. Then, 5.1 mL of trifluoroacetic acid was added dropwise to the mixture. One hour after the completion of the dropping, the reaction solution was poured into a solution obtained by adding ice to 100 mL of a saturated aqueous solution of sodium bicarbonate to cool the solution. After confirming that the aqueous layer had a pH of 7 to 8, extraction was performed on the aqueous layer using dichloromethane. The organic layers were combined, dried over anhydrous sodium sulfate, filtered, and concentrated. Column chromatography purification was performed with silica gel using a dichloromethane-methanol mixed solution as a mobile phase, and drying was performed under reduced pressure to obtain 19.89 g of G1-suc-morT-OFF as powder.

$^1$H-NMR ($CDCl_3$): δ8.90 (1H, bs); 7.25 (1H, d, J=1.6 Hz); 5.72 (1H, dd, J=9.6 Hz, 2.6 Hz); 5.65 (1H, m); 4.14 (2H, d, J=5.2 Hz); 3.98 (1H, m); 3.23 (2H, dd, J=12.8 Hz, 7.0 Hz); 3.12 (2H, dd, J=12 Hz, 2.6 Hz); 2.95 (2H, dd, J=12.8 Hz, 1.8 Hz); 2.60 to 2.75 (4H, m); 2.47 (2H, t, J=6.8 Hz); 1.95 (3H, d, J=1.6 Hz); 1.48 (2H, m), 1.21 to 1.34 (29H, m); 0.88 (3H, t, J=6.4 Hz) ESI-MS (+): 593.36 (M+H)

Example 2: Succinic acid {[(2S,6R)-6-(5-methyl-2,4-dioxo-3,4-dihydropyrimidine-1-yl)morpholin-2-yl]methyl}{2-octadecanoyloxy-1-[(octadecanoyloxymethyl)ethyl]_}(Hereinafter, Referred to as "G2-suc-morT-OFF")

Step 1: Preparation of 4-((1,3-bis(stearoyloxy)propan-2-yl)oxy)-4-oxobutanoic acid (Hereinafter, Referred to as "G2-suc")

Dichloromethane (8 mL) was added to 1 g (1.60 mmol) of 2-hydroxypropane-1,3-diyl distearate, then 176 mg (1.76 mmol) of succinic anhydride and 293 mg (2.40 mmol) of 4-(N,N,N-dimethylamino)pyridine were added to the mixture, and the mixture was stirred at room temperature for 16 hours. After completion of the reaction, a 1 M aqueous solution of sodium dihydrogen phosphate was added to the reaction solution, the solution was extracted with dichloromethane, the extract was dried over sodium sulfate, and the solvent was distilled off to obtain G2-suc (1.40 g).

Step 2: Preparation of succinic acid {[(2S,6R)-6-(5-methyl-2,4-dioxo-3,4-dihydropyrimidine-1-yl)-4-tritylmorpholin-2-yl]methyl}{2-octadecanoyloxy-1-[(octadecanoyloxymethyl)ethyl]} (Hereinafter, Referred to as "G2-suc-morT-ON")

Dichloromethane (5.2 mL) was added to G2-suc (900 mg, 1.24 mmol) and 277 mg (1.45 mmol) of 1-ethyl-3-(3-dimethylaminopropyl)carbodiimide hydrochloride, then 500 mg (1.03 mmol) of morT-OH and 132 mg (1.09 mmol) of 4-(N,N-dimethylamino)pyridine were added to the mixture, and the mixture was stirred at room temperature for 16 hours. After completion of the reaction, a 0.1 M aqueous solution of sodium dihydrogen phosphate was added to the reaction solution, the solution was extracted with dichloromethane, the extract was dried over sodium sulfate, and the solvent was distilled off. The obtained residue was purified by silica gel chromatography to obtain G2-suc-morT-ON (1.09 g, 89%).

$^1$H-NMR ($CDCl_3$): δ8.04 (1H, s); 7.17 to 7.51 (15H, m); 6.98 (1H, s); 6.12 (1H, dd, J=9.6 Hz, 2.4 Hz); 5.25 (1H, m); 4.34 to 4.37 (1H, m); 4.26 to 4.30 (2H, m); 4.11 to 4.16 (2H, m); 4.00 to 4.08 (2H, m); 3.35 (1H, d, J=11.2 Hz); 3.10 (1H, d, J=11.6 Hz); 2.60 (4H, s); 2.30 (4H, t, J=7.6 Hz); 1.83 (3H, s); 1.38 to 1.44 (2H, m); 1.24 (60H, m); 0.87 (6H, t, J=6.8 Hz)

Step 3: Preparation of G2-suc-morT-OFF

Dichloromethane (4.2 mL) was added to G2-suc-morT-ON, and the mixture was stirred at 0° C. Then, 127 μL (0.62 mmol) of triisopropylsilane and 64 μL (0.82 mmol) of trifluoroacetic acid were added to the mixture at 0° C., and the mixture was stirred at room temperature for 1 hour. After completion of the reaction, a saturated aqueous solution of sodium hydrogen carbonate was added to the reaction solution, the solution was extracted with dichloromethane, the extract was dried over sodium sulfate, and the solvent was distilled off. The obtained residue was purified by silica gel chromatography to obtain G2-suc-morT-OFF (373 mg, 95%).

$^1$H-NMR ($CDCl_3$): δ8.04 (1H, bs); 7.24 (1H, s); 5.70 (1H, d, J=2 Hz); 5.21 to 5.26 (1H, m); 4.28 to 4.31 (2H, m); 4.13 to 4.17 (4H, m); 3.96 to 4.00 (1H, m); 3.11 (1H, dd, J=12.4, 2 Hz); 2.94 (1H, dd, J=12.8, 2.4 Hz); 2.57 to 2.65 (6H, m); 2.32 (4H, t, J=7.6 Hz); 1.95 (3H, s); 1.25 (60H, m)); 0.88 (6H, t, J=7.6 Hz)

Example 3: [{(2S,6R)-6-(5-methyl-2,4-dioxo-3,4-dihydropyrimidine-1(2H)-yl)morpholin-2-yl}methyl]succinic acid 1,3-bis(oleoyloxy)propane-2-yl (Hereinafter, Referred to as "G3-suc-morT-OFF")

Step 1: Preparation of [{(2S,6R)-6-(5-methyl-2,4-dioxo-3,4-dihydropyrimidine-1(2H)-yl)-4-tritylmorpholin-2-yl}methyl]succinic acid 1,3-bis(oleoyloxy) propane-2-yl (Hereinafter, Referred to as "G3-suc-morT-ON")

Using 2-hydroxypropane-1,3-diyldiolate was used as a raw material, 4-((1,3-bis (oleoyloxy)propan-2-yl)oxy)-4-oxobutanoic acid (Hereinafter Referred to as "G3-suc") was obtained in the same manner as step 1 of Example 2. Then, G3-suc-morT-ON was obtained in the same manner as Step 2 of Example 2.

$^1$H-NMR ($CDCl_3$): δ8.00 (1H, s); 7.17 to 7.51 (15H, m); 6.99 (1H, s); 6.09 to 6.12 (1H, m); 5.29 to 5.38 (4H, m); 5.20 to 5.25 (1H, m); 4.33 to 4.37 (1H, m); 4.26 to 4.30 (2H, m); 4.12 to 4.16 (2H, m); 4.00 to 4.09 (2H, m); 3.35 (1H, d, J=11.6 Hz); 2.15 (1H, d, J=11.6 Hz); 2.60 (4H, m); 2.30 (4H, t, J=7.2 Hz); 1.97 to 2.02 (8H, m); 1.83 (3H, s); 1.57 to 1.61 (2H, m); 1.28 (44H, m); 0.89 (6H, t, J=6.8 Hz)

Step 2: Preparation of G3-suc-morT-OFF

G3-suc-morT-OFF was prepared in the same manner as Step 3 of Example 2.

$^1$H-NMR ($CDCl_3$): δ7.97 (1H, bs); 7.24 (1H, s); 5.69 to 5.72 (1H, m); 5.29 to 5.38 (4H, m); 5.21 to 5.25 (1H, m); 4.27 to 4.31 (2H, m); 4.13 to 4.17 (4H, m); 3.97 to 3.99 (1H, m); 3.11 (1H, d, J=12 Hz); 2.94 (1H, d, J=13.2 Hz); 2.57 to 2.67 (4H, m) 2.31 (4H, t, J=7.6 Hz); 1.99 to 2.00 (11H, m); 1.26 to 1.29 (46H, m); 0.87 (6H, t, J=6.8 Hz)

Example 4: 4-oxo-4-(4-stearoylpiperazine-1-yl)butanoic acid {(2S,6R)-6-(5-methyl-2,4-dioxo-3,4-dihydropyrimidine-1(2H)-yl)morpholin-2-yl}methyl (Hereinafter, Referred to as "G4-suc-morT-OFF")

Step 1: Preparation of 4-oxo-4-(4-stearoylpiperazine-1-yl)butanoic acid (Hereinafter, Referred to as "G4-suc")

26 mL of tetrahydrofuran was added to 1.68 g (5.91 mmol) of stearic acid, 1.13 g (5.91 mmol) of 1-ethyl-3-(3-dimethylaminopropyl)carbodiimide hydrochloride, and 0.79 g (5.91 mmol) of 1-hydroxybenzotriazole, then 1.45 mL (10.7 mmol) of triethylamine and 1 g (5.37 mmol) of piperazine-1-carboxylic acid tert-butyl were added to the mixture, and the mixture was stirred at room temperature for 16 hours. After completion of the reaction, a saturated aqueous solution of sodium hydrogen carbonate was added to the reaction solution, the solution was extracted with dichloromethane, the extract was dried over sodium sulfate, and the solvent was distilled off. The obtained residue was purified by silica gel chromatography to obtain 4-stearoylpiperazine-1-carboxylic acid tert-butyl (1.64 g; 67%). 18 mL of dichloromethane was added thereto, the mixture was stirred at 0° C., 2.77 mL (36.2 mmol) of trifluoroacetic acid was added to the mixture at 0° C., and the mixture was stirred at room temperature for 2 hours. After completion of the reaction, a saturated aqueous solution of sodium hydrogen carbonate was added to the reaction solution, the solution was extracted with dichloromethane, the extract was dried over sodium sulfate, and the solvent was distilled off to obtain 1-(piperazine-1-yl)octadecane-1-one (1.30 g). 18 mL of dichloromethane was added to 1.3 g (3.70 mmol) of the crude product, then 0.41 g (4.10 mmol) of succinic anhydride and 0.77 mL (5.50 mmol) of triethylamine were added to the mixture, and the mixture was stirred at room temperature for 2 hours. After completion of the reaction, the reaction solution was distilled off, acetone was added to the residue, and the residue was slurry washed at room temperature for 16 hours. The insoluble material was collected by filtration under reduced pressure, washed with acetone, and dried to obtain G4-suc (1.20 g).

Step 2: Preparation of 4-oxo-4-(4-stearoylpiperazine-1-yl)butanoic acid 1(2S,6R)-6-(5-methyl-2,4-dioxo-3,4-dihydropyrimidine-1(2H)-yl)-4-tritylmorpholin-2-yl}methyl (Hereinafter, Referred to as "G4-suc-morT-ON")

Tetrahydrofuran (10 mL) was added to G4-suc (982 mg, 2.17 mmol) and 555 mg (2.90 mmol) of 1-ethyl-3-(3-dimethylaminopropyl)carbodiimide hydrochloride, and the mixture was stirred at 70° C. Then, morT-OH (1 g, 2.07 mmol) and 265 mg (2.17 mmol) of 4-(N,N-dimethylamino)pyridine were added to the mixture, and the mixture was stirred at 70° C. for 30 minutes. After completion of the reaction, the reaction solution was allowed to cool to room temperature, a 0.1 M aqueous solution of sodium dihydrogen phosphate was added to the reaction solution, the solution was extracted with dichloromethane, the extract was dried over sodium sulfate, and the solvent was distilled off. The obtained residue was purified by silica gel chromatography to obtain G4-suc-morT-ON (1.68 g, 89%).

$^1$H-NMR ($CDCl_3$): δ8.00 (1H, s); 7.16 to 7.50 (15H, m); 6.97 (1H, s); 6.10 (1H, d, J=8 Hz); 4.34 to 4.36 (1H, m); 4.04 (2H, d, J=4.8 Hz); 3.57 to 3.64 (4H, m); 3.44 to 3.48 (4H, m); 3.32 to 3.34 (1H, m); 3.09 to 3.12 (1H, m); 2.60 to 2.64 (4H, m); 2.31 (2H, t, J=7.6 Hz); 1.82 (3H, s); 1.23 to 1.42 (32H, m); 0.86 (3H, t, J=6.8)

Step 3: Preparation of G4-suc-morT-OFF

G4-suc-morT-OFF was prepared in the same manner as Step 3 of Example 2.

$^1$H-NMR ($CDCl_3$): δ8.32 (1H, bs); 7.23 (1H, s); 5.67 to 5.70 (1H, m); 4.12 to 4.19 (2H, m); 3.96 to 4.01 (1H, m); 3.47 to 3.67 (8H, m); 3.10 to 3.13 (1H, m); 2.95 to 2.98 (1H, m); 2.60 to 2.72 (4H, m); 2.33 (2H, t, J=7.2 Hz); 1.95 (3H, s); 1.25 to 1.31 (32H, m); 0.88 (3H, t, J=7.6 Hz)

Example 5: 4-(octadecylcarbamoyl)benzoic acid [(2S,6R)-6-(5-methyl-2,4-dioxo-3,4-dihydropyrimidine-1(2H)-yl)morpholin-2-yl]methyl (Hereinafter, Referred to as "G5-tpa-morT-OFF")

Step 1: Preparation of 4-(octadecylcarbamoyl)benzoic acid [(2S,6R)-6-(5-methyl-2,4-dioxo-3,4-dihydropyrimidine-1(2H)-yl)-4-tritylmorpholin-2-yl]methyl (Hereinafter, Referred to as "G5-tpa-morT-ON")

G5-tpa-morT-ON was prepared in the same manner as Step 2 of Example 2, using 4-(octadecylcarbamoyl)benzoic acid.

$^1$H-NMR ($CDCl_3$): δ8.24 (1H, s); 7.97 (2H, d, J=8 Hz); 7.77 (2H, d, J=8 Hz); 7.17 to 7.46 (15H, m); 6.95 (1H, s); 6.12 to 6.16 (1H, m); 4.49 to 4.51 (1H, m); 4.25 to 4.33 (2H, m); 3.42 to 3.47 (2H, m); 3.35 to 3.38 (1H, m); 3.21 to 3.24 (1H, m); 1.79 (3H, s); 1.23 to 1.44 (34H, m); 0.86 (3H, t, J=6.8 Hz)

Step 2: Preparation of G5-tpa-morT-OFF

G5-tpa-morT-OFF was prepared in the same manner as Step 3 of Example 2.

$^1$H-NMR ($CDCl_3$): δ8.24 (1H, bs); 8.11 (2H, d, J=8.4 Hz); 7.84 (2H, d, J=8.4 Hz); 7.24 (1H, s); 6.14 to 6.17 (1H, m); 5.74 to 5.77 (1H, m); 4.40 to 4.45 (2H, m); 4.13 to 4.19 (1H, m); 3.45 to 3.50 (2H, m); 3.14 to 3.18 (1H, m); 3.05 to 3.08 (1H, m); 1.93 (3H, s); 1.26 to 1.41 (34H, m); 0.89 (3H, t, J=7.6 Hz)

Example 6: 4-(4-(4-(octadecylcarbamoyl)benzoyl)piperazine-1-yl)-4-oxobutanoic acid {(2S,6R)-6-(5-methyl-2,4-dioxo-3,4-dihydropyrimidine-1(2H)-yl)morpholin-2-yl}methyl (Hereinafter Referred to as "G6-suc-morT-OFF")

Step 1: Preparation of 4-(4-(4-(octadecylcarbamoyl)benzoyl)piperazine-1-yl)-4-oxobutanoic acid (Hereinafter Referred to as "G6-suc")

G6-suc was prepared in the same manner as Step 1 of Example 4, using 4-(octadecylcarbamoyl)benzoic acid instead of stearic acid.

Step 2: Preparation of 4-[4-{4-(octadecylcarbamoyl)benzoyl}piperazine-1-yl]-4-oxobutanoic acid {(2S,6R)-6-(5-methyl-2,4-dioxo-3,4-dihydropyrimidine-1 (2H)-yl)-4-tritylmorpholin-2-yl}methyl (Hereinafter Referred to as "G6-suc-morT-ON")

G6-suc-morT-ON was prepared in the same manner as Step 2 of Example 2.

$^1$H-NMR ($CDCl_3$): δ8.08 (1H, bs); 7.81 (2H, d, J=7.6 Hz); 7.16 to 7.50 (17H, m); 6.97 (1H, s); 6.08 to 6.10 (1H, m); 4.33 to 4.39 (1H, m); 4.02 to 4.04 (2H, m); 3.31 to 3.79 (11H, m); 3.08 to 3.11 (1H, m); 2.60 to 2.69 (4H, m); 1.81 (3H, s); 1.23 to 1.44 (34H, m); 0.86 (3H, t, J=6.4 Hz)

Step 3: Preparation of G6-suc-morT-OFF 4.6 mL of dichloromethane and 0.4 mL of 2,2,2-trifluoroethanol were added to 493 mg (0.47 mmol) of G6-suc-morT-ON, and the mixture was stirred at 0° C. Then, 145 μL (0.70 mmol) of triisopropylsilane and 53 μL (0.70 mmol) of trifluoroacetic acid were added to the mixture at 0° C., and the mixture was stirred at room temperature for 1 hour. After completion of the reaction, a saturated aqueous solution of sodium hydrogen carbonate was added to the reaction solution, the solution was extracted with dichloromethane, the extract was dried over sodium sulfate, and the solvent was distilled off. The obtained residue was purified by silica gel chromatography to obtain G6-suc-morT-OFF (372 mg; 98%).

$^1$H-NMR ($CDCl_3$): δ8.05 (1H, bs); 7.79 (2H, d, J=7.6 Hz); 7.45 (2H, d, J=7.6 Hz); 7.23 (1H, s); 6.08 to 6.11 (1H, m); 5.67 to 5.69 (1H, m); 4.10 to 4.15 (2H, m); 3.96 to 3.99 (1H, m); 3.36 to 3.79 (8H, m); 3.08 to 3.11 (1H, m); 2.93 to 2.96 (1H, m); 2.57 to 2.70 (6H, m); 1.92 (3H, s); 1.23 to 1.38 (34H, m); 0.86 (3H, t, J=7.2 Hz)

Example 7: 3,4,5-tris(octadecyloxy)benzoic acid {(2S,6R)-6-(5-methyl-2,4-dioxo-3,4-dihydropirimidine-1(2H)-yl)morpholin-2-yl}methyl (Hereinafter Referred to as "G7-morT-OFF")

Step 1: Preparation of 3,4,5-tris(octadecyloxy)benzoic acid {(2S,6R)-6-(5-methyl-2,4-dioxo-3,4-dihydropyrimidine-1(2H)-yl)-4-tritylmorpholin-2-yl}methyl (Hereinafter Referred to as "G7-morT-ON")

G7-morT-ON was prepared in the same manner as Step 2 of Example 2, using 3,4,5-trioctadecoxybenzoic acid.

$^1$H-NMR ($CDCl_3$): δ7.90 (1H, bs); 7.12 to 7.45 (17H, m); 6.97 (1H, s); 6.12 to 6.14 (1H, m); 4.46 to 4.51 (1H, m); 4.28 to 4.32 (1H, m); 4.16 to 4.20 (1H, m); 3.90 to 4.00 (6H, m); 3.37 to 3.40 (1H, m); 3.22 to 3.25 (1H, m); 1.78 to 1.82 (5H, m); 1.23 to 1.50 (96H, m); 0.86 (9H, t, J=6.8 Hz)

Step 2: Preparation of G7-morT-OFF

G7-morT-OFF was prepared in the same manner as Step 3 of Example 2.

$^1$H-NMR ($CDCl_3$): δ7.98 (1H, bs); 7.22 (3H, m); 5.69 to 5.72 (1H, m); 4.32 to 4.36 (2H, m); 4.08 to 4.12 (1H, m); 3.94 to 4.01 (6H, m); 3.11 to 3.14 (1H, m); 3.02 to 3.05 (1H, m); 2.64 to 2.72 (2H, m); 1.90 (3H, m); 1.23 to 1.45 (96H, m)0.86 (9H, t, J=7.2 Hz)

Example 8: Succinic acid {(2S,6R)-6-(5-methyl-2,4-dioxo-3,4-dihydropyrimidine-1 (2H)-yl)morpholin-2-yl} methyl (2-[{3,4,5-tris(octadecyloxy) benzoyloxy}oxy]ethyl) (Hereinafter Referred to as "G8-suc-morT-OFF")

Step 1: Preparation of 2-hydroxyethyl 3,4,5-trioctadecyloxybenzoate 8.1 mL of chloroform was added to 1.5 g (1.60 mmol) of 3,4,5-trioctadecyloxy benzoic acid, 370 mg (1.90 mmol) of 1-ethyl-3-(3-dimethylaminopropyl)carbodiimide hydrochloride, and 240 mg (1.90 mmol) of 4-(N,N-dimethylamino)pyridine, then 120 mg (1.90 mmol) of ethylene glycol was added to the mixture, and the mixture was stirred at room temperature for 3 hours. After completion of the reaction, a 1 M aqueous solution of sodium dihydrogen phosphate was added to the reaction solution, the solution was extracted with dichloromethane, the extract was dried over sodium sulfate, and the solvent was distilled off. The obtained residue was purified by silica gel chromatography to obtain 2-hydroxyethyl 3,4,5-trioctadecyloxybenzoate (882 mg; 56%).

$^1$H-NMR ($CDCl_3$): δ7.26 (2H, s); 4.45 to 4.47 (2H, m); 3.95 to 4.03 (8H, m); 1.25 to 1.52 (96H, m); 0.88 (9H, t, J=7.2 Hz)

Step 2: Preparation of succinic acid {(2S,6R)-6-(5-methyl-2,4-dioxo-3,4-dihydropyrimidine-1(2H)-yl)-4-tritylmorpholin-2-yl}methyl (2-[{3,4,5-tris(octadecyloxy)benzoyloxy}oxy]ethyl) (Hereinafter Referred to as "G8-suc-morT-ON")

4-oxo-4-(2-[{3,4,5-tris(octadecyloxy)benzoyl}oxy] ethoxy)butanoic acid (hereinafter referred to as "G8-suc") was obtained in the same manner as Step 1 of Example 2, and then G8-suc-morT-ON was obtained in the same manner as Step 2 of Example 2.

$^1$H-NMR ($CDCl_3$): δ7.87 (1H, bs); 7.12 to 7.43 (17H, m); 6.97 (1H, s); 6.07 to 6.10 (1H, m); 4.33 to 4.46 (5H, m); 3.91 to 4.07 (8H, m); 3.31 to 3.34 (1H, m); 3.07 to 3.10 (1H, m); 2.56 to 2.60 (4H, m); 1.68 to 1.80 (5H, m); 1.23 to 1.50 (96H, m); 0.86 (9H, t, J=7.2 Hz)

Step 3: Preparation of G8-suc-morT-OFF

G8-suc-morT-OFF was obtained in the same manner as Step 3 of Example 2.

$^1$H-NMR ($CDCl_3$): δ7.96 (1H, bs); 7, 23 (3H, m); 5.67 to 5.69 (1H, m); 4.40 to 4.47 (5H, m); 3.94 to 4.11 (8H, m); 3.09 to 3.12 (1H, m); 2.89 to 2.92 (1H, m); 2.53 to 2.65 (6H, m); 1.90 (3H, s); 1.23 to 1.45 (96H, m); 0.86 (9H, t, J=6.8 Hz)

Example 9: 4-(dioctadecylamino)-4-oxobutanoic acid {(2S,6R)-6-(5-methyl-2,4-dioxo-3A,4-dihydropyrimidine-1(2H)-yl)morpholin-2-yl} methyl (Hereinafter, Referred to as "G9-suc-morT-OFF")

Step 1: Preparation of 4-(dioctadecylamino)-4-oxobutanoic acid {(2S,6R)-6-(5-methyl-2,4-dioxo-3,4-dihydropyrimidine-1(2H)-yl)-4-tritylmorpholin-2-yl} methyl (Hereinafter, Referred to as "G9-suc-morT-ON")

4-(dioctadecylamino)-4-oxobutanoic acid (hereinafter referred to as "G9-suc") was prepared in the same manner as Step 1 of Example 2, using N-octadecane-1-amine as a raw material. Then, G9-suc-morT-ON was prepared in the same manner as Step 2 of Example 2.

$^1$H-NMR ($CDCl_3$): δ7.88 (1H, bs); 7.17 to 7.43 (15H, m); 6.98 (1H, s); 6.06 to 6.09 (1H, m); 4.31 to 4.35 (1H, m); 4.01 to 4.03 (2H, m); 3.08 to 3.34 (8H, m); 2.52 to 2.64 (4H, m); 1.82 (3H, s); 1.23 to 1.52 (64H, m); 0.85 (6H, t, J=6.8 Hz)

Step 2: Preparation of G9-suc-morT-OFF

G9-suc-morT-OFF was prepared in the same manner as Step 3 of Example 2.

$^1$H-NMR ($CDCl_3$): δ8.14 (1H, bs); 7.27 (1H, s); 5.68 to 5.72 (1H, m): 4.12 to 4.20 (2H, m); 3.98 to 4.01 (1H, m); 3.10 to 3.29 (5H, m); 2.94 to 2.97 (1H, m); 2.60 to 2.70 (6H, m); 1.95 (3H, s); 1.25 to 1.49 (64H, m); 0.88 (6H, t, J=7.2 Hz)

Example 10: 4-[{1-(octadecylamino)-1-oxo-3-phenylpropane-2-yl}amino]-4-oxobutanoic acid {(2S, 6R)-6-(5-methyl-2,4-dioxo-3,4-dihydropyrimidine-1 (2H)-yl)morpholin-2-yl}methyl (Hereinafter, Referred to as "G10-suc-morT-OFF")

Step 1: Preparation of 4-[{1-(octadecylamino)-1-oxo-3-phenylpropane-2-yl}amino]-4-oxobutanoic acid 1(2S,6R)-6-(5-methyl-2,4-dioxo-3,4-dihydropyrimidine-1(2H)-yl)-4-tritylmorpholin-2-yl}methyl (Hereinafter, Referred to as "G10-suc-morT-ON")

9.4 mL of tetrahydrofuran was added to 500 mg (1.88 mmol) of 2-tert-butoxycarbonylamino-3-phenyl-propanoic acid, then 652 μL (3.77 mmol) of N-ethyl-N-isopropyl-propane-2-amine, 46 mg (0.38 mmol) of 4-(N,N-dimethyl-amino)pyridine, and 505 mg (2.64 mmol) of 1-ethyl-3-(3-dimethylaminopropyl)carbodiimide hydrochloride were added to the mixture, and the mixture was stirred at room temperature for 5 hours. After completion of the reaction, a 1 M aqueous solution of sodium dihydrogen phosphate was added to the reaction solution, the solution was extracted with dichloromethane, the extract was dried over sodium sulfate, and the solvent was distilled off. The obtained residue was purified by silica gel chromatography to obtain tert-butoxycarbonylamino-N-octadecyl-3-phenyl-propanamide (779 mg, 80%).

$^1$H-NMR ($CDCl_3$): δ7.18 to 7.28 (5H, m); 5.57 (1H, bs); 5.06 (1H, bs); 4.20 to 4.26 (1H, m); 2.95 to 3.12 (4H, m); 1.40 (9H, s); 1.14 to 1.28 (32H, m); 0.86 (3H, t, J=6.8 Hz)

15 mL of dichloromethane was added to 779 mg (1.51 mmol) of tert-butoxycarbonylamino-N-octadecyl-3-phenyl-propanamide, then 1.74 mL (22.61 mmol) of trifluoroacetic acid was added to the mixture, and the mixture was stirred at room temperature for 3 hours. After completion of the reaction, the solvent was distilled off to obtain 2-amino-N-octadecyl-3-phenyl-propanamide (620 mg). The same reaction as in Step 1 of Example 2 was carried out on the crude product to prepare G10-suc. Then, the same reaction as in Step 2 of Example 2 was carried out to prepare G10-suc-morT-ON.

$^1$H-NMR ($CDCl_3$): δ8.08 (1H, bs); 7.16 to 7.32 (20H, m); 6.98 (1H, s); 6.29 to 6.31 (1H, m); 6.10 to 6.12 (1H, m); 5.56 to 5.59 (1H, m); 4.51 to 4.57 (1H, m); 4.35 to 4.37 (1H, m); 4.02 (2H, d, J=5.6 Hz); 3.73 to 3.77 (1H, m); 2.92 to 3.33 (6H, m); 2.39 to 2.67 (4H, m); 1.84 (3H, s); 1.21 to 1.45 (32H, m); 0.88 (3H, t, J=7.6 Hz)

Step 2: Preparation of G10-suc-morT-OFF

The target product was obtained in the same manner as Step 3 of Example 2.

$^1$H-NMR ($CDCl_3$): δ8.33 (1H, bs); 7.16 to 7.32 (6H, m); 6.38 to 6.40 (1H, m); 5.67 to 5.71 (2H, m); 4.54 to 4.58 (1H, m); 4.08 to 4.16 (3H, m); 3.94 to 4.01 (1H, m); 2.91 to 3.17 (5H, m); 2.46 to 2.79 (5H, m); 1.94 (3H, s); 1.13 to 1.36 (32H, m); 0.88 (3H, t, J=7.6 Hz)

Table 3 below shows the chemical structural formulae of the compounds described above in Examples 1 to 10.

TABLE 3

| Abbreviation | Chemical structure |
|---|---|
| G1-suc-morT-OFF | 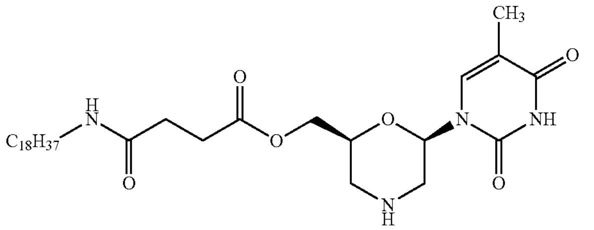 |
| G2-suc-morT-OFF | 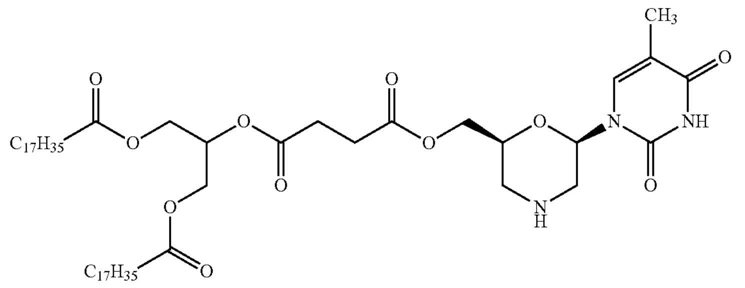 |

TABLE 3-continued
| Abbreviation | Chemical structure |
| --- | --- |
| G3-suc-morT-OFF | 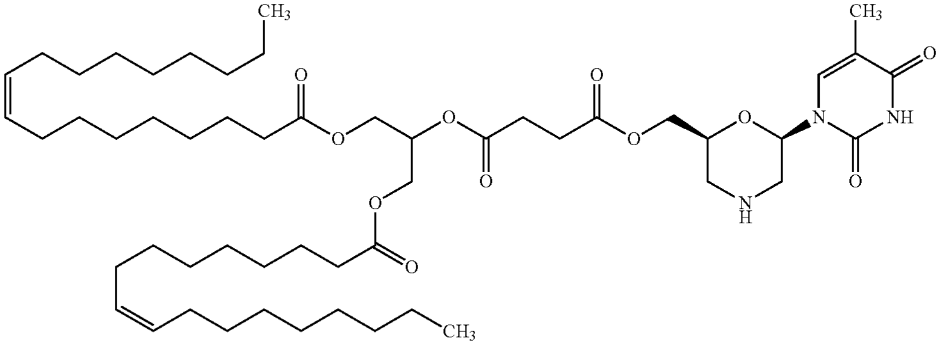 [SMILES: CCCCCCCC/C=C\CCCCCCCC(=O)OCC(COC(=O)CCCCCCC/C=C\CCCCCCCC)OC(=O)CCC(=O)OC[C@@H]1CNC[C@H](n2cc(C)c(=O)[nH]c2=O)O1] |
| G4-suc-morT-OFF | 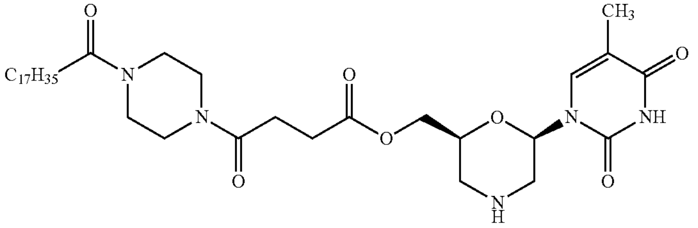 |
| G5-tpa-morT-OFF | 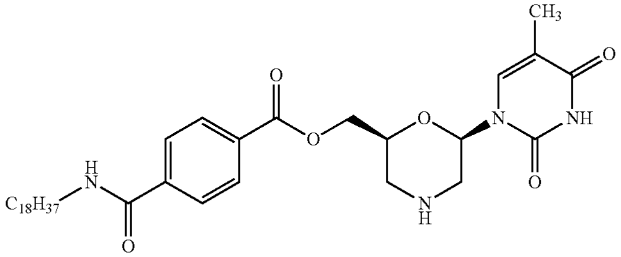 |
| G6-suc-morT-OFF | 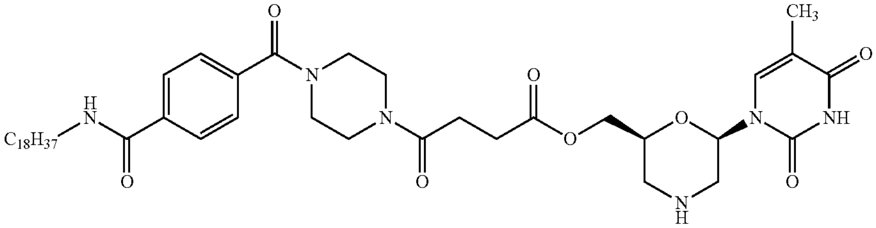 |
| G7-morT-OFF | 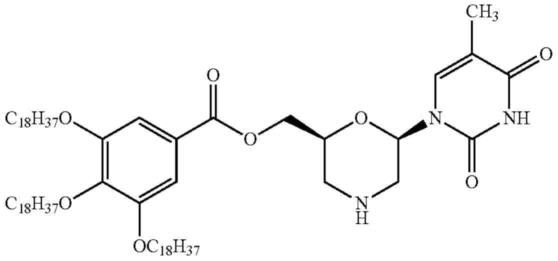 |

TABLE 3-continued
| Abbreviation | Chemical structure |
| --- | --- |
| G8-suc-morT-OFF | 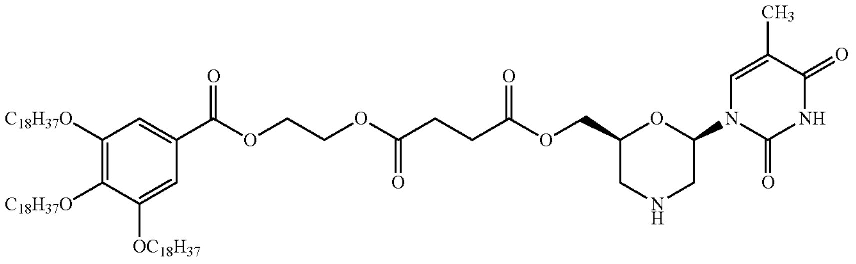 |
| G9-suc-morT-OFF | 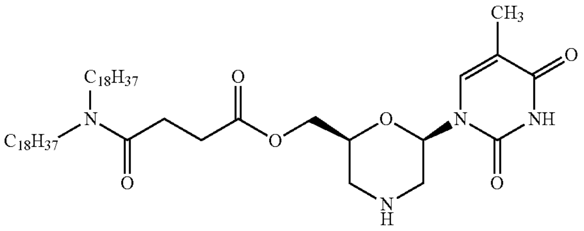 |
| G10-suc-morT-OFF | 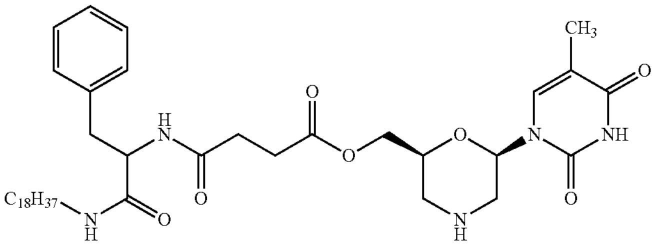 |
Example 11: Preparation of G1-suc-PMO[$A^{Bz}$-$A^{Bz}$]-ON (Tetrabutylammonium Chloride was Used as a Reaction Accelerator, Reaction Time (30 Minutes))
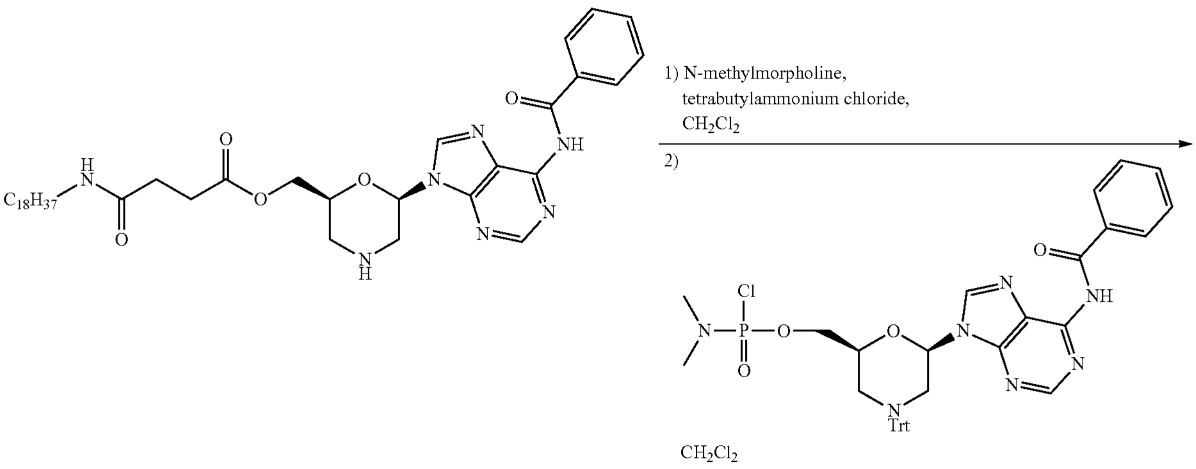

-continued

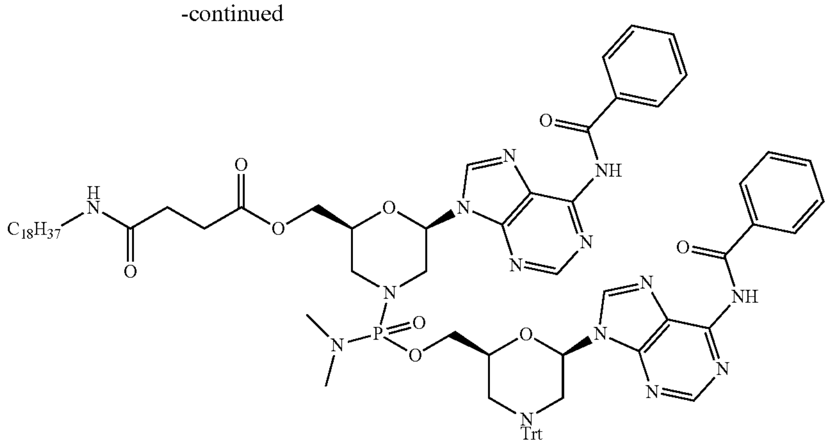

G1-suc-morA-OFF (14.1 mg, 0.02 mmol), N-ethylmorpholine (7.6 μL, 0.06 mmol) and tetrabutylammonium chloride (16.7 mg, 0.06 mmol) were dissolved in 200 μL of dichloromethane. morA (21.7 mg, 0.03 mmol) in dichloromethane (200 μL) was added, and the mixture was shaken at 40° C. for 30 minutes. After 30 minutes, 160 μL of 1% 1-methylpiperazine in dichloromethane was added to 40 μL of the reaction solution to quench the reaction. This solution was further diluted 10-fold with acetonitrile and analyzed by HPLC (raw material Rt: 13.20 min, target product Rt: 19.68 min, conversion yield 99.4%). ESI-TOF-MS(+): found: 1391.91 (M+H), calcd: 1390.71. G1-suc-morA-OFF: ((2S, 6R)-6-(6-benzamido-9H-purin-9-yl) morpholin-2-yl)methyl 4-(octadecylamino)-4-oxobutanoate G1-suc-morA-OFF was prepared in the same manner as Step 2 of Example 1, using N-(9-((2R,6S)-6-(hydroxymethyl-4-tritylmorforin-2-yl)-9H-purin-6-yl)benzamide (morA-OH) instead of morT-OH.

Example 12: Preparation of G1-suc-PMO[$A^{Bz}$-T]-ON (1-butyl-1-methylpyrrolidinium chloride was Used as a Reaction Accelerator, Reaction Time (60 Minutes))

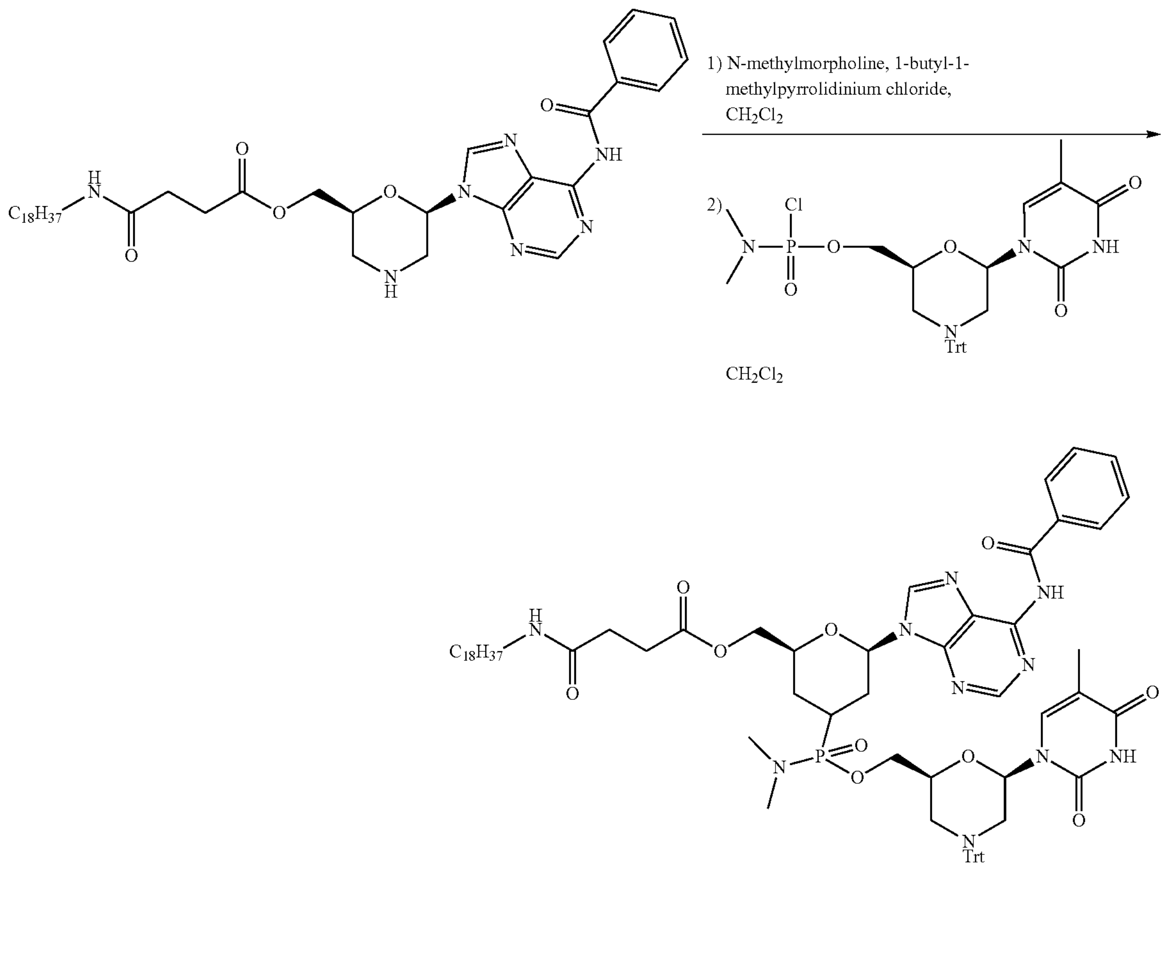

G1-suc-morA-OFF (10 mg, 0.0142 mmol), morT (12.9 mg, 0.0212 mmol), N-ethylmorpholine (5.38 μL, 0.0425 mmol) and 1-butyl-1-methylpyrrolidinium chloride (7.55 mg, 0.0425 mmol) were dissolved in 283 μL of dichloromethane and stirred at room temperature for 60 minutes. After 60 minutes, 4.71 μL (0.0425 mmol) of 1-methylpiperazine was added to quench the reaction. The solution was diluted 60-fold with acetonitrile and analyzed by HPLC (raw material Rt: 13.21 min, target product Rt: 18.77 min, conversion yield 99.7%). ESI-TOF-MS(+): found: 1278.76 (M+H), calcd: 1277.68.

Example 13: Preparation of G1-suc-PMO[$A^{Bz}$-$G^{CE,Pac}$-T-T-T-$C^{Bz}$-T-T]-OFF (1-butyl-1-methylpyrrolidinium chloride was Used as a Reaction Accelerator)

Liquids a and b (shown below) were supplied at 0.05 mL/min and 0.2 mL/min, respectively, and mixed together in a 30 mL tube reactor, and the reaction was carry out at 40° C. for 120 minutes. After the reaction, Solution c (shown below) was supplied to the mixture at 0.6 mL/min and mixed together, and the reaction was carried out at 40° C. for 5.9 minutes in a 5 mL tube reactor. Then, Solution d (shown below) was supplied to the mixture at 0.85 mL/min and mixed together, and the mixture was collected in a dropping funnel. The organic layer in the dropping funnel was supplied at 0.8 mL/min and Solution e (shown below) was supplied at 0.4 mL/min and mixed together, and the reaction was carried out in a 15.6 mL tube reactor at room temperature for 13 minutes. After the reaction, Liquid f (shown below) was supplied at a flow rate of 1.5 mL/min to the mixture, and the mixture was collected in a separating funnel. The collected organic layer was washed with Liquid g (shown below) and saturated aqueous sodium hydrogen carbonate, dried over sodium sulfate, and the solvent was distilled off. The residue was dissolved in a small amount of dichloromethane, and diisopropyl ether was added to obtain a precipitate, which was filtered and dried under reduced pressure overnight to obtain G1-suc-PMO[$A^{Bz}$-$G^{CE,Pac}$-T-T-T-$C^{Bz}$-T-T]-OFF (white solid, 2.53 g). A small amount of the solid was dissolved in dichloromethane, diluted with a mixed solvent of methanol and acetonitrile (1:1) and analyzed by HPLC (raw material Rt: 13.19 min, target product Rt: 12.84 min, conversion yield 96.7%). ESI-TOF-MS(+): found: 3317.39 (M+H), calcd: 3317.32.

Solution a: morT (3.17 g, 5.2 mmol) dissolved in dichloromethane (5 mL).

Solution b: G1-suc-PMO[$A^{Bz}$-$G^{CE,Pac}$-T-T-T-$C^{Bz}$-T]-OFF (2.94 g, 0.984 mmol), N-ethylmorpholine (373 μL, 2.95 mmol) and 1M of 1-butyl-1-methylpyrrolidinium chloride in dichloromethane (2.95 mL, 2.95 mmol) dissolved in a mixed solution of 1,3-dimethyl-2-imidazolidinone (1.36 mL) and dichloromethane (6.09 mL).

Solution c: 1-methylpiperazine (3.33 mL, 30 mmol) dissolved in dichloromethane (96.7 mL).

Solution d: 1:1 mixture of 1M aqueous sodium dihydrogen phosphate and brine added with 5% by volume of ethanol.

Solution e: mixture of trifluoroacetic acid (4 mL), ethanol (1 mL), triethylamine (1 mL), trifluoroethanol (30 mL) and dichloromethane (64 mL).

Liquid f: 1:1 mixture of brine and water.

Liquid g: 1:1 mixture of 1% aqueous trifluoroacetic acid and brine added with 5% by volume of ethanol.

Example 14: Preparation of G1-suc-PMO [T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$]-ON using a Reaction Accelerator (1-butyl-1-methylpyrrolidinium chloride: BMPC) and a Solvent (1,3-dimethyl-2-imidazolidinone/dichloromethane) (1-butyl-1-methylpyrrolidinium chloride was Used as a Reaction Accelerator, 1,3-dimethyl-2-imidazolidinone/dichloromethane was Used as a Solvent, Reaction Time (120 Minutes))

G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T]-OFF (1.26 g, 0.213 mmol), morA (230 mg, 0.319 mmol), N-ethylmorpholine (81 μL, 0.638 mmol) and 1-butyl-1-methylpyrrolidinium chloride (113 mg, 0.638 mmol) were dissolved in 7.1 mL of 1,3-dimethyl-2-imidazolidinone/dichloromethane solution and stirred at 40° C. for 120 minutes. After 120 minutes, 1-methylpiperazine (71 μL, 0.638 mmol) was added to quench the reaction. The solution was diluted 60-fold with an 80% aqueous acetonitrile solution and analyzed by HPLC (raw material Rt: 15.16 min, target product Rt: 18.49, 18.72 min, conversion yield 97.8%).

Preparation of G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$-T]-ON (1-butyl-1-methylpyrrolidinium chloride was Used as a Reaction Accelerator, 1,3-dimethyl-2-imidazolidinone/dichloromethane was Used as a Solvent, Reaction Time (120 Minutes))

G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$]-OFF (1.17 g, 0.209 mmol), morT (191 mg, 0.314 mmol), N-ethylmorpholine (79 μL, 0.628 mmol) and 1-butyl-1-methylpyrrolidinium chloride (186 mg, 1.05 mmol) were dissolved in 7.0 mL of 1,3-dimethyl-2-imidazolidinone/dichloromethane and stirred at 40° C. for 120 minutes. After 120 minutes, 1-methylpiperazine (70 μL, 0.628 mmol) was added to quench the reaction. The solution was diluted 60-fold with an 80% aqueous acetonitrile solution and analyzed by HPLC (raw material Rt: 15.18 min, target product Rt: 18.17 min, conversion yield 99.6%).

Preparation of G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$-T-$A^{Bz}$]-ON (1-butyl-1-methylpyrrolidinium chloride was Used as a Reaction Accelerator, 1,3-dimethyl-2-imidazolidinone/dichloromethane was used as a solvent, reaction time (120 minutes))

G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$-T]-OFF (1.08 g, 0.182 mmol), morA (198 mg, 0.274 mmol), N-ethylmorpholine (69 μL, 0.547 mmol) and 1-butyl-1-methylpyrrolidinium chloride (162 mg, 0.912 mmol) were dissolved in 6.1 mL of 1,3-dimethyl-2-imidazolidinone/dichloromethane and stirred at 40° C. for 120 minutes. After 120 minutes, 1-methylpiperazine (61 μL, 0.547 mmol) was added to quench the reaction. The solution was diluted 60-fold with an 80% aqueous acetonitrile solution and analyzed by HPLC (raw material Rt: 15.02 min, target product Rt: 18.12, 18.32 min, conversion yield 99.4%). ESI-TOF-MS (+): found: 6362.332, calcd: 6362.320

Example 15: Preparation of G-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$]-ON using a reaction accelerator (1-butyl-1-methylpyrrolidinium chloride: BMPC) and a Solvent (Dichloromethane) (1-butyl-1-methylpyrrolidinium chloride was Used as a Reaction Accelerator, Dichloromethane was Used as a Solvent, Reaction Time (120 Minutes))

G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T]-OFF (2.14 g, 0.361 mmol), morA (391 mg, 0.542 mmol), N-ethylmorpholine (137 μL, 1.08 mmol)) and 1-butyl-1-methylpyrrolidinium chloride (193 mg, 1.08 mmol) were dissolved in 12 mL of dichloromethane and stirred at 40° C. for 120 minutes. After 120 minutes, 1-methylpiperazine (120 μL, 1.08 mmol) was added to quench the reaction. The solution was diluted 60-fold with an 80% aqueous acetonitrile solution and analyzed by HPLC (raw material Rt: 15.16 min, target product Rt: 18.49, 18.72 min, conversion yield 97.8%).

Preparation of G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$-T]-ON (1-butyl-1-methylpyrrolidinium chloride was Used as a Reaction Accelerator, Dichloromethane was Used as a Solvent, Reaction Time (120 Minutes))

G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$]-OFF (2.0 g, 0.357 mmol), morT (326 mg, 0.536 mmol), N-ethylmorpholine (136 μL, 1.07 mmol) and 1-butyl-1-methylpyrrolidinium chloride (318 mg, 1.79 mmol) were dissolved in 11.9 mL of dichloromethane and stirred at 40° C. for 120 minutes. After 120 minutes, 1-methylpiperazine (119 μL, 1.07 mmol) was added to quench the reaction. The solution was diluted 60-fold with an 80% aqueous acetonitrile solution and analyzed by HPLC (raw material Rt: 15.18 min, target product Rt: 18.17 min, conversion yield 99.7%).

Preparation of G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$-T-$A^{Bz}$]-ON (1-butyl-1-methylpyrrolidinium chloride was used as a reaction accelerator, dichloromethane was Used as a Solvent, Reaction Time (120 Minutes))

G1-suc-PMO[T-$G^{CE,Pac}$-$G^{CE,Pac}$-$G^{CE,Pac}$-$A^{Bz}$-T-$C^{Bz}$-$C^{Bz}$-$A^{Bz}$-$G^{CE,Pac}$-T-$A^{Bz}$-T]-OFF (1.90 g, 0.321 mmol), morA (348 mg, 0.481 mmol), N-ethylmorpholine (122 μL, 0.962 mmol) and 1-butyl-1-methylpyrrolidinium chloride (285 mg, 1.60 mmol) were dissolved in 10.7 mL of dichloromethane and stirred at 40° C. for 120 minutes. After 120 minutes, 1-methylpiperazine (107 μL, 0.962 mmol) was added to quench the reaction. The solution was diluted 60-fold with an 80% aqueous acetonitrile solution and analyzed by HPLC (raw material Rt: 15.02 min, target product Rt: 18.12, 18.32 min, conversion yield 97.0%).

The invention claimed is:

1. A method for producing a compound [C] of the following formula

[C]

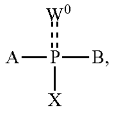

comprising:

subjecting a compound [A] having a hydroxyl group or a primary or secondary amino group to a condensation reaction with a compound [B] having a substituent group containing a phosphorous atom of formula [1]:

[1]

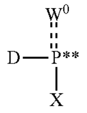

wherein

** represents a binding position,

D represents a halogen, 5- to 6-membered saturated cyclic amino, or di($C_{1-6}$ alkyl)amino, $W^0$ represents a lone pair of electrons, an oxygen atom, or a sulfur atom, and X represents a hydroxyl group substituted with a removable group under a neutral condition, 1,1,3,3-tetra($C_{1-6}$ alkyl)guanidyl, $C_{1-6}$ alkoxy, di($C_{1-6}$ alkyl)amino, mono (amino-$C_{1-6}$ alkyl substituted with a removable group under a basic condition)amino, di(amino-$C_{1-6}$ alkyl substituted with a removable group under a basic condition)amino, or a substituent represented by formula [2]:

[2]

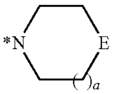

wherein

* represents a binding position with a phosphorus atom, a represents an integer from 0 to 2, E represents $CH_2$, CH-$A^1$, or N-$A^2$, $A^1$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, amino substituted with a removable group under a basic condition, mono($C_{1-6}$ alkyl)amino substituted with a removable group under a basic condition, di($C_{1-6}$ alkyl)amino, tri($C_{1-6}$ alkyl) ammonio, amino substituted with amidino substituted with a removable group under a basic condition, or a substituent represented by the following formula [3]:

[3]

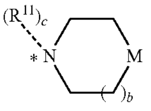

wherein

* represents a binding position with E, b represents an integer from 0 to 2, c represents 0 or 1, $R^{11}$ represents $C_{1-6}$ alkyl, and M represents $CH_2$, an oxygen atom, a sulfur atom, or N-(a removable group under a basic condition), and $A^2$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, a removable group under a basic condition, aryl, or heteroaryl, in the presence of at least one reaction accelerator selected from the group consisting of a tetra $C_{1-18}$ alkyl ammonium chloride, choline chloride, a 1-$C_{1-18}$ alkyl-3-$C_{1-18}$ alkylimidazolium chloride, 1-$C_{1-18}$ alkyl-1-$C_{1-18}$ alkylpyrrolidinium chloride, 1-ethylpyridinium bromide, 1-ethylpyridinium chloride and 1-butylpyridinium chloride to obtain the compound of the formula [C]:

[C]

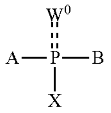

wherein $W^0$ and X are as defined above,

A represents a group obtained by removing one hydrogen atom of the hydroxyl group or the primary or secondary amino group of the compound [A] from the compound [A], and B represents a group obtained by removing the substituent of the formula [1] from the compound [B], wherein the compound [A] and the compound [B] contain one or more nucleoside units, provided that adjacent nucleoside units in the compounds are binding to each other via a phosphate bond if the compound [A] and the compound [B] contain multiple nucleoside units in its molecule, wherein the one or more nucleoside units of the compound [A] is represented by formula [4d],

[4d]

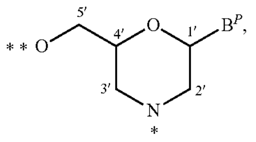

wherein

* represents (1) a binding position with a phosphate bond to an oxygen atom at the 5'-position of an adjacent nucleoside unit, (2) a binding position with a hydrogen atom, or (3) a binding position with a substituent [6];

** represents (1) a binding position with a phosphate bond to an oxygen atom at the 3'-position of an adjacent nucleoside unit, (2) a binding position with a hydrogen atom, or (3) a binding position with a substituent [6] of the following formula [6];

G-T* [6]

wherein

* represents a binding position with ** O or *N in the formula [4d],

G represents (1) a silyl substituent, (2) long-chain $C_{10-300}$alkyl-carbonyl, (3) benzoyl substituted with 1 to 5 long-chain $C_{10-300}$ alkyloxy and/or long-chain $C_{10-300}$alkenyloxy, or (4) a substituent represented by the following formula [7]:

Z-L* [7]

wherein

* represents a binding position with T,

Z represents (1) (soluble polymer soluble in an organic solvent)-oxy, (2) (soluble polymer soluble in an organic solvent)-amino, (3) long-chain $C_{10-300}$alkyloxy, '(4) a solid phase carrier, or '(5) a substituent represented by one of the following formula [8A], formula [8B], formula [8C], formula [8D], formula [8E], formula [8F], formula [8G], formula [8H], formula, formula, formula [8K], formula [8L], formula [8M], and formula [8N]:

[8A]

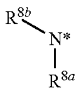

[8B]

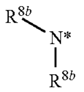

[8C]

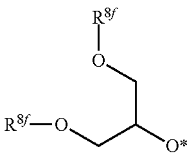

[8D]

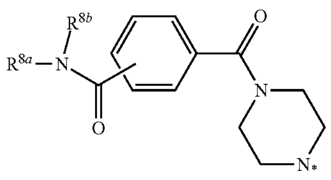

[8E]

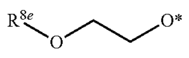

[8F]

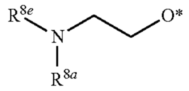

[8G]

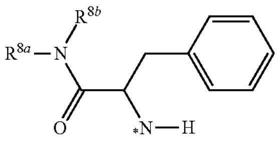

[8H]

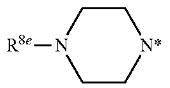

-continued

[8I]

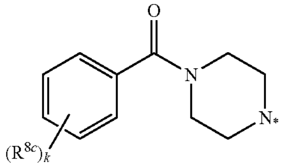

[8J]

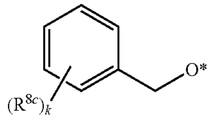

[8K]

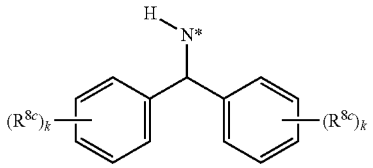

[8L]

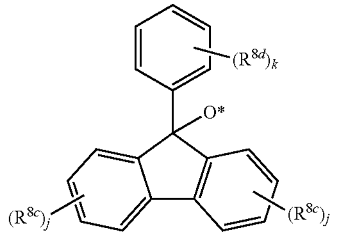

[8M]

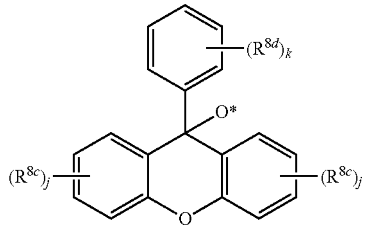

[8N]

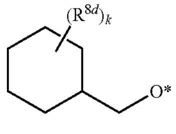

wherein

* represents a binding position with L, j represents an integer from 0 to 4, k represents an integer from 0 to 5, $R^{8a}$ represents a hydrogen atom or $C_{1-6}$ alkyl, $R^{8b}$ is the same or different and each represent long-chain $C_{10-300}$alkyl, $R^{8c}$ is the same or different and each represent a substituent represented by one of the following formula [9A], formula [9B], formula [9C], formula [9D] and formula [9E]:

[9A]

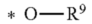

[9B]

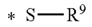

[9C]

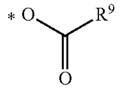

[9D]

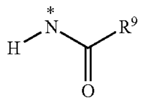

[9E]

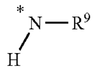

wherein

* represents a binding position, and $R^9$ represents long-chain $C_{10-300}$alkyl and/or long-chain $C_{10-300}$alkenyl, $R^{8d}$ is the same or different and each represent a hydrogen atom, a halogen, long-chain $C_{10-300}$ alkyl optionally substituted with 1 to 13 halogens, or long-chain $C_{10-300}$alkyloxy optionally substituted with 1 to 13 halogens, $R^{8e}$ represents (1) long-chain $C_{10-300}$alkyl, (2) long-chain $C_{10-300}$alkyl-carbonyl, or (3) benzoyl substituted with 1 to 5 long-chain $C_{10-300}$alkyloxy and/or long-chain $C_{10-300}$alkenyloxy, and $R^{8f}$ represents (1) long-chain $C_{10-300}$alkyl, (2) long-chain $C_{10-300}$alkyl-carbonyl, or (3) long-chain $C_{10-300}$alkenyl-carbonyl, and L represents a substituent represented by formula [10]:

[10]

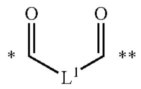

wherein

* represents a binding position with Z,

** represents a binding position with T, and $L^1$ represents an optionally substituted $C_{2-10}$ alkylene or an optionally substituted $C_{6-10}$ arylene, and T represents a single bond or a substituent represented by formula [11]:

[11]

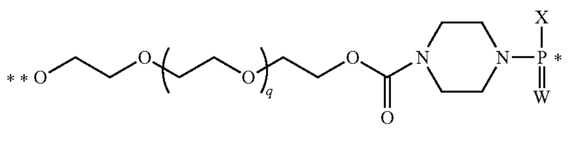

wherein

X is as defined above,

W is as defined above for $W^0$,

* represents a binding position with ** O or *N in the formula [4d],

** represents a binding position with G, and q represents an integer from 0 to 10, provided that T is a single bond when G is a silyl substituent, $B^P$ represents an optionally protected nucleic acid base, and the one or more nucleoside units of the compound [B] is represented by formula [4h],

[4h]

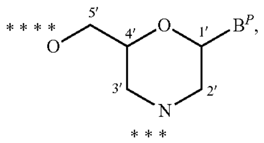

wherein $B^P$ is as defined above;

*** represents (1) a binding position with a phosphorous atom of the phosphate bond to an oxygen atom at the 3'-position of or a nitrogen atom at the 3'-position of an adjacent nucleoside unit, (2) a binding position with the substituent of the formula [1], or (3) a binding position with a removable group under an acidic condition; and the substituent of the formula [1] is represented by the following formula [1A]:

[1A]

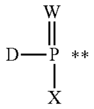

wherein

** represents a binding position,

D represents a halogen, 5- to 6-membered saturated cyclic amino, or di($C_{1-6}$ alkyl)amino, W represents a lone pair of electrons, an oxygen atom, or a sulfur atom, and X represents a hydroxyl group substituted with a removable group under a neutral condition, 1,1,3,3-tetra($C_{1-6}$ alkyl)guanidyl, $C_{1-6}$ alkoxy, di($C_{1-6}$ alkyl)amino, mono(amino-$C_{1-6}$ alkyl substituted with a removable group under a basic condition) amino, di(amino-$C_{1-6}$ alkyl substituted with a removable group under a basic condition)amino, or a substituent represented by the following formula [2];

[2]

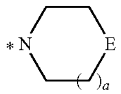

wherein

* represents a binding position with a phosphorus atom, a represents an integer from 0 to 2, E represents $CH_2$, CH-$A^1$, or N-$A^2$, $A^1$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, amino substituted with a removable group under a basic condition, mono($C_{1-6}$ alkyl)amino substituted with a removable group under a basic condition, di($C_{1-6}$ alkyl)amino, tri($C_{1-6}$ alkyl)ammonio, amino substituted with amidino substituted with a removable group under a basic condition, or a substituent represented by the following formula [3]:

[3]

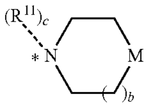

wherein

* represents a binding position with E, b represents an integer from 0 to 2, c represents 0 or 1, $R^{11}$ represents $C_{1-6}$ alkyl, and M represents $CH_2$, an oxygen atom, a sulfur atom, or N-(a removable group under a basic condition), and $A^2$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, a removable group under a basic condition, aryl, or heteroaryl.

2. The method according to claim 1, wherein the reaction accelerator is at least one selected from the group consisting of tetrabutylammonium chloride, 1-butyl-1-methylpyrrolidinium chloride, and 1-methyl-3-N-octylimidazolium chloride.

3. The method according to claim 1, wherein the phosphate bonds between the nucleoside units of the compound [A] and the compound [B] are each the same or different and are each represented by formula [5]:

[5]

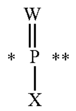

wherein one of * and ** represents an oxygen atom at the 3'-position of a nucleoside unit, and the other of * and ** represents a binding position with an oxygen atom at the 5'-position of a nucleoside unit different from said nucleoside unit, W is an oxygen atom or a sulfur atom, and X is a hydroxyl group substituted with a removable group under a neutral condition, 1,1,3,3-tetra($C_{1-6}$ alkyl)guanidyl, $C_{1-6}$ alkoxy, di($C_{1-6}$ alkyl)amino, mono(amino- $C_{1-6}$ alkyl substituted with a removable group under a basic condition)amino, di(amino-$C_{1-6}$ alkyl substituted with a removable group under a basic condition)amino, or a substituent represented by formula [2]:

[2]

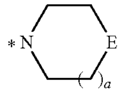

wherein

* represents a binding position with a phosphorus atom, a represents an integer from 0 to 2, E represents $CH_2$, CH-$A^1$, or N-$A^2$, $A^1$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, mono ($C_{1-6}$ alkyl)amino substituted with a removable group under a basic condition, di($C_{1-6}$ alkyl) amino, tri($C_{1-6}$ alkyl)ammonio, amino substituted with amidino substituted with a removable group under a basic condition, or a substituent represented by formula [3]:

[3]

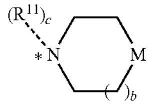

wherein

* represents a binding position with E, b represents an integer from 0 to 2, c represents 0 or 1, $R^{11}$ represents $C_{1-6}$ alkyl, and M represents $CH_2$, an oxygen atom, a sulfur atom, or N-(a removable group under a basic condition), and $A^2$ represents $C_{1-6}$ alkyl, mono($C_{1-6}$ alkyl)amino-$C_{1-6}$ alkyl substituted with a removable group under a basic condition, di($C_{1-6}$ alkyl)amino-$C_{1-6}$ alkyl, tri($C_{1-6}$ alkyl)ammonio-$C_{1-6}$ alkyl, a removable group under a basic condition, aryl, or heteroaryl.

4. The method according to claim 1, wherein the compound [B] is a compound represented by formula [B-1]:

[B-1]

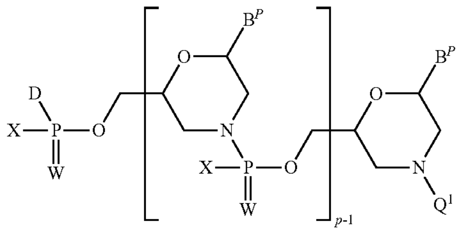

wherein each $B^P$ is the same or different and is an optionally protected nucleic acid base, D is a halogen, 5- to 6-membered saturated cyclic amino, or di($C_{1-6}$ alkyl)amino, p represents an integer from 1 to 10, $Q^1$ represents a removable group under an acidic condition, each W is the same or different and represents an oxygen atom or a sulfur atom, and each X is the same or different and is a hydroxyl group substituted with a removable group under a neutral condition, 1,1,3,3-tetra($C_{1-6}$ alkyl)guanidyl, $C_{1-6}$ alkoxy, di($C_{1-6}$ alkyl)amino, mono(amino-$C_{1-6}$ alkyl substituted with a removable group under a basic condition)amino, di(amino-$C_{1-6}$ alkyl substituted with a removable group under a basic condition) amino, or a substituent represented by formula [2], the compound [A] is a compound represented by formula [A-1]:

[A-1]

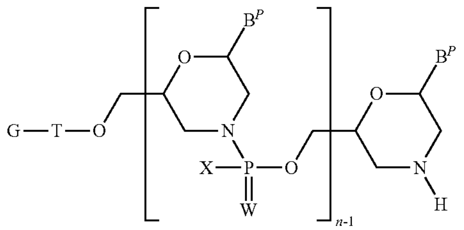

wherein $B^P$, W and X are as defined above,

G is (1) a silyl substituent, (2) long-chain $C_{10-300}$alkyl-carbonyl, (3) benzoyl substituted with 1 to 5 long-chain $C_{10-300}$ alkyloxy and/or long-chain $C_{10-300}$alkenyloxy, or (4) a substituent represented by the following formula [7]:

Z-L* [7]

wherein

* represents a binding position with T,

Z represents (1) (soluble polymer soluble in an organic solvent)-oxy, (2) (soluble polymer soluble in an organic solvent)-amino, (3) long-chain $C_{10-300}$alkyloxy, (4) a solid phase carrier, or (5) a substituent represented by one of the following formula [8A], formula [8B], formula [8C], formula [8D], formula [8E], formula [8F], formula [8G], formula [8H], formula, formula, formula [8K], formula [8L], formula [8M], and formula [8N]:

[8A]

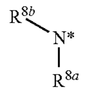

-continued

[8B]

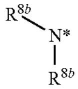

[8C]

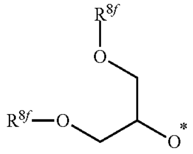

[8D]

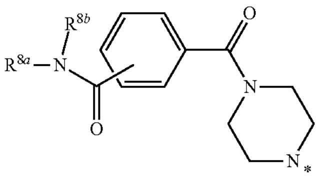

[8E]

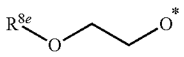

[8F]

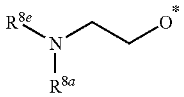

[8G]

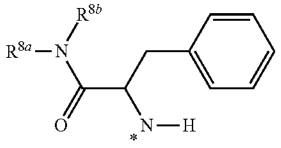

[8H]

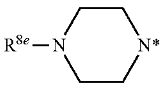

[8I]

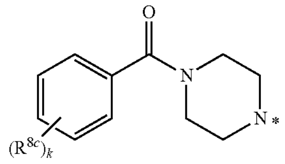

[8J]

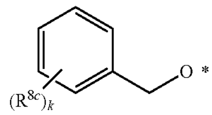

[8K]

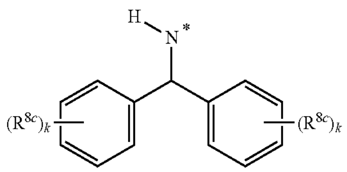

[8L]

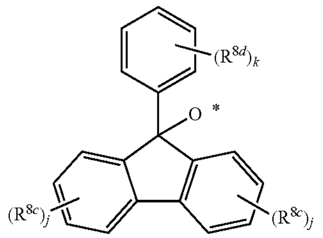

-continued

[8M]

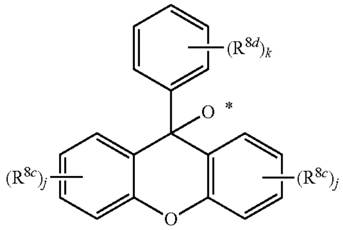

[8N]

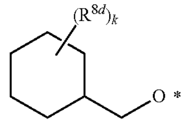

wherein

* represents a binding position with L, j represents an integer from 0 to 4, k represents an integer from 0 to 5, $R^{8a}$ represents a hydrogen atom or $C_{1-6}$ alkyl, $R^{8b}$ is the same or different and each represent $C_{10-300}$long-chain alkyl, $R^{8c}$ is the same or different and each represent a substituent represented by one of the following formula [9A], formula [9B], formula [9C], formula [9D] and formula [9E]:

[9A]

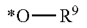

[9B]

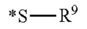

[9C]

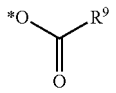

[9D]

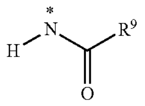

[9E]

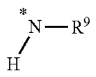

wherein

* represents a binding position, and $R^9$ represents $C_{10-300}$long-chain alkyl and/or $C_{10-300}$long-chain alkenyl, $R^{8d}$ is the same or different and each represent a hydrogen atom, a halogen, long-chain $C_{10-300}$alkyl optionally substituted with 1 to 13 halogens, or long-chain $C_{10-300}$alkyloxy optionally substituted with 1 to 13 halogens, $R^{8e}$ represents (1) long-chain $C_{10-300}$alkyl, (2) long-chain $C_{10-300}$alkyl-carbonyl, or (3) benzoyl substituted with 1 to 5 long-chain $C_{10-300}$alkyloxy and/or long-chain $C_{10-300}$alkenyloxy, and $R^{8f}$ represents
(1) long-chain $C_{10-300}$alkyl,
(2) long-chain $C_{10-300}$alkyl-carbonyl, or
(3) long-chain $C_{10-300}$alkenyl-carbonyl, and
L represents a substituent represented by formula [10]:

[10]

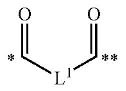

wherein
* represents a binding position with Z,
** represents a binding position with T, and
$L^1$ represents an optionally substituted $C_{2-10}$ alkylene or an optionally substituted $C_{6-10}$ arylene, and
T represents a single bond or a substituent represented by formula [11]:

[11]

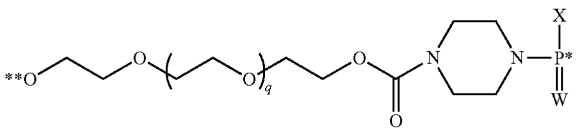

wherein
X is as defined above,
W is a lone pair of electrons, an oxygen atom, or a sulfur atom,
* represents a binding position with ** O or *N in the formula [4d],
** represents a binding position with G, and
q represents an integer from 0 to 10,
provided that T is a single bond when G is a silyl substituent, and
n represents an integer from 0 to 50, and
the compound [C] is a compound represented by formula [C-1]:

[C-1]

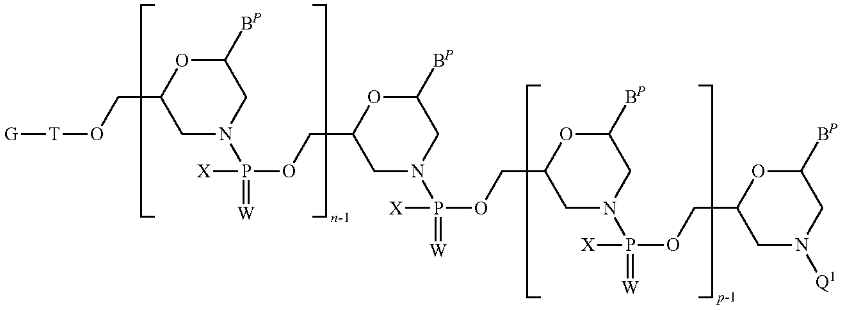

wherein $B^P$, $Q^1$, W, X, G, T, n and p are as defined above.

5. The method according to claim 4, wherein the method further comprises:
removing $Q^1$ in situ subsequently by adding a solution containing an acid to a reaction mixture containing the compound [C-1] prepared by the method according to claim 4, to form a compound represented by formula [E-1]

[E-1]

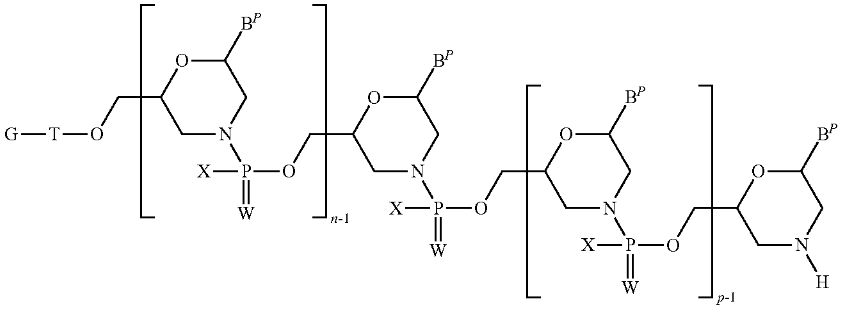

wherein n, p, $B^P$, G, T, W and X are as defined in claim 4.

6. The method according to claim 4, wherein the method comprises removing $Q^1$ from a compound of formula [A-1-1]:

[A-1-1]

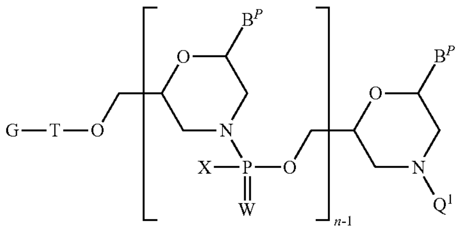

wherein $Q^1$ is trityl, monomethoxytrityl or dimethoxytrityl, and n, $B^P$, W, X, G and T are as defined in claim 4, in the presence of trifluoroacetic acid and 2,2,2-trifluoroethanol, and optionally triisopropylsilane or ethanol, to form the compound of formula [A-1].

7. The method according to claim 4, wherein the method further comprises supplying a solution containing the compound of formula [A-1] and a solution containing the compound of formula [B-1] to a flow reactor to form the compound of formula [C-1], and optionally, supplying a solution containing the compound of formula [C-1] and a solution containing an acid to a flow reactor to remove $Q^1$ to form a compound of formula [E-1]:

[E-1]

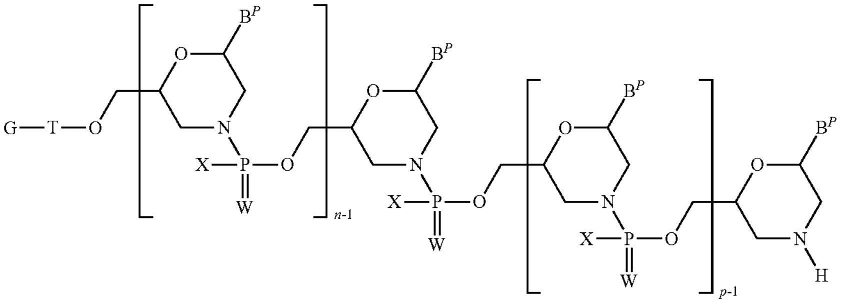

wherein n, p, $B^P$, G, T, W and X are as defined in claim 4.

8. The method according to claim 6, wherein the method further comprises supplying a solution containing the compound of formula [A-1-1] and a solution containing an acid to a flow reactor to remove $Q^1$ to form a compound of formula [A-1], and supplying a solution containing the compound of formula [A-1] and a solution containing the compound of formula [B-1] to a subsequent flow reactor to form the compound of formula [C-1].

9. The method according to claim 1, wherein the optionally protected nucleic acid base is independently adenine, guanine, hypoxanthine, cytosine, thymine, uracil or a modified base thereof.

10. The method according to claim 1, wherein the optionally protected nucleic acid base is a nucleic acid base wherein an amino group and/or a hydroxyl group of the nucleic acid base is protected with a protecting group, and the protecting group of the amino group is independently selected from the group consisting of benzoyl, 4-methoxybenzoyl, acetyl, propionyl, butyryl, isobutyryl phenylacetyl, phenoxyacetyl, 4-tert-butylphenoxyacetyl, 4-isopropylphenoxyacetyl, and (dimethylamino)methylene, and the protecting group of the hydroxy group is independently selected from the group consisting of 2-cyanoethyl, 4-nitrophenethyl, phenylsulfonylethyl, methylsulfonylethyl, trimethylsilylethyl, phenyl optionally substituted with 1 to 5 electron-withdrawing groups at any substitutable positions, diphenylcarbamoyl, dimethylcarbamoyl, diethylcarbamoyl, methylphenylcarbamoyl, 1-pyrolidinylcarbamoyl, morpholinocarbamoyl, 4-(tert-butylcarboxy)benzyl, 4-[(dimethylamino)carboxy]benzyl, and 4-(phenylcarboxy)benzyl.

* * * * *